US007235360B2

(12) United States Patent
Reff et al.

(10) Patent No.: US 7,235,360 B2

(45) **Date of Patent: *Jun. 26, 2007**

(54) METHOD FOR INTEGRATING GENES AT SPECIFIC SITES IN MAMMALIAN CELLS VIA HOMOLOGOUS RECOMBINATION AND VECTORS FOR ACCOMPLISHING THE SAME

(75) Inventors: Mitchell R. Reff, San Diego, CA (US); Richard Spence Barnett, San Marcos, CA (US); Karen Retta McLachlan, Solana Beach, CA (US)

(73) Assignee: Biogen Idec Inc., Cambridge, MA (US)

( * ) Notice: Subject to any disclaimer, the term of this patent is extended or adjusted under 35 U.S.C. 154(b) by 434 days.

This patent is subject to a terminal disclaimer.

(21) Appl. No.: 10/817,950

(22) Filed: Apr. 6, 2004

(65) Prior Publication Data

US 2004/0166528 A1 Aug. 26, 2004

Related U.S. Application Data

(63) Continuation of application No. 10/109,853, filed on Apr. 1, 2002, now Pat. No. 6,841,383, which is a continuation of application No. 09/343,485, filed on Jun. 30, 1999, now Pat. No. 6,413,777, which is a continuation of application No. 09/023,715, filed on Feb. 13, 1998, now Pat. No. 5,998,144, which is a continuation-in-part of application No. 08/819,866, filed on Mar. 14, 1997, now Pat. No. 5,830,698.

(51) Int. Cl.
*C12Q 1/68* (2006.01)

(52) U.S. Cl. ........................................ 435/6; 435/320.1

(58) Field of Classification Search ..................... None
See application file for complete search history.

(56) References Cited

U.S. PATENT DOCUMENTS

| | | | | |
|---|---|---|---|---|
| 5,202,238 | A | 4/1993 | Fell | |
| 5,464,764 | A | 11/1995 | Capecchi | 435/172.3 |
| 5,648,267 | A | 7/1997 | Reff | |
| 5,830,698 | A * | 11/1998 | Reff et al. | 435/69.1 |
| 5,998,144 | A * | 12/1999 | Reff et al. | 435/6 |
| 6,413,777 | B1 * | 7/2002 | Reff et al. | 435/463 |
| 6,841,383 | B2 | 1/2005 | Reff et al. | |

FOREIGN PATENT DOCUMENTS

| | | |
|---|---|---|
| WO | WO 90/11354 | 10/1990 |
| WO | WO 91/06667 | 5/1991 |
| WO | WO 93/09222 | 5/1993 |
| WO | WO 93/24642 | 12/1993 |
| WO | WO 94/05784 | 3/1994 |
| WO | WO 94/11523 | 5/1994 |

OTHER PUBLICATIONS

Sutcliffe et al., "Nucleotide sequence of the ampicillin resistance gene of *Escherichia coli* plasmid pBR322," 1978, Proc. Natl. Acad. Sci., U.S.A., 75(8): 3737-3741.

Barnett et al., "Antibody production in Chinese hamster ovary cells using an impaired selectable marker," 1995, American Chemical Society Symposium Series, Chapter 3, 604:27-40.

al-Shawi R, et al., "Expression of a foreign gene in a line of transgenic mice is modulated by a chromosomal position effect," *Mol Cell Biol*, 1990, 10: 1192-8.

Barnett RS, et al., "Antibody production in chinese hamster ovary cells using an impaired selectable marker," *ACS Symposium Series: Antibody Expression and Engineering*, 1997, 604: 27-40.

Capecchi MR, "Altering the genome by homologous recombination," *Science*, 1989, 244: 1288-92.

Choulika A, et al., "Induction of homologous recombination in mammalian chromosomes by using the I-Scel system of *Saccharomyces cerevisiae," Mol Cell Biol*, 1995, 15: 1968-73.

Dariavach P, et al., "Human lg superfamily CTLA-4 gene: chromosomal localization and identity of protein sequence between murine and human CTLA-4 cytoplasmic domains," *Eur J Immunol*, 1988, 18: 1901-5.

Donahue TF, et al., "The nucleotide sequence of the HIS4 region of yeast," *Gene*, 1982, 18: 47-59.

Flesher AR, et al., "Fluorohore-labeled carbohydrate analysis of immunoglobulin fusion proteins: Correlation of oligosachharide content with in vivo clearance profile," *Biotechnology & Bioengineering*, 1995, 46: 399-407.

Fukushige S, et al., "Genomic targeting with a positive-selection lox integration vector allows highly reproducible gene expression in mammalian cells." *Proc Natl Acad Sci U S A*, 1992, 89: 7905-9.

Linsley PS, et al., "CTLA-4 is a second receptor for the B cell activation antigen B7," *J Exp Med*, 1991, 174: 561-9.

Meinkoth J, et al., "Unstable and stable CAD gene amplification: importance of flanking sequences and nuclear environment in gene amplification," *Mol Cell Biol*, 1987, 7: 1415-24.

Morrow B, et al., "Gene targeting in mammalian cells by homologous recombination," *Curr Opin Biotechnol*, 1993, 4: 577-82.

Newman R, et al., ""Primatization" of recombinant antibodies for immunotherapy of human diseases: a macaque/human chimeric antibody against human CD4." *Biotechnology* (*N Y*), 1992, 10: 1456-60.

(Continued)

*Primary Examiner*—John S. Brusca
(74) *Attorney, Agent, or Firm*—Pillsbury Winthrop Shaw Pittman LLP

(57) ABSTRACT

A method for achieving site specific integration of a desired DNA at a target site in a mammalian cell via homologous recombination is described. This method provides for the reproducible selection of cell lines wherein a desired DNA is integrated at a predetermined transcriptionally active site previously marked with a marker plasmid. The method is particularly suitable for the production of mammalian cell lines which secrete mammalian proteins at high levels, in particular immunoglobulins. Novel vectors and vector combinations for use in the subject cloning method are also provided.

41 Claims, 75 Drawing Sheets

OTHER PUBLICATIONS

Peakman TC, et al., "Comparison of expression of a humanized monoclonal antibody in mouse NSO myeloma cells and Chinese hamster ovary cells," *Hum Antibodies Hybridomas*. 1994, 5: 65-74.
Ramirez-Solis R et al., "Gene targeting in embryonic stem cells," *Methods in Enzymology*, 225:855-878.
Reff ME, "High-level production of recombinant immunoglobulins in mammalian cells," *Curr Opin Biotechnol*, 1993, 4:573-6.
Reff ME, et al., "Depletion of B cells in vivo by a chimeric mouse human monoclonal antibody to CD20," *Blood*, 1994, 83: 435-45.
Rothstein R, "Targeting, disruption, replacement, and allele rescue: integrative DNA transformation in yeast," *Methods Enzymol*, 1991, 194: 281-301.
Sherlock S, et al., "Delta virus hepatitis," *J Hepatol*, 1986, 3: 419-23.
Sutton BJ, et al., "The human lgE network," *Nature*, 1993, 366: 421-8.
Thomas KR, et al., "High frequency targeting of genes to specific sites in the mammalian genome," *Cell*, 1986, 44: 419-28.
Urlaub G, et al., "Effect of gamma rays at the dihydrofolate reductase focus: deletions and inversions," *Somat Cell Mol Genet*, 1986, 12:555-66.
Wahl GM, et al., "Gene amplification causes overproduction of the first three enzymes of UMP synthesis in N-(phosphonacetyl)-L-aspartate-resistant hamster cells," *J Biol Chem*, 1979, 254: 8679-89.
Yoshimura FK, et al., "Different activities of viral enhancer elements before and after stable integration of transfected DNAs," *Mol Cell Biol*, 1987, 7: 1296-9.
Song et al., "Accurate modification of a chomosomal plasmid by homologous recombination in human cells," Proc. Natl. Acad. Sci. USA, p. 6820-6824, (1987).
Lin et al., "Recombination in mouse L cells between DNA introduced into cells and homologous chromosomal sequences," Proc. Natl. Acad. Sci. USA, p. 1391-1395, (1985).
Lucas et al., "High-level production of recmobinant proteins in CHO cells using a dicistronic CHFR intron expression vector," Nucleic Acids Research, p. 1774-1779, (1996).

* cited by examiner

DESMOND

HD = Salmonella HisD Gene
N3 = Neomycin Phosphotransferase Exon 3
D = Murine Dihydrofolate reductase
E = Cytomegalovirus and SV40 Enhancers
SA = Splice acceptor
BT = Mouse Beta Globin Major Promoter
B = Bovine Growth Hormone Polyadenylation
S = SV40 Early Polyadenylation
SV = SV40 Late Polyadenylation

FIG. 2A

Molly

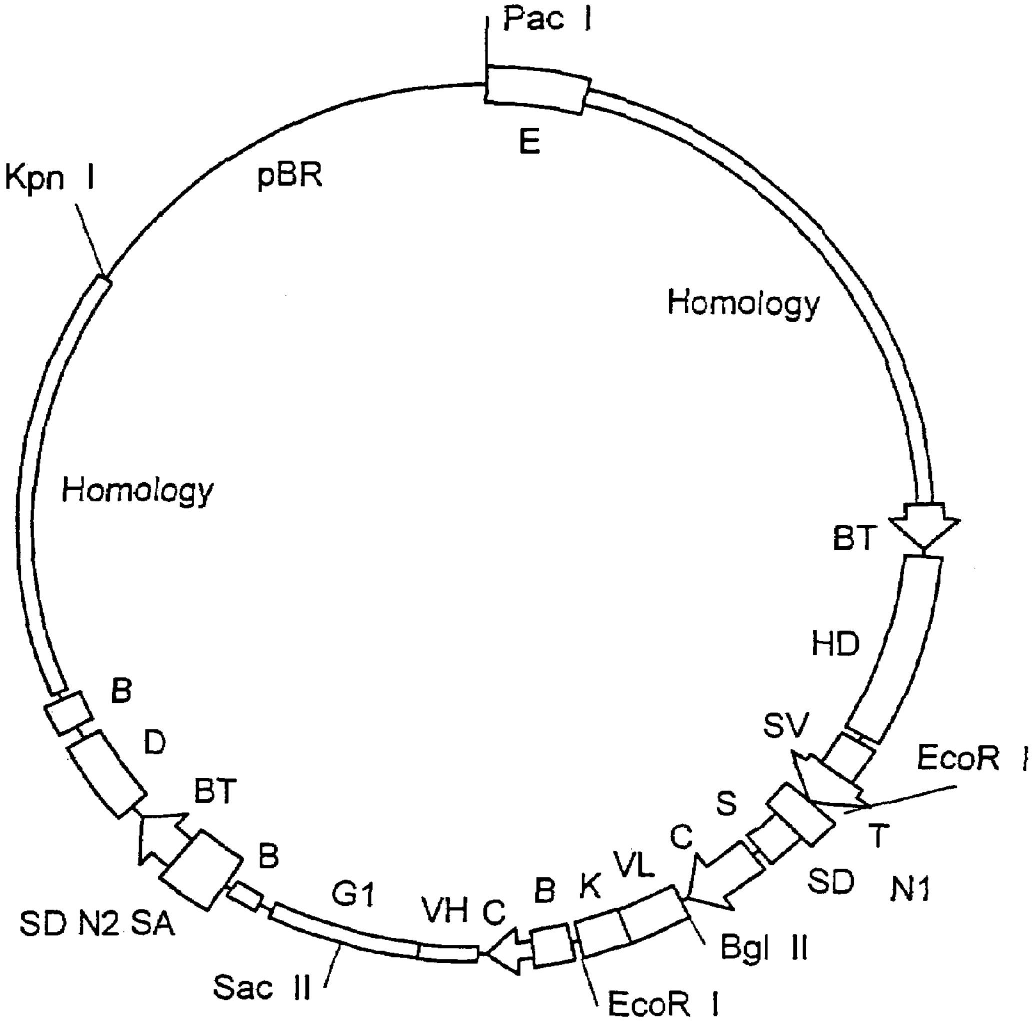

D = Dihydrofolate reductase
N1 + Neomycin Phosphotransferase Exon 1
N2 + Neomycin Phosphotransferase Exon 2
VL = Anti-CD20 Light chain leader + Variable
K = Human Kappa Constant
VH = Anti-CD20 Heavy chain Leader + Variable
G1 = Human Gamma 1 Constant
HD = *Salmonella* Histidinol Dehydrogenase
E = CMV and SV40 enhancers
S = SV40 Origin
SD = Splice donor
SA = Splice acceptor
C = CMV promoter/enhancer
T = HSV TK promoter and *Poloma* enhancers
BT = Mouse Beta Globin Major Promoter
SV = SV40 Late Polyadenylation
B = Bovine Growth Hormone Polyadenylation Southern Analysis of Desmond Marked CHO Cells Northern Analysis of Desmond Marked CHO Cells

Southern Analysis of Anti CD20 Integrants in Marked CHO Cells

FIG. 7A

```
TTTCTAGACC  TAGGGCGGCC  AGCTAGTAGC  TTTGCTTCTC  AATTTCTTAT  TTGCATAATG
                                                                   60
AGAAAAAAAG  GAAAATTAAT  TTTAACACCA  ATTCAGTAGT  TGATTGAGCA  AATGCGTTGC
                                                                  120
CAAAAAGGAT  GCTTTAGAGA  CAGTGTTCTC  TGCACAGATA  AGGACAAACA  TTATTCAGAG
                                                                  180
GGAGTACCCA  GAGCTGAGAC  TCCTAAGCCA  GTGAGTGGCA  CAGCATTCTA  GGGAGAAATA
                                                                  240
TGCTTGTCAT  CACCGAAGCC  TGATTCCGTA  GAGCCACACC  TTGGTAAGGG  CCAATCTGCT
                                                                  300
CACACAGGAT  AGAGAGGGCA  GGAGCCAGGG  CAGAGCATAT  AAGGTGAGGT  AGGATCAGTT
                                                                  360
GCTCCTCACA  TTTGCTTCTG  ACATAGTTGT  GTTGGGAGCT  TGGATAGCTT  GGACAGCTCA
                                                                  420
GGGCTGCGAT  TTCGCGCCAA  ACTTGACGGC  AATCCTAGCG  TGAAGGCTGG  TAGGATTTTA
                                                                  480
TCCCCGCTGC  CATCATGGTT  CGACCATTGA  ACTGCATCGT  CGCCGTGTCC  CAAAATATGG
                                                                  540
GGATTGGCAA  GAACGGAGAC  CTACCCTGGC  CTCCGCTCAG  GAACGAGTTC  AAGTACTTCC
                                                                  600
AAAGAATGAC  CACAACCTCT  TCAGTGGAAG  GTAAACAGAA  TCTGGTGATT  ATGGGTAGGA
                                                                  660
```

FIG. 7B

AAACCTGGTT CTCCATTCCT GAGAAGAATC GACCTTTAAA GGACAGAATT AATATAGTTC 720
TCAGTAGAGA ACTCAAAGAA CCACCACGAG GAGCTCATTT TCTTGCCAAA AGTTTGGATG 780
ATGCCTTAAG ACTTATTGAA CAACCGGAAT TGGCAAGTAA AGTAGACATG GTTTGGATAG 840
TCGGAGGCAG TTCTGTTTAC CAGGAAGCCA TGAATCAACC AGGCCACCTT AGACTCTTTG 900
TGACAAGGAT CATGCAGGAA TTTGAAAGTG ACACGTTTTT CCCAGAAATT GATTTGGGGA 960
AATATAAACT TCTCCCAGAA TACCCAGGCG TCCTCTCTGA GGTCCAGGAG GAAAAAGGCA 1020
TCAAGTATAA GTTTGAAGTC TACGAGAAGA AAGACTAACA GGAAGATGCT TTCAAGTTCT 1080
CTGCTCCCCT CCTAAAGCTA TGCATTTTTA TAAGACCATG GGACTTTTGC TGGCTTTAGA 1140
TCAGCCTCGA CTGTGCCTTC TAGTTGCCAG CCATCTGTTG TTTGCCCCTC CCCCGTGCCT 1200
TCCTTGACCC TGGAAGGTGC CACTCCCACT GTCCTTTCCT AATAAAATGA GGAAATTGCA 1260
TCGCATTGTC TGAGTAGGTG TCATTCTATT CTGGGGGGTG GGGTGGGGCA GGACAGCAAG 1320

FIG. 7C

GGGGAGGATT GGGAAGACAA TAGCAGGCAT GCTGGGGATG CGGTGGGCTC TATGGAACCA 1380
GCTGGGGCTC GAAGCGGCCG CCCATTTCGC TGGTGGTCAG ATGCGGGATG GCGTGGGACG 1440
CGGCGGGGAC CGTCACACTG AGGTTTTCCG CCAGACGCCA CTGCTGCCAG GCGCTGATGT 1500
GCCCGGCTTC TGACCATGCG GTCGCGTTCG GTTGCACTAC GCGTACTGTG AGCCAGAGTT 1560
GCCCGGCGCT CTCCGGCTGC GGTAGTTCAG GCAGTTCAAT CAACTGTTTA CCTTGTGGAG 1620
CGACATCCAG AGGCACTTCA CCGCTTGCTA GCGGCTTACC ATCCAGCGCC ACCATCCAGT 1680
GCAGGAGCTC GTTATCGCTA TGACGGAACA GGTATTCGCT GGTCACTTCG ATGGTTTGCC 1740
CGGATAAACG GAACTGGAAA AACTGCTGCT GGTGTTTTGC TTCCGTCAGC GCTGGATGCG 1800
GCGTGCGGTC GGCAAAGACC AGACCGTTCA TACAGAACTG GCGATCGTTC GGCGTATCAC 1860
CAAAATCACC GCCGTAAGCC GACCACGGGT TGCCGTTTTC ATCATATTTA ATCAGCGACT 1920
GATCCACCCA GTCCCAGACG AAGCCGCCCT GTAAACGGGG ATACTGACGA AACGCCTGCC 1980

FIG. 7D

AGTATTTAGC GAAACCGCCA AGACTGTTAC CCATCGCGTG GGCGTATTCG CAAAGGATCA 2040
GCGGGCGCGT CTCTCCGGGT AGCGAAAGCC ATTTTTTGAT GGACCATTTC GGACCAGCCG 2100
GGAAGGGCTG GTCTTCATCC ACGCGCGCGT ACATCGGGCA AATAATATCG GTGGCCGTGG 2160
TGTCGGCTCC GCCGCCTTCA TACTGCACCG GGCGGGAAGG ATCGACAGAT TTGATCCAGC 2220
GATACAGCGC GTCGTGATTA GCGCCGTGGC CTGATTCATT CCCCAGCGAC CAGATGATCA 2280
CACTCGGGTG ATTACGATCG CGCTGCACCA TTCGCGTTAC GCGTTCGCTC ATCGCCGGTA 2340
GCCAGCGCGG ATCATCGGTC AGACGATTCA TTGGCACCAT GCCGTGGGTT TCAATATTGG 2400
CTTCATCCAC CACATACAGG CCGTAGCGGT CGCACAGCGT GTACCACAGC GGATGGTTCG 2460
GATAATGCGA ACAGCGCACG GCGTTAAAGT TGTTCTGCTT CATCAGCAGG ATATCCTGCA 2520
CCATCGTCTG CTCATCCATG ACCTGACCAT GCAGAGGATG ATGCTCGTGA CGGTTAACGC 2580
CTCGAATCAG CAACGGCTTG CCGTTCAGCA GCAGCAGACC ATTTCCAATC CGCACCTCGC 2640

FIG. 7E

GGAAACCGAC ATCGCAGGCT TCTGCTTCAA TCAGCGTGCC GTCGGCGGTG TGCAGTTCAA 2700
CCACCGCACG ATAGAGATTC GGGATTTCGG CGCTCCACAG TTTCGGGTTT TCGACGTTCA 2760
GACGCAGTGT GACGCGATCG GCATAACCAC CAGGCTCATC GATAATTTCA CCGCCGAAAG 2820
GCGCGGTGCC GCTGGCGACC TGCGTTTCAC CCTGCCATAA AGAAACTGTT ACCCGTAGGT 2880
AGTCACGCAA CTCGCCGCAC ATCTGAACTT CAGCCTCCAG TACAGCGCGG CTGAAATCAT 2940
CATTAAAGCG AGTGGCAACA TGGAAATCGC TGATTTGTGT AGTCGGTTTA TGCAGCAACG 3000
AGACGTCACG GAAAATGCCG CTCATCCGCC ACATATCCTG ATCTTCCAGA TAACTGCCGT 3060
CACTCCAACG CAGCACCATC ACCGCGAGGC GGTTTTCTCC GGCGCGTAAA AATGCGCTCA 3120
GGTCAAATTC AGACGGCAAA CGACTGTCCT GGCTGTAACC GACCCACGCC CCGTTGCACC 3180
ACAGATGAAA CGCCGAGTTA ACGCCATCAA AAATAATTCG CGTCTGGCCT TCCTGTAGCC 3240
AGCTTTCATC AACATTAAAT GTGAGCGAGT AACAACCCGT CGGATTCTCC GTGGGAACAA 3300

FIG. 7F

ACGGCGGATT GACCGTAATG GGATAGGTTA CGTTGGTGTA GATGGGCGCA TCGTAACCGT 3360
GCATCTGCCA GTTTGAGGGG ACGACGACAG TATCGGCCTC AGGAAGATCG CACTCCAGCC 3420
AGCTTTCCGG CACTGCTTCT GGTGCCGGAA ACCAGGCAAA GCGCCATTCG CCATTCAGGC 3480
TGCGCAACTG TTGGGAAGGG CGATCGGTGC GGGCCTCTTC GCTATTACGC CAGCTGGCGA 3540
AAGCGGGATG TGCTGCAAGG CGATTAAGTT GGGTAACGCC AGGGTTTTCC CAGTCACGAC 3600
GTTGTAAAAC GACTTAATCC GTCGAGGGGC TGCCTCGAAG CAGACGACCT TCCGTTGTGC 3660
AGCCAGCGGC GCCTGCGCCG GTGCCCACAA TCGTGCGCGA ACAAACTAAA CCAGAACAAA 3720
TCATACCGGC GGCACCGCCG CCACCACCTT CTCCTGTGCC TAACATTCCA GCGCCTCCAC 3780
CACTACCACC ACCATCGATG TCTGAATTGC CGCCCGCTCC ACCAATGCCG ACGGAACCTC 3840
AACCCGCTGC ACCTTTAGAC GACAGACAAC AATTGTTGGA AGCTATTAGA AACGAAAAAA 3900
ATCGCACTCG TCTCAGACCG GCTCTCTTAA GGTAGCTCAA ACCAAAAACG GCGCCCGAAA 3960

FIG. 7G

CCAGTACAAT AGTTGAGGTG CCGACTGTGT TGCCTAAAGA GACATTTGAG CTTAAACCGC 4020
CGTCTGCACC ACCGCCACCA CCTCCGCCTC CGCCTCCGCC GCCAGCCCCG CCTGCGCCTC 4080
CACCGATGGT AGATTCATCA TCAGCTCCAC CACCGCCGCC ATTAGTAGAT TTGCCGTCTG 4140
AAATGTTACC ACCGCCTGCA CCATCGCTTT CTAACGTGTT GTCTGAATTA AAATCGGGCA 4200
CAGTTAGATT GAAACCCGCC CAAAAACGCC CGCAATCAGA AATAATTCCA AAAAGCTCAA 4260
CTACAAATTT GATCGCGGAC GTGTTAGCCG ACACAATTAA TAGGCGTCGT GTGGCTATGG 4320
CAAAATCGTC TTCGGAAGCA ACTTCTAACG ACGAGGGTTG GGACGACGAC GATAATCGGC 4380
CTAATAAAGC TAACACGCCC GATGTTAAAT ATGTCCAAGC TACTAGTGGT ACCTTAATTA 4440
AGGGGCGGAG AATGGGCGGA ACTGGGCGGA GTTAGGGGCG GGATGGGCGG AGTTAGGGGC 4500
GGGACTATGG TTGCTGACTA ATTGAGATGC ATGCTTTGCA TACTTCTGCC TGCTGGGGAG 4560
CCTGGGGACT TTCCACACCT GGTTGCTGAC TAATTGAGAT GCATGCTTTG CATACTTCTG 4620

FIG. 7H

CCTGCTGGGG AGCCTGGGGA CTTTCCACAC CCTAACTGAC ACACATTCCA CAGAATTAAT 4680
TCCCCTAGTT ATTAATAGTA ATCAATTACG GGGTCATTAG TTCATAGCCC ATATATGGAG 4740
TTCCGCGTTA CATAACTTAC GGTAAATGGC CCGCCTGGCT GACCGCTCAA CGACCCCCGC 4800
CCATTGACGT CAATAATGAC GTATGTTCCC ATAGTAACGC CAATAGGGAC TTTCCATTGA 4860
CGTCAATGGG TGGACTATTT ACGGTAAACT GCCCACTTGG CAGTACATCA AGTGTATCAT 4920
ATGCCAAGTA CGCCCCCTAT TGACGTCAAT GACGGTAAAT GGCCCGCCTG GCATTATGCC 4980
CAGTACATGA CCTTATGGGA CTTTCCTACT TGGCAGTACA TCTACGTATT AGTCATCGCT 5040
ATTACCATGG TGATGCGGTT TTGGCAGTAC ATCAATGGGC GTGGATAGCG GTTTGACTCA 5100
CGGGGATTTC CAAGTCTCCA CCCCATTGAC GTCAATGGGA GTTTGTTTTG AAGCTTGGCC 5160
GGCCATATAA ACGGCGGCCA GCTTTATTTA ACGTGTTTAC GTCGAGTCAA TTGTACACTA 5220
ACGACAGTGA TGAAAGAAAT ACAAAAGCGC ATAATATTTT GAACGACGTC GAACCTTTAT 5280

FIG. 7I

TACAAAACAA AACACAAACG AATATCGACA AAGCTAGATT GCTGCTACAA GATTTGGCAA 5340
GTTTTGTGGC GTTGAGCGAA AATCCATTAG ATAGTCCAGC CATCGGTTCG GAAAAACAAC 5400
CCTTGTTTGA AACTAATCGA AACCTATTTT ACAAATCTAT TGAGGATTTA ATATTTAAAT 5460
TCAGATATAA AGACGCTGAA AATCATTTGA TTTTCGCTCT AACATACCAC CCTAAAGATT 5520
ATAAATTTAA TGAATTATTA AAATACATCA GCAACTATAT ATTGATAGAC ATTTCCAGTT 5580
TGTGATATTA GTTTGTGCGT CTCATTACAA TGGCTGTTAT TTTTAACAAC AAACAACTGC 5640
TCGCAGACAA TAGTATAGAA AAGGGAGGTG AACTGTTTTT GTTTAACGGT TCGTACAACA 5700
TTTTGGAAAG TTATGTTAAT CCGGTGCTGC TAAAAAATGG TGTAATTGAA CTAGAAGAAG 5760
CTGCGTACTA TGCCGGCAAC ATATTGTACA AAACCGACGA TCCCAAATTC ATTGATTATA 5820
TAAATTTAAT AATTAAAGCA ACACACTCCG AAGAACTACC AGAAAATAGC ACTGTTGTAA 5880
ATTACAGAAA AACTATGCGC AGCGGTACTA TACACCCCAT TAAAAAAGAC ATATATATTT 5940

FIG. 7J

ATGACAACAA AAAATTTACT CTATACGATA GATACATATA TGGATACGAT AATAACTATG
6000
TTAATTTTTA TGAGGAGAAA AATGAAAAAG AGAAGGAATA CGAAGAAGAA GACGACAAGG
6060
CGTCTAGTTT ATGTGAAAAT AAAATTATAT TGTCGCAAAT TAACTGTGAA TCATTTGAAA
6120
ATGATTTTAA ATATTACCTC AGCGATTATA ACTACGCGTT TTCAATTATA GATAACACTA
6180
CAAATGTTCT TGTTGCGTTT GGTTTGTATC GTTAATAAAA AACAAATTTA GCATTTATAA
6240
TTGTTTTATT ATTCAATAAT TACAAATAGG ATTGAGACCC TTGCAGTTGC CAGCAAACGG
6300
ACAGAGCTTG TCGAGGAGAG TTGTTGATTC ATTGTTTGCC TCCCTGCTGC GGTTTTTGAC
6360
CGAAGTTCAT GCCAGTCCAG CGTTTTTGCA GCAGAAAAGC CGCCGACTTC GGTTTGCGGT
6420
CGCGAGTGAA GATCCCTTTC TTGTTACCGC CAACGCGCAA TATGCCTTGC GAGGTCGCAA
6480
AATCGGCGAA ATTCCATACC TGTTCACCGA CGACGGCGCT GACGCGATCA AAGACGCGGT
6540
GATACATATC CAGCCATGCA CACTGATACT CTTCACTCCA CATGTCGGTG TACATTGAGT
6600

FIG. 7K

GCAGCCCGGC TAACGTATCC ACGCCGTATT CGGTGATGAT AATCGGCTGA TGCAGTTTCT 6660
CCTGCCAGGC CAGAAGTTCT TTTTCCAGTA CCTTCTCTGC CGTTTCCAAA TCGCCGCTTT 6720
GGACATACCA TCCGTAATAA CGGTTCAGGC ACAGCACATC AAAGAGATCG CTGATGGTAT 6780
CGGTGTGAGC GTCGCAGAAC ATTACATTGA CGCAGGTGAT CGGACGCGTC GGGTCGAGTT 6840
TACGCGTTGC TTCCGCCAGT GGCGCGAAAT ATTCCCGTGC ACCTTGCGGA CGGGTATCCG 6900
GTTCGTTGGC AATACTCCAC ATCACCACGC TTGGGTGGTT TTTGTCACGC GCTATCAGCT 6960
CTTTAATCGC CTGTAAGTGC GCTTGGTGAG TTTCCCCGTT GACTGCCTCT TCGTTGTACA 7020
GTTCTTTCGG CTTGTTGCCC GCTTCGAAAC CAATGCCTAA AGAGAGGTTA AAGCCGACAG 7080
CAGCAGTTTC ATCAATCACC ACGATGCCAT GTTCATCTGC CCAGTCGAGC ATCTCTTCAG 7140
CGTAAGGGTA ATGCGAGGTA CGGTAGGAGT TGGCCCTAAT CCAGTCCATT AATGCGTGGT 7200
CGTGCACCAT CAGCACGTTA TCGAATCCTT TGCCACGCAA GTCCGCATCT TCATGACGAC 7260

FIG. 7L

CAAAGCCAGT AAAGTAGAAC GGTTTGTGGT TAATCAGGAA CTGTTCGCCC TTCACTGCCA 7320
CTGACCGGAT GCCGACGCGA AGCGGGTAGA TATCACACTC TGTCTGGCTT TTGGCTGTGA 7380
CGCACAGTTC ATAGAGATAA CCTTCACCCG GTTGCCAGAG GTGCGGATTC ACCACTTGCA 7440
AAGTCCCGCT AGTGCCTTGT CCAGTTGCAA CCACCTGTTG ATCCGCATCA CGCAGTTCAA 7500
CGCTGACATC ACCATTGGCC ACCACCTGCC AGTCAACAGA CGCGTGGTTA CAGTCTTGCG 7560
CGACATGCGT CACTACGGTG ATATCGTCCA CCCAGGTGTT CGGCGTGGTG TAGAGCATTA 7620
CGCTGCGATG GATTCCGGCA TAGTTAAAGA AATCATGGAA GTAAGATTGC TTTTTCTTGC 7680
CGTTTTCGTT GGTAATCACC ATTCCCGGCG GGATAGTCTG CCAGTTCAGT TCGTTGTTCA 7740
CACAAACGGT GATACCCCTC GACGGATTAA AGACTTCAAG CGGTCAACTA TGAAGAAGTG 7800
TTCGTCTTCG TCCCAGTAAG CTATGTCTCT AGAATGTAGC CATCCATCCT TGTCAATCAA 7860
GGCGTTGGTC GCTTCCGGAT TGTTTACATA ACCGGACATA ATCATAGGTC CTCTGACACA 7920

FIG. 7M

TAATACGCCT CTCTGATTAA CGCCCAGCGT TTTCCCGGTA TCCAGATCCA CAACCTTCGC 7980
TTCAAAAAAT GGAACAACTT TACCGACCGC GCCCGGTTTA TCATCCCCCT CGGGTGTAAT 8040
CAGAATAGCT GATGTAGTCT CAGTGAGCCC ATATCCTTGT CGTATCCCTG GAAGATGGAA 8100
GCGTTTTGCA ACCGCTTCCC CGACTTCTTT CGAAAGAGGT GCGCCCCCAG AAGCAATTTC 8160
GTGTAAATTA GATAAATCGT ATTTGTCAAT CAGAGTGCTT TTGGCGAAGA ATGAAAATAG 8220
GGTTGGTACT AGCAACGCAC TTTGAATTTT GTAATCCTGA AGGGATCGTA AAAACAGCTC 8280
TTCTTCAAAT CTATACATTA AGACGACTCG AAATCTACAT ATCAAATATC CGAGTGTAGT 8340
AAACATTCCA AAACCGTGAT GGAATGGAAC AACACTTAAA ATCGCAGTAT CCGGAATGAT 8400
TTGATTGCCA AAAATAGGAT CTCTGGCATG CGAGAATCTA GCGCAGGCAG TTCTATGCGG 8460
AAGGGCCACA CCCTTAGGTA ACCCAGTAGA TCCAGAGGAA TTGTTTTGTC ACGATCAAAG 8520
GACTCTGGTA CAAAATCGTA TTCATTAAAA CCGGGAGGTA GATGAGATGT GACGAAGGTG 8580

FIG. 7N

TACATCGACT GAAATCCCTG GTAATCCGTT TTAGAATCCA TGATAATAAT TTTCTGGATT 8640
ATTGGTAATT TTTTTTGCAC GTTCAAAATT TTTTGCAACC CCTTTTTGGA AACAAACACT 8700
ACGGTAGGCT GCGAAATGTT CATACTGTTG AGCAATTCAC GTTCATTATA AATGTCGTTC 8760
GCGGGCGCAA CTGCAACTCC GATAAATAAC GCGCCCAACA CCGGCATAAA GAATTGAAGA 8820
GAGTTTTCAC TGCATACGAC GATTCTGTGA TTTGTATTCA GCCCATATCG TTTCATAGCT 8880
TCTGCCAACC GAACGGACAT TTCGAAGTAT TCCGCGTACG TGATGTTCAC CTCGATATGT 8940
GCATCTGTAA AAGGAATTGT TCCAGGAACC AGGGCGTATC TCTTCATAGC CTTATGCAGT 9000
TGCTCTCCAG CGGTTCCATT CTCTAGCTTT GCTTCTCAAT TTCTTATTTG CATAATGAGA 9060
AAAAAAGGAA AATTAATTTT AACACCAATT CAGTAGTTGA TTGAGCAAAT GCGTTGCCAA 9120
AAAGGATGCT TTAGAGACAG TGTTCTCTGC ACAGATAAGG ACAAACATCA TTCAGAGGGA 9180
GTACCCAGAG CTGAGACTCC TAAGCCAGTG AGTGGCACAG CATTCTAGGG AGAAATATGC 9240

FIG. 7P

TTGTCATCAC CGAAGCCTGA TTCCGTAGAG CCACACCTTG GTAAGGGCCA ATCTGCTCAC 9300
ACAGGATAGA GAGGGCAGGA GCCAGGGCAG AGCATATAAG GTGAGGTAGG ATCAGTTGCT 9360
CCTCACATTT GCTTCTGACA TAGTTGTGTT GGGAGCTTGG ATCGATCCAC CATGGGCTTC 9420
AATACCCTGA TTGACTGGAA CAGCTGTAGC CCTGAACAGC AGCGTGCGCT GCTGACGCGT 9480
CCGGCGATTT CCGCCTCTGA CAGTATTACC CGGACGGTCA GCGATATTCT GGATAATGCA 9540
AAAACGCGCG GTGACGATGC CCTGCGTGAA TACAGCGCTA AATTTGATAA AACAGAAGTG 9600
ACAGCGCTAC GCGTCACCCC TGAAGAGATC GCCGCCGCCG GCGCGCGTCT GAGCGACGAA 9660
TTAAAACAGG CGATGACCGC TGCCGTCAAA AATATTGAAA CGTTCCATTC CGCGCAGACG 9720
CTACCGCTTG TAGATGTGGA AACCCAGCCA GGCGTGCGTT GCCAGCAGGT TACGCGTCCC 9780
GTCTCGTCTG TCGGTCTGTA TATTCCCGGC GGCTCGGCTC CGCTCTTCTC AACGGTGCTG 9840
ATGCTGGCGA CGCCGGCGCG CATTGCGGGA TGCTAGAAGG TGGTTCTGTG CTCGCCGCCG 9900

FIG. 7Q

CCCATCGCTG ATGAAATCCT CTATGCGGCG CAACTGTGTG GCGTGCAGGA ATTCTTTAAC
9960
CTCGGCGGCG CGCAGGCGAT TGCCGCTCTG GCCTTCGGCA GCGAGTCCGT ACCGAAAGTG
10020
GATAAAATTT TTGGCCCCGG CAACGCCTTT GTAACCGAAG CCAAACGTCA GGTCAGCCAG
10080
CGTCTCGACG GCGCGGCTAT CGATATGCCA GCCGAGCCGT CTGAAGTACT GGTGATCGCA
10140
GACAGCGGCG CAACACCGGA TTTCGTCGCT TCTGACCTGC TCTCCCAGAC TGAGCACGGC
10200
CCGGATTCCC AGGTGATCCT GCTGACGCCT GATGCTGACA TTGCCCGCAA GGTGGCGGAG
10260
GCGGTAGAAC GTCAACTGGC GGAACTGCCG CGCGCGGACA CCGCCTGGCA GGCCCTGAGC
10320
GCCAGTCGTC TGATTGTGAC CAAAGATTTA GCGCAGTGCG TCGCCATCTC TAATCAGTAT
10380
GGGCCGGAAC ACTTAATCAT CCAGACGCGC AATGCGCGCG ATTTGGTGGA TGCGATTACC
10440
AGCGCAGGCT CGGTATTTCT CGGCGACTGG TCGCCGGAAT CCGCCGGTGA TTACGCTTCC
10500
GGAACCAACC ATGTTTTACC GACCTATGGC CATACTGCTA CCTGTTCCAG CCTTGGGTTA
10560

FIG. 7R

GCGGATTTCC AGAAACGGAT GACCGTTCAG GAACTGTCGA AAGCGGGCTT TTCCGCTCTG 10620
GCATCAACCA TTGAAACATT GGCGGGGGCA GAACGTCTGA CCGCCCATAA AAATGCCGTG 10680
ACCCTGCGCG TAAACGCCCT CAAGGAGCAA GCATGAGCAC TGAAAACACT CTCAGCGTCG 10740
CTGACTTAGC CCGTGAAAAT GTCCGCAACC TGGAGATCCA GACATGATAA GATACATTGA 10800
TGAGTTTGGA CAAACCACAA CTAGAATGCA GTGAAAAAAA TGCTTTATTT GTGAAATTTG 10860
TGATGCTATT GCTTTATTTG TAACCATTAT AAGCTGCAAT AAACAAGTTA ACAACAACAA 10920
TTGCATTCAT TTTATGTTTC AGGTTCAGGG GGAGGTGTGG GAGGTTTTTT AAAGCAAGTA 10980
AAACCTCTAC AAATGTGGTA TGGCTGATTA TGATCTCTAG CTCGACGGGG CGCCTGGCCG 11040
CTACTAACTC TCTCCTCCCT CCTTTTTCCT GCAGGCTCAA GGCGCGCATG CCCGACGGCG 11100
AGGATCTCGT CGTGACCCAT GGCGATGCCT GCTTGCCGAA TATCATGGTG GAAAATGGCC 11160
GCTTTTCTGG ATTCATCGAC TGTGGCCGGC TGGGTGTGGC GGACCGCTAT CAGGACATAG 11220

FIG. 7S

CGTTGGCTAC CCGTGATATT GCTGAAGAGC TTGGCGGCGA ATGGGCTGAC CGCTTCCTCG 11280
TGCTTTACGG TATCGCCGCT CCCGATTCGC AGCGCATCGC CTTCTATCGC CTTCTTGACG 11340
AGTTCTTCTG AGCGGGACTC TGGGGTTCGA AATGACCGAC CAAGCGACGC CCAACCTGCC 11400
ATCACGAGAT TTCGATTCCA CCGCCGCCTT CTATGAAAGG TTGGGCTTCG GAATCGTTTT 11460
CCGGGACGCC GGCTGGATGA TCCTCCAGCG CGGGGATCTC ATGCTGGAGT TCTTCGCCCA 11520
CCCCAACTTG TTTATTGCAG CTTATAATGG TTACAAATAA AGCAATAGCA TCACAAATTT 11580
CACAAATAAA GCATTTTTTT CACTGCATTC TAGTTGTGGT TTGTCCAAAC TCATCAATCT 11640
ATCTTATCAT GTCTGGATCG CGGCCGGTCT CTCTCTAGCC CTAGGTCTAG ACTTGGCAGA 11700
ACATATCCAT CGCGTCCGCC ATCTCCAGCA GCCGCACGCG GCGCATCTCG GGCAGCGTTG 11760
GGTCCTGGCC ACGGGTGCGC ATGATCGTGC TCCTGTCGTT GAGGACCCGG CTAGGCTGGC 11820
GGGGTTGCCT TACTGGTTAG CAGAATGAAT CACCGATACG CGAGCGAACG TGAAGCGACT 11880

FIG. 7T

GCTGCTGCAA AACGTCTGCG ACCTGAGCAA CAACATGAAT GGTCTTCGGT TTCCGTGTTT 11940
CGTAAAGTCT GGAAACGCGG AAGTCAGCGC CCTGCACCAT TATGTTCCGG ATCTGCATCG 12000
CAGGATGCTG CTGGCTACCC TGTGGAACAC CTACATCTGT ATTAACGAAG CGCTGGCATT 12060
GACCCTGAGT GATTTTTCTC TGGTCCCGCC GCATCCATAC CGCCAGTTGT TTACCCTCAC 12120
AACGTTCCAG TAACCGGGCA TGTTCATCAT CAGTAACCCG TATCGTGAGC ATCCTCTCTC 12180
GTTTCATCGG TATCATTACC CCCATGAACA GAAATCCCCC TTACACGGAG GCATCAGTGA 12240
CCAAACAGGA AAAAACCGCC CTTAACATGG CCCGCTTTAT CAGAAGCCAG ACATTAACGC 12300
TTCTGGAGAA ACTCAACGAG CTGGACGCGG ATGAACAGGC AGACATCTGT GAATCGCTTC 12360
ACGACCACGC TGATGAGCTT TACCGCAGCT GCCTCGCGCG TTTCGGTGAT GACGGTGAAA 12420
ACCTCTGACA CATGCAGCTC CCGGAGACGG TCACAGCTTG TCTGTAAGCG GATGCCGGGA 12480
GCAGACAAGC CCGTCAGGGC GCGTCAGCGG GTGTTGGCGG GTGTCGGGGC GCAGCCATGA 12540

FIG. 7U

CCCAGTCACG TAGCGATAGC GGAGTGTATA CTGGCTTAAC TATGCGGCAT CAGAGCAGAT 12600
TGTACTGAGA GTGCACCATA TGCGGTGTGA AATACCGCAC AGATGCGTAA GGAGAAAATA 12660
CCGCATCAGG CGCTCTTCCG CTTCCTCGCT CACTGACTCG CTGCGCTCGG TCGTTCGGCT 12720
GCGGCGAGCG GTATCAGCTC ACTCAAAGGC GGTAATACGG TTATCCACAG AATCAGGGGA 12780
TAACGCAGGA AAGAACATGT GAGCAAAAGG CCAGCAAAAG GCCAGGAACC GTAAAAAGGC 12840
CGCGTTGCTG GCGTTTTTCC ATAGGCTCCG CCCCCCTGAC GAGCATCACA AAAATCGACG 12900
CTCAAGTCAG AGGTGGCGAA ACCCGACAGG ACTATAAAGA TACCAGGCGT TTCCCCCTGG 12960
AAGCTCCCTC GTGCGCTCTC CTGTTCCGAC CCTGCCGCTT ACCGGATACC TGTCCGCCTT 13020
TCTCCCTTCG GGAAGCGTGG CGCTTTCTCA TAGCTCACGC TGTAGGTATC TCAGTTCGGT 13080
GTAGGTCGTT CGCTCCAAGC TGGGCTGTGT GCACGAACCC CCCGTTCAGC CCGACCGCTG 13140
CGCCTTATCC GGTAACTATC GTCTTGAGTC CAACCCGGTA AGACACGACT TATCGCCACT 13200

FIG. 7V

GGCAGCAGCC ACTGGTAACA GGATTAGCAG AGCGAGGTAT GTAGGCGGTG CTACAGAGTT 13260
CTTGAAGTGG TGGCCTAACT ACGGCTACAC TAGAAGGACA GTATTTGGTA TCTGCGCTCT 13320
GCTGAAGCCA GTTACCTTCG GAAAAAGAGT TGGTAGCTCT TGATCCGGCA AACAAACCAC 13380
CGCTGGTAGC GGTGGTTTTT TTGTTTGCAA GCAGCAGATT ACGCGCAGAA AAAAAGGATC 13440
TCAAGAAGAT CCTTTGATCT TTTCTACGGG GTCTGACGCT CAGTGGAACG AAAACTCACG 13500
TTAAGGGATT TTGGTCATGA GATTATCAAA AAGGATCTTC ACCTAGATCC TTTTAAATTA 13560
AAAATGAAGT TTTAAATCAA TCTAAAGTAT ATATGAGTAA ACTTGGTCTG ACAGTTACCA 13620
ATGCTTAATC AGTGAGGCAC CTATCTCAGC GATCTGTCTA TTTCGTTCAT CCATAGTTGC 13680
CTGACTCCCC GTCGTGTAGA TAACTACGAT ACGGGAGGGC TTACCATCTG GCCCCAGTGC 13740
TGCAATGATA CCGCGAGACC CACGCTCACC GGCTCCAGAT TTATCAGCAA TAAACCAGCC 13800
AGCCGGAAGG GCCGAGCGCA GAAGTGGTCC TGCAACTTTA TCCGCCTCCA TCCAGTCTAT 13860

FIG. 7W

TAATTGTTGC CGGGAAGCTA GAGTAAGTAG TTCGCCAGTT AATAGTTTGC GCAACGTTGT 13920
TGCCATTGCT GCAGGCATCG TGGTGTCACG CTCGTCGTTT GGTATGGCTT CATTCAGCTC 13980
CGGTTCCCAA CGATCAAGGC GAGTTACATG ATCCCCCATG TTGTGCAAAA AAGCGGTTAG 14040
CTCCTTCGGT CCTCCGATCG TTGTCAGAAG TAAGTTGGCC GCAGTGTTAT CACTCATGGT 14100
TATGGCAGCA CTGCATAATT CTCTTACTGT CATGCCATCC GTAAGATGCT TTTCTGTGAC 14160
TGGTGAGTAC TCAACCAAGT CATTCTGAGA ATAGTGTATG CGGCGACCGA GTTGCTCTTG 14220
CCCGGCGTCA ACACGGGATA ATACCGCGCC ACATAGCAGA ACTTTAAAAG TGCTCATCAT 14280
TGGAAAACGT TCTTCGGGGC GAAAACTCTC AAGGATCTTA CCGCTGTTGA GATCCAGTTC 14340
GATGTAACCC ACTCGTGCAC CCAACTGATC TTCAGCATCT TTTACTTTCA CCAGCGTTTC 14400
TGGGTGAGCA AAAACAGGAA GGCAAAATGC CGCAAAAAAG GGAATAAGGG CGACACGGAA 14460
ATGTTGAATA CTCATACTCT TCCTTTTTCA ATATTATTGA AGCATTTATC AGGGTTATTG 14520

FIG. 7X

TCTCATGAGC GGATACATAT TTGAATGTAT TTAGAAAAAT AAACAAATAG GGGTTCCGCG 14580
CACATTTCCC CGAAAAGTGC CACCTGACGT CTAAGAAACC ATTATTATCA TGACATTAAC 14640
CTATAAAAAT AGGCGTATCA CGAGGCCCTT TCGTCTTCAA GAA 14683

FIG. 8A

```
TTAATTAAGG GGCGGAGAAT GGGCGGAACT GGGCGGAGTT AGGGGCGGGA TGGGCGGAGT   60
TAGGGGCGGG ACTATGGTTG CTGACTAATT GAGATGCATG CTTTGCATAC TTCTGCCTGC  120
TGGGGAGCCT GGGGACTTTC CACACCTGGT TGCTGACTAA TTGAGATGCA TGCTTTGCAT  180
ACTTCTGCCT GCTGGGGAGC CTGGGGACTT TCCACACCCT AACTGACACA CATTCCACAG  240
AATTAATTCC CCTAGTTATT AATAGTAATC AATTACGGGG TCATTAGGTC ATAGCCCATA  300
TATGGAGTTC CGCGTTACAT AACTTACGGT AAATGGCCCG CCTGGCTGAC CGCCCAACGA  360
CCCCCGCCCA TTGACGTCAA TAATGACGTA TGTTCCCATA GTAACGCCAA TAGGGACTTT  420
CCATTGACGT CAATGGGTGG ACTATTTACG GTAAACTGCC CACTTGGCAG TACATCAAGT  480
GTATCATATG CCAAGTACGC CCCCTATTGA CGTCAATGAC GGTAAATGGC CCGCCTGGCA  540
TTATGCCCAG TACATGACCT TATGGGACTT TCCTACTTGG CAGTACATCT ACGTATTAGT  600
CATCGCTATT ACCATGGTGA TGCGGTTTTG GCAGTACATC AATGGGCGTG GATAGCGGTT  660
TGACTCACGG GGATTTCCAA GTCTCCACCC CATTGACGTC AATGGGAGTT TGTTTTGAAG  720
CTTGGCCGGC CATATAAACG GCGGCCAGCT TTATTTAACG TGTTTACGTC GAGTCAATTG  780
TACACTAACG ACAGTGATGA AAGAAATACA AAAGCGCATA ATATTTTGAA CGACGTCGAA  840
```

FIG. 8B

CCTTTATTAC AAAACAAAAC ACAAACGAAT ATCGACAAAG CTAGATTGCT GCTACAAGAT 900
TTGGCAAGTT TTGTGGCGTT GAGCGAAAAT CCATTAGATA GTCCAGCCAT CGGTTCGGAA 960
AAACAACCCT TGTTTGAAAC TAATCGAAAC CTATTTTACA AATCTATTGA GGATTTAATA 1020
TTTAAATTCA GATATAAAGA CGCTGAAAAT CATTTGATTT TCGCTCTAAC ATACCACCCT 1080
AAAGATTATA AATTTAATGA ATTATTAAAA TACATCAGCA ACTATATATT GATAGACATT 1140
TCCAGTTTGT GATATTAGTT TGTGCGTCTC ATTACAATGG CTGTTATTTT TAACAACAAA 1200
CAACTGCTCG CAGACAATAG TATAGAAAAG GGAGGTGAAC TGTTTTTGTT TAACGGTTCG 1260
TACAACATTT TGGAAAGTTA TGTTAATCCG GTGCTGCTAA AAAATGGTGT AATTGAACTA 1320
GAAGAAGCTG CGTACTATGC CGGCAACATA TTGTACAAAA CCGACGATCC CAAATTCATT 1380
GATTATATAA ATTTAATAAT TAAAGCAACA CACTCCGAAG AACTACCAGA AAATAGCACT 1440
GTTGTAAATT ACAGAAAAAC TATGCGCAGC GGTACTATAC ACCCCATTAA AAAAGACATA 1500
TATATTTATG ACAACAAAAA ATTTACTCTA TACGATAGAT ACATATATGG ATACGATAAT 1560
AACTATGTTA ATTTTTATGA GGAGAAAAAT GAAAAAGAGA AGGAATACGA AGAAGAAGAC 1620
GACAAGGCGT CTAGTTTATG TGAAAATAAA ATTATATTGT CGCAAATTAA CTGTGAATCA 1680

FIG. 8C

```
TTTGAAAATG ATTTTAAATA TTACCTCAGC GATTATAACT ACGCGTTTTC AATTATAGAT 1740
AATACTACAA ATGTTCTTGT TGCGTTTGGT TTGTATCGTT AATAAAAAAC AAATTTAGCA 1800
TTTATAATTG TTTTATTATT CAATAATTAC AAATAGGATT GAGACCCTTG CAGTTGCCAG 1860
CAAACGGACA GAGCTTGTCG AGGAGAGTTG TTGATTCATT GTTTGCCTCC CTGCTGCGGT 1920
TTTTCACCGA AGTTCATGCC AGTCCAGCGT TTTTGCAGCA GAAAAGCCGC CGACTTCGGT 1980
TTGCGGTCGC GAGTGAAGAT CCCTTTCTTG TTACCGCCAA CGCGCAATAT GCCTTGCGAG 2040
GTCGCAAAAT CGGCGAAATT CCATACCTGT TCACCGACGA CGGCGCTGAC GCGATCAAAG 2100
ACGCGGTGAT ACATATCCAG CCATGCACAC TGATACTCTT CACTCCACAT GTCGGTGTAC 2160
ATTGAGTGCA GCCCGGCTAA CGTATCCACG CCGTATTCGG TGATGATAAT CGGCTGATGC 2220
AGTTTCTCCT GCCAGGCCAG AAGTTCTTTT TCCAGTACCT TCTCTGCCGT TTCCAAATCG 2280
CCGCTTTGGA CATACCATCC GTAATAACGG TTCAGGCACA GCACATCAAA GAGATCGCTG 2340
ATGGTATCGG TGTGAGCGTC GCAGAACATT ACATTGACGC AGGTGATCGG ACGCGTCGGG 2400
TCGAGTTTAC GCGTTGCTTC CGCCAGTGGC GCGAAATATT CCCGTGCACC TTGCGGACGG 2460
GTATCCGGTT CGTTGGCAAT ACTCCACATC ACCACGCTTG GGTGGTTTTT GTCACGCGCT 2520
```

FIG. 8D

ATCAGCTCTT TAATCGCCTG TAAGTGCGCT TGCTGAGTTT CCCCGTTGAC TGCCTCTTCG 2580
CTGTACAGTT CTTTCGGCTT GTTGCCCGCT TCGAAACCAA TGCCTAAAGA GAGGTTAAAG 2640
CCGACAGCAG CAGTTTCATC AATCACCACG ATGCCATGTT CATCTGCCCA GTCGAGCATC 2700
TCTTCAGCGT AAGGGTAATG CGAGGTACGG TAGGAGTTGG CCCCAATCCA GTCCATTAAT 2760
GCGTGGTCGT GCACCATCAG CACGTTATCG AATCCTTTGC CACGCAAGTC CGCATCTTCA 2820
TGACGACCAA AGCCAGTAAA GTAGAACGGT TTGTGGTTAA TCAGGAACTG TTCGCCCTTC 2880
ACTGCCACTG ACCGGATGCC GACGCGAAGC GGGTAGATAT CACACTCTGT CTGGCTTTTG 2940
GCTGTGACGC ACAGTTCATA GAGATAACCT TCACCCGGTT GCCAGAGGTG CGGATTCACC 3000
ACTTGCAAAG TCCCGCTAGT GCCTTGTCCA GTTGCAACCA CCTGTTGATC CGCATCACGC 3060
AGTTCAACGC TGACATCACC ATTGGCCACC ACCTGCCAGT CAACAGACGC GTGGTTACAG 3120
TCTTGCGCGA CATGCGTCAC CACGGTGATA TCGTCCACCC AGGTGTTCGG CGTGGTGTAG 3180
AGCATTACGC TGCGATGGAT TCCGGCATAG TTAAAGAAAT CATGGAAGTA AGACTGCTTT 3240
TTCTTGCCGT TTTCGTCGGT AATCACCATT CCCGGCGGGA TAGTCTGCCA GTTCAGTTCG 3300
TTGTTCACAC AAACGGTGAT ACCCCTCGAC GGATTAAAGA CTTCAAGCGG TCAACTATGA 3360

FIG. 8E

```
AGAAGTGTTC GTCTTCGTCC CAGTAAGCTA TGTCTCCAGA ATGTAGCCAT CCATCCTTGT 3420
CAATCAAGGC GTTGGTCGCT TCCGGATTGT TTACATAACC GGACATAATC ATAGGTCCTC 3480
TGACACATAA TTCGCCTCTC TGATTAACGC CCAGCGTTTT CCCGGTATCC AGATCCACAA 3540
CCTTCGCTTC AAAAAATGGA ACAACTTTAC CGACCGCGCC CGGTTTATCA TCCCCCTCGG 3600
GTGTAATCAG AATAGCTGAT GTAGTCTCAG TGAGCCCATA TCCTTGTCGT ATCCCTGGAA 3660
GATGGAAGCG TTTTGCAACC GCTTCCCCGA CTTCTTTCGA AAGAGGTGCG CCCCCAGAAG 3720
CAATTTCGTG TAAATTAGAT AAATCGTATT TGTCAATCAG AGTGCTTTTG GCGAAGAATG 3780
AAAATAGGGT TGGTACTAGC AACGCACTTT GAATTTTGTA ATCCTGAAGG GATCGTAAAA 3840
ACAGCTCTTC TTCAAATCTA TACATTAAGA CGACTCGAAA TCCACATATC AAATATCCGA 3900
GTGTAGTAAA CATTCCAAAA CCGTGATGGA ATGGAACAAC ACTTAAAATC GCAGTATCCG 3960
GAATGATTTG ATTGCCAAAA ATAGGATCTC TGGCATGCGA GAATCTAGCG CAGGCAGTTC 4020
TATGCGGAAG GGCCACACCC TTAGGTAACC CAGTAGATCC AGAGGAATTG TTTTGTCACG 4080
ATCAAAGGAC TCTGGTACAA AATCGTATTC ATTAAAACCG GGAGGTAGAT GAGATGTGAC 4140
GAACGTGTAC ATCGACTGAA ATCCCTGGTA ATCCGTTTTA GAATCCATGA TAATAATTTT 4200
```

FIG. 8F

CTGGATTATT GGTAATTTTT TTTGCACGTT CAAAATTTTT TGCAACCCCT TTTTGGAAAC 4260
AAACACTACG GTAGGCTGCG AAATGTTCAT ACTGTTGAGC AATTCACGTT CATTATAAAT 4320
GTCGTTCGCG GGCGCAACTG CAACTCCGAT AAATAACGCG CCCAACACCG GCATAAAGAA 4380
TTGAAGAGAG TTTTCACTGC ATACGACGAT TCTGTGATTT GTATTCAGCC CATATCGTTT 4440
CATAGCTTCT GCCAACCGAA CGGACATTTC GAAGTATTCC GCGTACGTGA TGTTCACCTC 4500
GATATGTGCA TCTGTAAAAG GAATTGTTCC AGGAACCAGG GCGTATCTCT TCATAGCCTT 4560
ATGCAGTTGC TCTCCAGCGG TTCCATCCTC TAGCTTTGCT TCTCAATTTC TTATTTGCAT 4620
AATGAGAAAA AAAGGAAAAT TAATTTTAAC ACCAATTCAG TAGTTGATTG AGCAAATGCG 4680
TTGCCAAAAA GGATGCTTTA GAGACAGTGT TCTCTGCACA GATAAGGACA AACATTATTC 4740
AGAGGGAGTA CCCAGAGCTG AGACTCCTAA GCCAGTGAGT GGCACAGCAT TCTAGGGAGA 4800
AATATGCTTG TCATCACCGA AGCCTGATTC CGTAGAGCCA CACCTTGGTA AGGGCCAATC 4860
TGCTCACACA GGATAGAGAG GGCAGGAGCC AGGGCAGAGC ATATAAGGTG AGGTAGGATC 4920
AGTTGCTCCT CACATTTGCT TCTGACATAG TTGTGTTGGG AGCTTGGATC GATCCACCAT 4980
GGGCTTCAAT ACCCTGATTG ACTGGAACAG CTGTAGCCCT GAACAGCAGC GTGCGCTGCT 5040

FIG. 8G

GACGCGTCCG GCGATTTCCG CCTCTGACAG TATTACCCGG ACGGTCAGCG ATATTCTGGA 5100
TAATGTAAAA ACGCGCGGTG ACGATGCCCT GCGTGAATAC AGCGCTAAAT TTGATAAAAC 5160
AGAAGTGACA GCGCTACGCG TCACCCCTGA AGAGATCGCC GCCGCCGGCG CGCGTCTGAG 5220
CGACGAATTA AAACAGGCGA TGACCGCTGC CGTCAAAAAT ATTGAAACGT TCCATTCCGC 5280
GCAGACGCTA CCGCCTGTAG ATGTGGAAAC CCAGCCAGGC GTGCGTTGCC AGCAGGTTAC 5340
GCGTCCCGTC TCGTCTGTCG GTCTGTATAT TCCCGGCGGC TCGGCTCCGC TCTTCTCAAC 5400
GGTGCTGATG CTGGCGACGC CGGCGCGCAT TGCGGGATGC CAGAAGGTGG TTCTGTGCTC 5460
GCCGCCGCCC ATCGCTGATG AAATCCTCTA TGCGGCGCAA CTGTGTGGCG TGCAGGAAAT 5520
CTTTAACGTC GGCGGCGCGC AGGCGATTGC CGCTCTGGCC TTCGGCAGCG AGTCCGTACC 5580
GAAAGTGGAT AAAATTTTTG GCCCCGGCAA CGCCTTTGTA ACCGAAGCCA AACGTCAGGT 5640
CAGCCAGCGT CTCGACGGCG CGGCTATCGA TATGCCAGCC GGGCCGTCTG AAGTACTGGT 5700
GATCGCAGAC AGCGGCGCAA CACCGGATTT CGTCGCTTCT GACCTGCTCT CCCAGGCTGA 5760
GCACGGCCCG GATTCCCAGG TGATCCTGCT GACGCCTGAT GCTGACATTG CCCGCAAGGT 5820
GGCGGAGGCG GTAGAACGTC AACTGGCGGA ACTGCCGCGC GCGGACACCG CCCGGCAGGC 5880

FIG. 8H

CCTGAGCGCC AGTCGTCTGA TTGTGACCAA AGATTTAGCG CAGTGCGTCG CCATCTCTAA 5940
TCAGTATGGG CCGGAACACT TAATCATCCA GACGCGCAAT GCGCGCGATT TGGTGGATGC 6000
GATTACCAGC GCAGGCTCGG TATTTCTCGG CGACTGGTCG CCGGAATCCG CCGGTGATTA 6060
CGCTTCCGGA ACCAACCATG TTTTACCGAC CTATGGCTAT ACTGCTACCT GTTCCAGCCT 6120
TGGGTTAGCG GATTTCCAGA AACGGATGAC CGTTCAGGAA CTGTCGAAAG CGGGCTTTTC 6180
CGCTCTGGCA TCAACCATTG AAACATTGGC GGCGGCAGAA CGTCTGACCG CCCATAAAAA 6240
TGCCGTGACC CTGCGCGTAA ACGCCCTCAA GGAGCAAGCA TGAGCACTGA AAACACTCTC 6300
AGCGTCGCTG ACTTAGCCCG TGAAAATGTC CGCAACCTGG AGATCCAGAC ATGATAAGAT 6360
ACATTGATGA GTTTGGACAA ACCACAACTA GAATGCAGTG AAAAAAATGC TTTATTTGTG 6420
AAATTTGTGA TGCTATTGCT TTATTTGTAA CCATTATAAG CTGCAATAAA CAAGTTAACA 6480
ACAACAATTG CATTCATTTT ATGTTTCAGG TTCAGGGGGA GGTGTGGGAG GTTTTTTAAA 6540
GCAAGTAAAA CCTCTACAAA TGTGGTATGG CTGATTATGA TCTCTAGCTC GACGGCGCGC 6600
CTCTAGAGCA GTGTGGTTTT GCAAGAGGAA GCAAAAAGCC TCTCCACCCA GGCCTGGAAT 6660
GTTTCCACCC AATGTCGAGC AGTGTGGTTT TGCAAGAGGA AGCAAAAAGC CTCTCCACCC 6720

FIG. 8I

AGGCCTGGAA TGTTTCCACC CAATGTCGAG CAAACCCCGC CCAGCGTCTT GTCATTGGCG 6780
AATTCGAACA CGCAGATGCA GTCGGGGCGG CGCGGTCCCA GTCCCACTTC GCATATTAAG 6840
GTGACGCGTG TGGCCTCGAA CACCGAGCGA CCCTGCAGCC AATATGGGAT CGGCCATTGA 6900
ACAAGATGGA TTGCACGCAG GTTCTCCGGC CGCTTGGGTG GAGAGGCTAT TCGGCTATGA 6960
CTGGGCACAA CAGACAATCG GCTGCTCTGA TGCCGCCGTG TTCCGGCTGT CAGCGCAGGG 7020
GCGCCCGGTT CTTTTTGTCA AGACCGACCT GTCCGGTGCC CTGAATGAAC TGCAGGTAAG 7080
TGCGGCCGTC GATGGCCGAG GCGGCCTCGG CCTCTGCATA AATAAAAAAA ATTAGTCAGC 7140
CATGCATGGG GCGGAGAATG GGCGGAACTG GGCGGAGTTA GGGGCGGGAT GGGCGGAGTT 7200
AGGGGCGGGA CTATGGTTGC TGACTAATTG AGATGCATGC TTTGCATACT TCTGCCTGCT 7260
GGGGAGCCTG GGGACTTTCC ACACCTGGTT GCTGACTAAT TGAGATGCAT GCTTTGCATA 7320
CTTCTGCCTG CTGGGGAGCC TGGGGACTTT CCACACCCTA ACTGACACAC ATTCCACAGA 7380
ATTAATTCCC CTAGTTATTA ATAGTAATCA ATTACGGGGT CATTAGTTCA TAGCCCATAT 7440
ATGGAGTTCC GCGTTACATA ACTTACGGTA AATGGCCCGC CTGGCTGACC GCCCAACGAC 7500
CCCCGCCCAT TGACGTCAAT AATGACGTAT GTTCCCATAG TAACGCCAAT AGGGACTTTC 7560

FIG. 8J

```
CATTGACGTC AATGGGTGGA CTATTTACGG TAAACTGCCC ACTTGGCAGT ACATCAAGTG  7620
TATCATATGC CAAGTACGCC CCCTATTGAC GTCAATGACG GTAAATGGCC CGCCTGGCAT  7680
TATGCCCAGT ACATGACCTT ATGGGACTTT CCTACTTGGC AGTACATCTA GCTATTAGTC  7740
ATCGCTATTA CCATGGTGAT GCGGTTTTGG CAGTACATCA ATGGGCGTGG ATAGCGGTTT  7800
GACTCACGGG GATTTCCAAG TCTCCACCCC ATTGACGTCA ATGGGAGTTT GTTTTGGCAC  7860
CAAAATCAAC GGGACTTTCC AAAATGTCGT AACAACTCCG CCCCATTGAC GCAAATGGGC  7920
GGTAGGCGTG TACGGTGGGA GGTCTATATA AGCAGAGCTG GGTACGTGAA CCGTCAGATC  7980
GCCTGGAGAC GCCATCACAG ATCTCTCACT ATGGATTTTC AGGTGCAGAT TATCAGCTTC  8040
CTGCTAATCA GTGCTTCAGT CATAATGTCC AGAGGACAAA TTGTTCTCTC CCAGTCTCCA  8100
GCAATCCTGT CTGCATCTCC AGGGGAGAAG GTCACAATGA CTTGCAGGGC CAGCTCAAGT  8160
GTAAGTTACA TCCACTGGTT CCAGCAGAAG CCAGGATCCT CCCCCAAACC CTGGATTTAT  8220
GCCACATCCA ACCTGGCTTC TGGAGTCCCT GTTCGCTTCA GTGGCAGTGG GTCTGGGACT  8280
TCTTACTCTC TCACAATCAG CAGAGTGGAG GCTGAAGATG CTGCCACTTA TTACTGCCAG  8340
CAGTGGACTA GTAACCCACC CACGTTCGGA GGGGGGACCA AGCTGGAAAT CAAACGTACG  8400
```

FIG. 8K

GTGGCTGCAC CATCTGTCTT CATCTTCCCG CCATCTGATG AGCAGTTGAA ATCTGGAACT 8460
GCCTCTGTTG TGTGCCTGCT GAATAACTTC TATCCCAGAG AGGCCAAAGT ACAGTGGAAG 8520
GTGGATAACG CCCTCCAATC GGGTAACTCC CAGGAGAGTG TCACAGAGCA GGACAGCAAG 8580
GACAGCACCT ACAGCCTCAG CAGCACCCTG ACGCTGAGCA AAGCAGACTA CGAGAAACAC 8640
AAAGTCTACG CCTGCGAAGT CACCCATCAG GGCCTGAGCT CGCCCGTCAC AAAGAGCTTC 8700
AACAGGGGAG AGTGTTGAAT TCAGATCCGT TAACGGTTAC CAACTACCTA GACTGGATTC 8760
GTGACAACAT GCGGCCGTGA TATCTACGTA TGATCAGCCT CGACTGTGCC TTCTAGTTGC 8820
CAGCCATCTG TTGTTTGCCC CTCCCCCGTG CCTTCCTTGA CCCTGGAAGG TGCCACTCCC 8880
ACTGTCCTTT CCTAATAAAA TGAGGAAATT GCATCGCATT GTCTGAGTAG GTGTCATTCT 8940
ATTCTGGGGG GTGGGGTGGG GCAGGACAGC AAGGGGGAGG ATTGGGAAGA CAATAGCAGG 9000
CATGCTGGGG ATGCGGTGGG CTCTATGGAA CCAGCTGGGG CTCGACAGCT ATGCCAAGTA 9060
CGCCCCCTAT TGACGTCAAT GACGGTAAAT GGCCCGCCTG GCATTATGCC CAGTACATGA 9120
CCTTATGGGA CTTTCCTACT TGGCAGTACA TCTACGTATT AGTCATCGCT ATTACCATGG 9180
TGATGCGGTT TTGGCAGTAC ATCAATGGGC GTGGATAGCG GTTTGACTCA CGGGGATTTC 9240

FIG. 8L

CAAGTCTCCA CCCCATTGAC GTCAATGGGA GTTTGTTTTG GCACCAAAAT CAACGGGACT 9300
TTCCAAAATG TCGTAACAAC TCCGCCCCAT TGACGCAAAT GGGCGGTAGG CGTGTACGGT 9360
GGGAGGTCTA TATAAGCAGA GCTGGGTACG TCCTCACATT CAGTGATCAG CACTGAACAC 9420
AGACCCGTCG ACATGGGTTG GAGCCTCATC TTGCTCTTCC TTGTCGCTGT TGCTACGCGT 9480
GTCCTGTCCC AGGTACAACT GCAGCAGCCT GGGGCTGAGC TGGTGAAGCC TGGGGCCTCA 9540
GTGAAGATGT CCTGCAAGGC TTCTGGCTAC ACATTTACCA GTTACAATAT GCACTGGGTA 9600
AAACAGACAC CTGGTCGGGG CCTGGAATGG ATTGGAGCTA TTTATCCCGG AAATGGTGAT 9660
ACTTCCTACA ATCAGAAGTT CAAAGGCAAG GCCACATTGA CTGCAGACAA ATCCTCCAGC 9720
ACAGCCTACA TGCAGCTCAG CAGCCTGACA TCTGAGGACT CTGCGGTCTA TTACTGTGCA 9780
AGATCGACTT ACTACGGCGG TGACTGGTAC TTCAATGTCT GGGGCGCAGG GACCACGGTC 9840
ACCGTCTCTG CAGCTAGCAC CAAGGGCCCA TCGGTCTTCC CCCTGGCACC CTCCTCCAAG 9900
AGCACCTCTG GGGGCACAGC GGCCCTGGGC TGCCTGGTCA AGGACTACTT CCCCGAACCG 9960
GTGACGGTGT CGTGGAACTC AGGCGCCCTG ACCAGCGGCG TGCACACCTT CCCGGCTGTC 10020
CTACAGTCCT CAGGACTCTA CTCCCTCAGC AGCGTGGTGA CCGTGCCCTC CAGCAGCTTG 10080

FIG. 8M

GGCACCCAGA CCTACATCTG CAACGTGAAT CACAAGCCCA GCAACACCAA GGTGGACAAG 10140
AAAGCAGAGC CCAAATCTTG TGACAAAACT CACACATGCC CACCGTGCCC AGCACCTGAA 10200
CTCCTGGGGG GACCGTCAGT CTTCCTCTTC CCCCCAAAAC CCAAGGACAC CCTCATGATC 10260
TCCCGGACCC CTGAGGTCAC ATGCGTGGTG GTGGACGTGA GCCACGAAGA CCCTGAGGTC 10320
AAGTTCAACT GGTACGTGGA CGGCGTGGAG GTGCATAATG CCAAGACAAA GCCGCGGGAG 10380
GAGCAGTACA ACAGCACGTA CCGTGTGGTC AGCGTCCTCA CCGTCCTGCA CCAGGACTGG 10440
CTGAATGGCA AGGAGTACAA GTGCAAGGTC TCCAACAAAG CCCTCCCAGC CCCCATCGAG 10500
AAAACCATCT CCAAAGCCAA AGGGCAGCCC CGAGAACCAC AGGTGTACAC CCTGCCCCCA 10560
TCCCGGGATG AGCTGACCAA GAACCAGGTC AGCCTGACCT GCCTGGTCAA AGGCTTCTAT 10620
CCCAGCGACA TCGCCGTGGA GTGGGAGAGC AATGGGCAGC CGGAGAACAA CTACAAGACC 10680
ACGCCTCCCG TGCTGGACTC CGACGGCTCC TTCTTCCTCT ACAGCAAGCT CACCGTGGAC 10740
AAGAGCAGGT GGCAGCAGGG GAACGTCTTC TCATGCTCCG TGATGCATGA GGCTCTGCAC 10800
AACCACTACA CGCAGAAGAG CCTCTCCCTG TCTCCGGGTA AATGAGGATC CGTTAACGGT 10860
TACCAACTAC CTAGACTGGA TTCGTGACAA CATGCGGCCG TGATATCTAC GTATGATCAG 10920

FIG. 8N

CCTCGACTGT GCCTTCTAGT TGCCAGCCAT CTGTTGTTTG CCCCTCCCCC GTGCCTTCCT 10980
TGACCCTGGA AGGTGCCACT CCCACTGTCC TTTCCTAATA AAATGAGGAA ATTGCATCGC 11040
ATTGTCTGAG TAGGTGTCAT TCTATTCTGG GGGGTGGGGT GGGGCAGGAC AGCAAGGGGG 11100
AGGATTGGGA AGACAATAGC AGGCATGCTG GGGATGCGGT GGGCTCTATG GAACCAGCTG 11160
GGGCTCGACA GCAACGCTAG GTCGAGGCCG CTACTAACTC TCTCCTCCCT CCTTTTTCCT 11220
GCAGGACGAG GCAGCGCGGC TATCGTGGCT GGCCACGACG GGCGTTCCTT GCGCAGCTGT 11280
GCTCGACGTT GTCACTGAAG CGGGAAGGGA CTGGCTGCTA TTGGGCGAAG TGCCGGGGCA 11340
GGATCTCCTG TCATCTCACC TTGCTCCTGC CGAGAAAGTA TCCATCATGG CTGATGCAAT 11400
GCGGCGGCTG CATACGCTTG ATCCGGCTAC CTGCCCATTC GACCACCAAG CGAAACATCG 11460
CATCGAGCGA GCACGTACTC GGATGGAAGC CGGTCTTGTC GATCAGGATG ATCTGGACGA 11520
AGAGCATCAG GGGCTCGCGC CAGCCGAACT GTTCGCCAGG TAAGTGAGCT CCAATTCAAG 11580
CTTCCTAGGG CGGCCAGCTA GTAGCTTTGC TTCTCAATTT CTTATTTGCA TAATGAGAAA 11640
AAAAGGAAAA TTAATTTTAA CACCAATTCA GTAGTTGATT GAGCAAATGC GTTGCCAAAA 11700
AGGATGCTTT AGAGACAGTG TTCTCTGCAC AGATAAGGAC AAACATTATT CAGAGGGAGT 11760

FIG. 8P

ACCCAGAGCT GAGACTCCTA AGCCAGTGAG TGGCACAGCA TTCTAGGGAG AAATATGCTT 11820
GTCATCACCG AAGCCTGATT CCGTAGAGCC ACACCTTGGT AAGGGCCAAT CTGCTCACAC 11880
AGGATAGAGA GGGCAGGAGC CAGGGCAGAG CATATAAGGT GAGGTAGGAT CAGTTGCTCC 11940
TCACATTTGC TTCTGACATA GTTGTGTTGG GAGCTTGGAT AGCTTGGACA GCTCAGGGCT 12000
GCGATTTCGC GCCAAACTTG ACGGCAATCC TAGCGTGAAG GCTGGTAGGA TTTTATCCCC 12060
GCTGCCATCA TGGTTCGACC ATTGAACTGC ATCGTCGCCG TGTCCCAAAA TATGGGGATT 12120
GGCAAGAACG GAGACCTACC CTGGCCTCCG CTCAGGAACG AGTTCAAGTA CTTCCAAAGA 12180
ATGACCACAA CCTCTTCAGT GGAAGGTAAA CAGAATCTGG TGATTATGGG TAGGAAAACC 12240
TGGTTCTCCA TTCCTGAGAA GAATCGACCT TTAAAGGACA GAATTAATAT AGTTCTCAGT 12300
AGAGAACTCA AAGAACCACC ACGAGGAGCT CATTTTCTTG CCAAAAGTTT GGATGATGCC 12360
TTAAGACTTA TTGAACAACC GGAATTGGCA AGTAAAGTAG ACATGGTTTG GATAGTCGGA 12420
GGCAGTTCTG TTTACCAGGA AGCCATGAAT CAACCAGGCC ACCTTAGACT CTTTGTGACA 12480
AGGATCATGC AGGAATTTGA AAGTGACACG TTTTTCCCAG AAATTGATTT GGGGAAATAT 12540
AAACTTCTCC CAGAATACCC AGGCGTCCTC TCTGAGGTCC AGGAGGAAAA AGGCATCAAG 12600

FIG. 8Q

TATAAGTTTG AAGTCTACGA GAAGAAAGAC TAACAGGAAG ATGCTTTCAA GTTCTCTGCT 12660
CCCCTCCTAA AGCTATGCAT TTTTATAAGA CCATGGGACT TTTGCTGGCT TTAGATCAGC 12720
CTCGACTGTG CCTTCTAGTT GCCAGCCATC TGTTGTTTGC CCCTCCCCCG TGCCTTCCTT 12780
GACCCTGGAA GGTGCCACTC CCACTGTCCT TTCCTAATAA AATGAGGAAA TTGCATCGCA 12840
TTGTCTGAGT AGGTGTCATT CTATTCTGGG GGGTGGGGTG GGGCAGGACA GCAAGGGGGA 12900
GGATTGGGAA GACAATAGCA GGCATGCTGG GGATGCGGTG GGCTCTATGG AACCAGCTGG 12960
GGCTCGAAGC GGCCGCCCAT TTCGCTGGTG GTCAGATGCG GGATGGCGTG GGACGCGGCG 13020
GGGAGCGTCA CACTGAGGTT TTCCGCCAGA CGCCACTGCT GCCAGGCGCT GATGTGCCCG 13080
GCTTCTGACC ATGCGGTCGC GTTCGGTTGC ACTACGCGTA CTGTGAGCCA GAGTTGCCCG 13140
GCGCTCTCCG GCTGCGGTAG TTCAGGCAGT TCAATCAACT GTTTACCTTG TGGACCGACA 13200
TCCAGAGGCA CTTCACCGCT TGCCAGCGGC TTACCATCCA GCGCCACCAT CCAGTGCAGG 13260
AGCTCGTTAT CGCTATGACG GAACAGGTAT TCGCTGGTCA CTTCGATGGT TTGCCCGGAT 13320
AAACGGAACT GGAAAAACTG CTGCTGGTGT TTTGCTTCCG TCAGCGCTGG ATGCGGCGTG 13380
CGGTCGGCAA AGACCAGACC GTTCATACAG AACTGGCGAT CGTTCGGCGT ATCGCCAAAA 13440

FIG. 8R

TCACCGCCGT AAGCCGACCA CGGGTTGCCG TTTTCATCAT ATTTAATCAG CGACTGATCC 13500
ACCCAGTCCC AGACGAAGCC GCCCTGTAAA CGGGGATACT GACGAAACGC CTGCCAGTAT 13560
TTAGCGAAAC CGCCAAGACT GTTACCCATC GCTGGGGCGT ATTCGCAAAG GATCAGCGGG 13620
CGCGTCTCTC CGGGTAGCGA AAGCCATTTT TTGATGGACC ATTTCGGACC AGCCGGGAAG 13680
GGCTGGTCTT CATCCACGCG CGCGTACATC GGGCAAATAA TATCGGTGGC CGTGGTGTCG 13740
GCTCCGCCGC CTTCATACTG CACCGGGCGG GAAGGATCGA CAGATTTGAT CCAGCGATAC 13800
AGCGCGTCGT GATTAGCGCC GTGGCCTGAT TCATTCCCCA GCGACCAGAT GATCACACTC 13860
GGGTGATTAC GATCGCGCTG CACCATTCGC GTTACGCGTT CGCTCATCGC CGGTAGCCAG 13920
CGCGGATCAT CGGTCAGACG ATTCATTGGC ACCATGCCGT GGGTTTCAAT ATTGGCTTCA 13980
TCCACCACAT ACAGGCCGTA GCGGTCGCAC AGCGTGTACC ACAGCGGATG GTTCGGATAA 14040
TGCCAACAGC GCACGGCGTT AAAGTTGTTC TGCTTCATCA GCAGGATATC CTGCACCATC 14100
GTCTGCTCAT CCATGACCTG ACCATGCAGA GGATGATGCT CGTGACGGTT AACGCCTCGA 14160
ATCAGCAACG GCTTGCCGTT CAGCAGCAGC AGACCATTTT CAATCCGCAC CTCGCGGAAA 14220
CCGACATCGC AGGCTTCTGC TTCAATCAGC GTGCCGTCGG CGGTGTGCAG TTCAACCACC 14280

FIG. 8S

GCACGATAGA GATTCGGGAT TTCGGCGCTC CACAGTTTCG GGTTTTCGAC GTTCAGACGC 14340
AGTGTGACGC GATCGGCATA ACCACCACGC TCATCGATAA TTTCACCGCC GAAAGGCGCG 14400
GTGCCGCTGG CGACCTGCGT TTCACCCTGC CATAAAGAAA CTGTTACCCG TAGGTAGTCA 14460
CGCAACTCGC CGCACATCTG AACTTCAGCC TCCAGTACAG CGCGGCTGAA ATCATCATTA 14520
AAGCGAGTGG CAACATGGAA ATCGCTGATT TGTGTAGTCG GTTTATGCAG CAACGAGACG 14580
TCACGGAAAA TGCCGCTCAT CCGCCACATA TCCTGATCTT CCAGATAACT GCCGTCACTC 14640
CAACGCAGCA CCATCACCGC GAGGCGGTTT TCTCCGGCGC GTAAAAATGC GCTCAGGTCA 14700
AATTCAGACG GCAAACGACT GTCCTGGCCG TAACCGACCC ACGCCCCGTT GCACCACAGA 14760
TGAAACGCCG AGTTAACGCC ATCAAAAATA ATTCGCGTCT GGCCTTCCTG TAGCCAGCTT 14820
TCATCAACAT TAAATGTGAG CGAGTAACAA CCCGTCGGAT TCTCCGTGGG AACAAACGGC 14880
GGATTGACCG TAATGGGATA GGTTACGTTG GTGTAGATGG GCGCATCGTA ACCGTGCATC 14940
TGCCAGTTTG AGGGGACGAC GACAGTATCG GCCTCAGGAA GATCGCACTC CAGCCAGCTT 15000
TCCGGCACCG CTTCTGGTGC CGGAAACCAG GCAAAGCGCC ATTCGCCATT CAGGCTGCGC 15060
AACTGTTGGG AAGGGCGATC GGTGCGGGCC TCTTCGCTAT TACGCCAGCT GGCGAAAGGG 15120

FIG. 8T

```
GGATGTGCTG CAAGGCGATT AAGTTGGGTA ACGCCAGGGT TTTCCCAGTC ACGACGTTGT 15180
AAAACGACTT AATCCGTCGA GGGGCTGCCT CGAAGCAGAC GACCTTCCGT TGTGCAGCCA 15240
GCGGCGCCTG CGCCGGTGCC CACAATCGTG CGCGAACAAA CTAAACCAGA ACAAATTATA 15300
CCGGCGGCAC CGCCGCCACC ACCTTCTCCC GTGCCTAACA TTCCAGCGCC TCCACCACCA 15360
CCACCACCAT CGATGTCTGA ATTGCCGCCC GCTCCACCAA TGCCGACGGA ACCTCAACCC 15420
GCTGCACCTT TAGACGACAG ACAACAATTG TTGGAAGCTA TTAGAAACGA AAAAAATCGC 15480
ACTCGTCTCA GACCGGTCAA ACCAAAAACG GCGCCCGAAA CCAGTACAAT AGTTGAGGTG 15540
CCGACTGTGT TGCCTAAAGA GACATTTGAG CCTAAACCGC CGTCTGCATC ACCGCCACCA 15600
CCTCCGCCTC CGCCTCCGCC GCCAGCCCCG CCTGCGCCTC CACCGATGGT AGATTTATCA 15660
TCAGCTCCAC CACCGCCGCC ATTAGTAGAT TTGCCGTCTG AAATGTTACC ACCGCCTGCA 15720
CCATCGCTTT CTAACGTGTT GTCTGAATTA AAATCGGGCA CAGTTAGATT GAAACCCGCC 15780
CAAAAACGCC CGCAATCAGA AATAATTCCA AAAAGCTCAA CTACAAATTT GATCGCGGAC 15840
GTGTTAGCCG ACACAATTAA TAGGCGTCGT GTGGCTATGG CAAAATCGTC TTCGGAAGCA 15900
ACTTCTAACG ACGAGGGTTG GGACGACGAC GATAATCGGC CTAATAAAGC TAACACGCCC 15960
```

FIG. 8U

GATGTTAAAT ATGTCCAAGC TACTAGTGGT ACCGCTTGGC AGAACATATC CATCGCGTCC 16020
GCCATCTCCA GCAGCCGCAC GCGGCGCATC TCGGGCAGCG TTGGGTCCTG GCCACGGGTG 16080
CGCATGATCG TGCTCCTGTC GTTGAGGACC CGGCTAGGCT GGCGGGGTTG CCTTACTGGT 16140
TAGCAGAATG AATCACCGAT ACGCGAGCGA ACGTGAAGCG ACTGCTGCTG CAAAACGTCT 16200
GCGACCTGAG CAACAACATG AATGGTCTTC GGTTTCCGTG TTTCGTAAAG TCTGGAAACG 16260
CGGAAGTCAG CGCCCTGCAC CATTATGTTC CGGATCTGCA TCGCAGGATG CTGCTGGCTA 16320
CCCTGTGGAA CACCTACATC TGTATTAACG AAGCGCTGGC ATTGACCCTG AGTGATTTTT 16380
CTCTGGTCCC GCCGCATCCA TACCGCCAGT TGTTTACCCT CACAACGTTC CAGTAACCGG 16440
GCATGTTCAT CATCAGTAAC CCGTATCGTG AGCATCCTCT CTCGTTTCAT CGGTATCATT 16500
ACCCCCATGA ACAGAAATCC CCCTTACACG GAGGCATCAG TGACCAAACA GGAAAAAACC 16560
GCCCTTAACA TGGCCCGCTT TATCAGAAGC CAGACATTAA CGCTTCTGGA GAAACTCAAC 16620
GAGCTGGACG CGGATGAACA GGCAGACATC TGTGAATCGC TTCACGACCA CGCTGATGAG 16680
CTTTACCGCA GCTGCCTCGC GCGTTTCGGT GATGACGGTG AAAACCTCTG ACACATGCAG 16740
CTCCCGGAGA CGGTCACAGC TTGTCTGTAA GCGGATGCCG GGAGCAGACA AGCCCGTCAG 16800

FIG. 8V

GGCGCGTCAG CGGGTGTTGG CGGGTGTCGG GGCGCAGCCA TGACCCAGTC ACGTAGCGAT 16860
AGCGGAGTGT ATACTGGCTT AACTATGCGG CATCAGAGCA GATTGTACTG AGAGTGCACC 16920
ATATGCGGTG TGAAATACCG CACAGATGCG TAAGGAGAAA ATACCGCATC AGGCGCTCTT 16980
CCGCTTCCTC GCTCACTGAC TCGCTGCGCT CGGTCGTTCG GCTGCGGCGA GCGGTATCAG 17040
CTCACTCAAA GGCGGTAATA CGGTTATCCA CAGAATCAGG GGATAACGCA GGAAAGAACA 17100
TGTGAGCAAA AGGCCAGCAA AAGGCCAGGA ACCGTAAAAA GGCCGCGTTG CTGGCGTTTT 17160
TCCATAGGCT CCGCCCCCCT GACGAGCATC ACAAAAATCG ACGCTCAAGT CAGAGGTGGC 17220
GAAACCCGAC AGGACTATAA AGATACCAGG CGTTTCCCCC TGGAAGCTCC CTCGTGCGCT 17280
CTCCTGTTCC GACCCTGCCG CTTACCGGAT ACCTGTCCGC CTTTCTCCCT TCGGGAAGCG 17340
TGGCGCTTTC TCATAGCTCA CGCTGTAGGT ATCTCAGTTC GGTGTAGGTC GTTCGCTCCA 17400
AGCTGGGCTG TGTGCACGAA CCCCCCGTTC AGCCCGACCG CTGCGCCTTA TCCGGTAACT 17460
ATCGTCTTGA GTCCAACCCG GTAAGACACG ACTTATCGCC ACTGGCAGCA GCCACTGGTA 17520
ACAGGATTAG CAGAGCGAGG TATGTAGGCG GTGCTACAGA GTTCTTGAAG TGGTGGCCTA 17580
ACTACGGCTA CACTAGAAGG ACAGTATTTG GTATCTGCGC TCTGCTGAAG CCAGTTACCT 17640

FIG. 8W

```
TCGGAAAAAG AGTTGGTAGC TCTTGATCCG GCAAACAAAC CACCGCTGGT AGCGGTGGTT 17700
TTTTTGTTTG CAAGCAGCAG ATTACGCGCA GAAAAAAAGG ATCTCAAGAA GATCCTTTGA 17760
TCTTTTCTAC GGGGTCTGAC GCTCAGTGGA ACGAAAACTC ACGTTAAGGG ATTTTGGTCA 17820
TGAGATTATC AAAAAGGATC TTCACCTAGA TCCTTTTAAA TTAAAAATGA AGTTTTAAAT 17880
CAATCTAAAG TATATATGAG TAAACTTGGT CTGACAGTTA CCAATGCTTA ATCAGTGAGG 17940
CACCTATCTC AGCGATCTGT CTATTTCGTT CATCCATAGT TGCCTGACTC CCCGTCGTGT 18000
AGATAACTAC GATACGGGAG GGCTTACCAT CTGGCCCCAG TGCTGCAATG ATACCGCGAG 18060
ACCCACGCTC ACCGGCTCCA GATTTATCAG CAATAAACCA GCCAGCCGGA AGGGCCGAGC 18120
GCAGAAGTGG TCCTGCAACT TTATCCGCCT CCATCCAGTC TATTAATTGT TGCCGGGAAG 18180
CTAGAGTAAG TAGTTCGCCA GTTAATAGTT TGCGCAACGT TGTTGCCATT GCTGCAGGCA 18240
TCGTGGTGTC ACGCTCGTCG TTTGGTATGG CTTCATTCAG CTCCGGTTCC CAACGATCAA 18300
GGCGAGTTAC ATGATCCCCC ATGTTGTGCA AAAAAGCGGT TAGCTCCTTC GGTCCTCCGA 18360
TCGTTGTCAG AAGTAAGTTG GCCGCAGTGT TATCACTCAT GGTTATGGCA GCACTGCATA 18420
ATTCTCTTAC TGTCATGCCA TCCGTAAGAT GCTTTTCTGT GACTGGTGAG TACTCAACCA 18480
```

FIG. 8X

AGTCATTCTG AGAATAGTGT ATGCGGCGAC CGAGTTGCTC TTGCCCGGCG TCAACACGGG 18540
ATAATACCGC GCCACATAGC AGAACTTTAA AAGTGCTCAT CATTGGAAAA CGTTCTTCGG 18600
GGCGAAAACT CTCAAGGATC TTACCGCTGT TGAGATCCAG TTCGATGTAA CCCACTCGTG 18660
CACCCAACTG ATCTTCAGCA TCTTTTACTT TCACCAGCGT TTCTGGGTGA GCAAAAACAG 18720
GAAGGCAAAA TGCCGCAAAA AAGGGAATAA GGGCGACACG GAAATGTTGA ATACTCATAC 18780
TCTTCCTTTT TCAATATTAT TGAAGCATTT ATCAGGGTTA TTGTCTCATG AGCGGATACA 18840
TATTTGAATG TATTTAGAAA AATAAACAAA TAGGGGTTCC GCGCACATTT CCCCGAAAAG 18900
TGCCACCTGA CGTCTAAGAA ACCATTATTA TCATGACATT AACCTATAAA AATAGGCGTA 18960
TCACGAGGCC CTTTCGTCTT CAAGAA 18986

FIG. 9

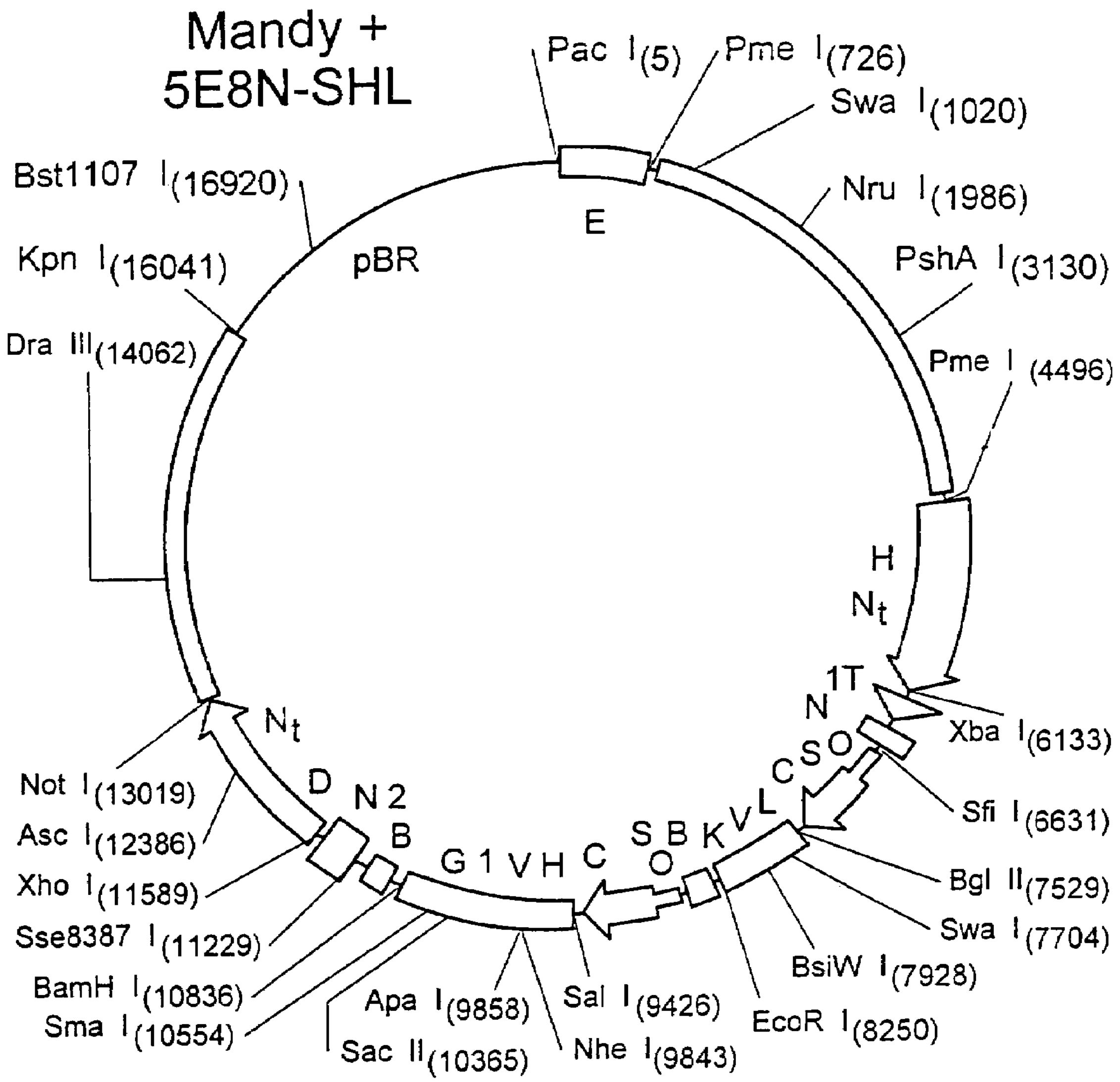

Nt D = Inactive Dihydrofolate reductase
E = CMV and SV40 enhancers
Nt H = Inactive Samonella Histidinol Dehydrogenase
T = Herpes Simplex thymidine kinas promoter and polyoma enhancer
C = Cytomegalovirus promoter/enhancer
N1 = Neomycin phosphotransferase exon 1
K = Human kappa constant
VL = Variable light chain anti-CD23 primate 5E8 and leader
VH = Variable heavy chain anti-CD-23 primate 5E8N- and leader
B = Bovine growth hormone polyadenylation
M2 = Neomycin phosphotransferase exon 2
G1 = Human Gamma 1 constant
Mandy cut XbaI Xho I and ligated to Xba I Xho I fragment
from XKG1+CD23 5E8N-SHL
Map by Mitchell Reff Constructed by Karen McLachlan 06/26/97 19,035 bp
Noncutters = AflII, AvrII, HindIII, I-PpoI, I-SceI, PmlI, RsrII, SgfI, SrfI

| | | | | | | |
|---|---|---|---|---|---|---|
| 10 | 20 | 30 | 40 | 50 | 60 | 70 |
| TTAATTAAGG | GGCGGAGAAT | GGGCGGAACT | GGGCGGAGTT | AGGGGCGGGA | TGGGCGGAGT | TAGGGGCGGG |
| 80 | 90 | 100 | 110 | 120 | 130 | 140 |
| ACTATGGTTG | CTGACTAATT | GAGATGCATG | CTTTGCATAC | TTCTGCCTGC | TGGGGAGCCT | GGGGACTTTC |
| 150 | 160 | 170 | 180 | 190 | 200 | 210 |
| CACACCTGGT | TGCTGACTAA | TTGAGATGCA | TGCTTTGCAT | ACTTCTGCCT | GCTGGGGAGC | CTGGGGACTT |
| 220 | 230 | 240 | 250 | 260 | 270 | 280 |
| TCCACACCCT | AACTGACACA | CATTCCACAG | AATTAATTCC | CCTAGTTATT | AATAGTAATC | AATTACGGGG |
| 290 | 300 | 310 | 320 | 330 | 340 | 350 |
| TCATTAGTTC | ATAGCCCATA | TATGGAGTTC | CGCGTTACAT | AACTTACGGT | AAATGGCCCG | CCTGGCTGAC |
| 360 | 370 | 380 | 390 | 400 | 410 | 420 |
| CGCCCAACGA | CCCCCGCCCA | TTGACGTCAA | TAATGACGTA | TGTTCCCATA | GTAACGCCAA | TAGGGACTTT |
| 430 | 440 | 450 | 460 | 470 | 480 | 490 |
| CCATTGACGT | CAATGGGTGG | AGTATTTACG | GTAAACTGCC | CACTTGGCAG | TACATCAAGT | GTATCATATG |
| 500 | 510 | 520 | 530 | 540 | 550 | 560 |
| CCAAGTACGC | CCCCTATTGA | CGTCAATGAC | GGTAAATGGC | CCGCCTGGCA | TTATGCCCAG | TACATGACCT |
| 570 | 580 | 590 | 600 | 610 | 620 | 630 |
| TATGGGACTT | TCCTACTTGG | CAGTACATCT | ACGTATTAGT | CATCGCTATT | ACCATGGTGA | TGCGGTTTTG |
| 640 | 650 | 660 | 670 | 680 | 690 | 700 |
| GCAGTACATC | AATGGGCGTG | GATAGCGGTT | TGACTCACGG | GGATTTCCAA | GTCTCCACCC | CATTGACGTC |
| 710 | 720 | 730 | 740 | 750 | 760 | 770 |
| AATGGGAGTT | TGTTTTGAAG | CTGTTTAAAC | AGCTTGGCCG | GCCAGCTTTA | TTTAACGTGT | TTACGTCGAG |
| 780 | 790 | 800 | 810 | 820 | 830 | 840 |
| TCAATTGTAC | ACTAACGACA | GTGATGAAAG | AAATACAAAA | GCGCATAATA | TTTTGAACGA | CGTCGAACCT |
| 850 | 860 | 870 | 880 | 890 | 900 | 910 |
| TTATTACAAA | ACAAAACACA | AACGAATATC | GACAAACCTA | GATTGCTGCT | ACAAGATTTG | GCAAGTTTTG |
| 920 | 930 | 940 | 950 | 960 | 970 | 980 |
| TGGCGTTGAG | CGAAAATCCA | TTAGATAGTC | CAGCCATCGG | TTCGGAAAAA | CAACCCTTGT | TTGAAACTAA |

FIG. 10A

| | | | | | | |
|---|---|---|---|---|---|---|
| 990 | 1000 | 1010 | 1020 | 1030 | 1040 | 1050 |
| TCGAAACCTA | TTTTACAAAT | CTATTGAGGA | TTTAATATTT | AAATTCAGAT | ATAAAGACGC | TGAAAATCAT |
| 1060 | 1070 | 1080 | 1090 | 1100 | 1110 | 1120 |
| TTGATTTTCG | CTCTAACATA | CCACCCTAAA | GATTATAAAT | TTAATGAATT | ATTAAAATAC | ATCAGCAACT |
| 1130 | 1140 | 1150 | 1160 | 1170 | 1180 | 1190 |
| ATATATTGAT | AGACATTTCC | AGTTTGTGAT | ATTAGTTTGT | GCGTCTCATT | ACAATGGCTG | TTATTTTTAA |
| 1200 | 1210 | 1220 | 1230 | 1240 | 1250 | 1260 |
| CAACAAACAA | CTGCTCGCAG | ACAATAGTAT | AGAAAAGGGA | GGTGAACTGT | TTTTGTTTAA | CGGTTCGTAC |
| 1270 | 1280 | 1290 | 1300 | 1310 | 1320 | 1330 |
| AACATTTTGG | AAAGTTATGT | TAATCCGGTG | CTGCTAAAAA | ATGGTGTAAT | TGAACTAGAA | GAAGCTGCGT |
| 1340 | 1350 | 1360 | 1370 | 1380 | 1390 | 1400 |
| ACTATGCCGG | CAACATATTG | TACAAAACCG | ACGATCCCAA | ATTCATTGAT | TATATAAATT | TAATAATTAA |
| 1410 | 1420 | 1430 | 1440 | 1450 | 1460 | 1470 |
| AGCAACACAC | TCCGAAGAAC | TACCAGAAAA | TAGCACTGTT | GTAAATTACA | GAAAAACTAT | GCGCAGCGGT |
| 1480 | 1490 | 1500 | 1510 | 1520 | 1530 | 1540 |
| ACTATACACC | CCATTAAAAA | AGACATATAT | ATTTATGACA | ACAAAAAATT | TACTCTATAC | GATAGATACA |
| 1550 | 1560 | 1570 | 1580 | 1590 | 1600 | 1610 |
| TATATGGATA | CGATAATAAC | TATGTTAATT | TTTATGAGGA | GAAAAATGAA | AAAGAGAAGG | AATACGAAGA |
| 1620 | 1630 | 1640 | 1650 | 1660 | 1670 | 1680 |
| AGAAGACGAC | AAGGCGTCTA | GTTTATGTGA | AAATAAAATT | ATATTGTCGC | AAATTAACTG | TGAATCATTT |
| 1690 | 1700 | 1710 | 1720 | 1730 | 1740 | 1750 |
| GAAAATGATT | TTAAATATTA | CCTCAGCGAT | TATAACTACG | CGTTTTCAAT | TATAGATAAT | ACTACAAATG |
| 1760 | 1770 | 1780 | 1790 | 1800 | 1810 | 1820 |
| TTCTTGTTGC | GTTTGGTTTG | TATCGTTAAT | AAAAAACAAA | TTTGACATTT | ATAATTGTTT | TATTATTCAA |
| 1830 | 1840 | 1850 | 1860 | 1870 | 1880 | 1890 |
| TAATTACAAA | TAGGATTGAG | ACCCTTGCAG | TTGCCAGCAA | ACGGACAGAG | CTTGTCGAGG | AGAGTTGTTG |
| 1900 | 1910 | 1920 | 1930 | 1940 | 1950 | 1960 |
| ATTCATTGTT | TGCCTCCCTG | CTGCGGTTTT | TCACCGAAGT | TCATGCCAGT | CCAGCGTTTT | TGCAGCAGAA |

FIG. 10B

| | | | | | | |
|---|---|---|---|---|---|---|
| 1970 | 1980 | 1990 | 2000 | 2010 | 2020 | 2030 |
| AAGCCGCCGA | CTTCGGTTTG | CGGTCGGCGAG | TGAAGATCCC | TTTCTTGTTA | CCGCCAACGC | GCAATATGCC |
| 2040 | 2050 | 2060 | 2070 | 2080 | 2090 | 2100 |
| TTGCGAGGTC | GCAAAATCGG | CGAAATTCCA | TACCTGTTCA | CCGACGACGG | CGCTGACGCG | ATCAAAGACG |
| 2110 | 2120 | 2130 | 2140 | 2150 | 2160 | 2170 |
| CGGTGATACA | TATCCAGCCA | TGCACACTGA | TACTCTTCAC | TCCACATGTC | GGTGTACATT | GAGTGCAGCC |
| 2180 | 2190 | 2200 | 2210 | 2220 | 2230 | 2240 |
| CGGCTAACGT | ATCCACGCCG | TATTCGGTGA | TGATAATCGG | CTGATGCAGT | TTCTCCTGCC | AGGCCAGAAG |
| 2250 | 2260 | 2270 | 2280 | 2290 | 2300 | 2310 |
| TTCTTTTTCC | AGTACCTTCT | CTGCCGTTTC | CAAATCGCCG | CTTTGGGACAT | ACCATCCGTA | ATAACGGTTC |
| 2320 | 2330 | 2340 | 2350 | 2360 | 2370 | 2380 |
| AGGCACAGCA | CATCAAAGAG | ATCGCTGATG | GTATCGGTGT | GAGCGTCGCA | GAACATTACA | TTGACGCAGG |
| 2390 | 2400 | 2410 | 2420 | 2430 | 2440 | 2450 |
| TGATCGGACG | CGTCGGGTCG | AGTTTACGCG | TTGCTTCCGC | CAGTGGCGCG | AAATATTCCC | GTGCACCTTG |
| 2460 | 2470 | 2480 | 2490 | 2500 | 2510 | 2520 |
| CGGACGGGTA | TCCGGTTCGT | TGGCAATACT | CCACATCACC | ACGCTTGGGT | GGTTTTTGTC | ACGCGCTATC |
| 2530 | 2540 | 2550 | 2560 | 2570 | 2580 | 2590 |
| AGCTCTTTAA | TCGCCTGTAA | GTGCGCTTGC | TGAGTTTCCC | CGTTGACTGC | CTCTTCGCTG | TACAGTTCTT |
| 2600 | 2610 | 2620 | 2630 | 2640 | 2650 | 2660 |
| TCGGCTTGTT | GCCCGCTTCG | AAACCAATGC | CTAAAGAGAG | GTTAAAGCCG | ACAGCAGCAG | TTTCATCAAT |
| 2670 | 2680 | 2690 | 2700 | 2710 | 2720 | 2730 |
| CACCACGATG | CCATGTTCAT | CTGCCCAGTC | GAGCATCTCT | TCAGCGTAAG | GGTAATGCGA | GGTACGGTAG |
| 2740 | 2750 | 2760 | 2770 | 2780 | 2790 | 2800 |
| GAGTTGGCCC | CAATCCAGTC | CATTAATGCG | TGGTCGTGCA | CCATCAGCAC | GTTATCGAAT | CCTTTGCCAC |
| 2810 | 2820 | 2830 | 2840 | 2850 | 2860 | 2870 |
| GCAAGTCCGC | ATCTTCATGA | CGACCAAAGC | CAGTAAAGTA | GAACGGTTTG | TGGTTAATCA | GGAACTGTTC |
| 2880 | 2890 | 2900 | 2910 | 2920 | 2930 | 2940 |
| GCCCTTCACT | GCCACTGACC | GGATGCCGAC | GCGAAGCGGG | TAGATATCAC | ACTCTGTCTG | GCTTTTGGCT |

FIG. 10C

| | | | | | | |
|---|---|---|---|---|---|---|
| 2950 | 2960 | 2970 | 2980 | 2990 | 3000 | 3010 |
| GTGACGCACA | GTTCATAGAG | ATAACCTTCA | CCCGGTTGCC | AGAGGTGCGG | ATTCACCACT | TGCAAAGTCC |
| 3020 | 3030 | 3040 | 3050 | 3060 | 3070 | 3080 |
| CGCTAGTGCC | TTGTCCAGTT | GCAACCACCT | GTTGATCCGC | ATCACGCAGT | TCAACGCTGA | CATCACCATT |
| 3090 | 3100 | 3110 | 3120 | 3130 | 3140 | 3150 |
| GGCCACCACC | TGCCAGTCAA | CAGACGCGTG | GTTACAGTCT | TGCGCGACAT | GCGTCACCAC | GGTGATATCG |
| 3160 | 3170 | 3180 | 3190 | 3200 | 3210 | 3220 |
| TCCACCCAGG | TGTTCGGCGT | GGTGTAGAGC | ATTACGCTGC | GATGGATTCC | GGCATAGTTA | AAGAAATCAT |
| 3230 | 3240 | 3250 | 3260 | 3270 | 3280 | 3290 |
| GGAAGTAAGA | CTGCTTTTTC | TTGCCGTTTT | CGTCGGTAAT | CACCATTCCC | GGCGGGATAG | TCTGCCAGTT |
| 3300 | 3310 | 3320 | 3330 | 3340 | 3350 | 3360 |
| CAGTTCGTTG | TTCACACAAA | CGGTGATACC | CCTCGACGGA | TTAAAGACTT | CAAGCGGTCA | ACTATGAAGA |
| 3370 | 3380 | 3390 | 3400 | 3410 | 3420 | 3430 |
| AGTGTTCGTC | TTCGTCCCAG | TAAGCTATGT | CTCCAGAATG | TAGCCATCCA | TCCTTGTCAA | TCAAGGCGTT |
| 3440 | 3450 | 3460 | 3470 | 3480 | 3490 | 3500 |
| GGTCGCTTCC | GGATTGTTTA | CATAACCGGA | CATAATCATA | GGTCCTCTGA | CACATAATTC | GCCTCTCTGA |
| 3510 | 3520 | 3530 | 3540 | 3550 | 3560 | 3570 |
| TTAACGCCCA | GCGTTTTCCC | GGTATCCAGA | TCCACAACCT | TCGCTTCAAA | AAATGGAACA | ACTTTACCGA |
| 3580 | 3590 | 3600 | 3610 | 3620 | 3630 | 3640 |
| CCGCGCCCGG | TTTATCATCC | CCCTCGGGTG | TAATCAGAAT | AGCTGATGTA | GTCTCAGTGA | GCCCATATCC |
| 3650 | 3660 | 3670 | 3680 | 3690 | 3700 | 3710 |
| TTGTCGTATC | CCTGGAAGAT | GGAAGCGTTT | TGCAACCGCT | TCCCCGACTT | CTTTCGAAAG | AGGTGCGCCC |
| 3720 | 3730 | 3740 | 3750 | 3760 | 3770 | 3780 |
| CCAGAAGCAA | TTTCGTGTAA | ATTAGATAAA | TCGTATTTGT | CAATCAGAGT | GCTTTTGGCG | AAGAATGAAA |
| 3790 | 3800 | 3810 | 3820 | 3830 | 3840 | 3850 |
| ATAGGGTTGG | TACTAGCAAC | GCACTTTGAA | TTTTGTAATC | CTGAAGGGAT | CGTAAAAACA | GCTCTTCTTC |
| 3860 | 3870 | 3880 | 3890 | 3900 | 3910 | 3920 |
| AAATCTATAC | ATTAAGACGA | CTCGAAATCC | ACATATCAAA | TATCCGAGTG | TAGTAAACAT | TCCAAAACCG |

FIG. 10D

| | | | | | | |
|---|---|---|---|---|---|---|
| 3930 | 3940 | 3950 | 3960 | 3970 | 3980 | 3990 |
| TGATGGAATG | GAACAACACT | TAAAATCGCA | GTATCCGGAA | TGATTTGATT | GCCAAAAATA | GGATCTCTGG |
| 4000 | 4010 | 4020 | 4030 | 4040 | 4050 | 4060 |
| CATGCGAGAA | TCTGACGCAG | GCAGTTCTAT | GCGGAAGGGC | CACACCCTTA | GGTAACCCAG | TAGATCCAGA |
| 4070 | 4080 | 4090 | 4100 | 4110 | 4120 | 4130 |
| GGAATTGTTT | TGTCACGATC | AAAGGACTCT | GGTACAAAAT | CGTATTCATT | AAAACCGGGA | GGTAGATGAG |
| 4140 | 4150 | 4160 | 4170 | 4180 | 4190 | 4200 |
| ATGTGACGAA | CGTGTACATC | GACTGAAATC | CCTGGTAATC | CGTTTTAGAA | TCCATGATAA | TAATTTTCTG |
| 4210 | 4220 | 4230 | 4240 | 4250 | 4260 | 4270 |
| GATTATTGGT | AATTTTTTTT | GCACGTTCAA | AATTTTTTGC | AACCCCTTTT | TGGAAACAAA | CACTACGGTA |
| 4280 | 4290 | 4300 | 4310 | 4320 | 4330 | 4340 |
| GGCTGCGAAA | TGTTCATACT | GTTGAGCAAT | TCACGTTCAT | TATAAATGTC | GTTCGCGGGC | GCAACTGCAA |
| 4350 | 4360 | 4370 | 4380 | 4390 | 4400 | 4410 |
| CTCCGATAAA | TAACGCGCCC | AACACCGGCA | TAAAGAATTG | AAGAGAGTTT | TCACTGCATA | CGACGATTCT |
| 4420 | 4430 | 4440 | 4450 | 4460 | 4470 | 4480 |
| GTGATTTGTA | TTCAGCCCAT | ATCGTTTCAT | AGCTTCTGCC | AACCGAACGG | ACATTTCGAA | GTATTCCGCG |
| 4490 | 4500 | 4510 | 4520 | 4530 | 4540 | 4550 |
| TACAGCCCGG | CCGTTTAAAC | GGCCGGGCTT | CAATACCCTG | ATTGACTGGA | ACAGCTGTAG | CCCTGAACAG |
| 4560 | 4570 | 4580 | 4590 | 4600 | 4610 | 4620 |
| CAGCGTGCGC | TGCTGACGCG | TCCGGCGATT | TCCGCCTCTG | ACAGTATTAC | CCGGACGGTC | AGCGATATTC |
| 4630 | 4640 | 4650 | 4660 | 4670 | 4680 | 4690 |
| TGGATAATGT | AAAAACGCGC | GGTGACGATG | CCCTGCGTGA | ATACAGCGCT | AAATTTGATA | AAACAGAAGT |
| 4700 | 4710 | 4720 | 4730 | 4740 | 4750 | 4760 |
| GACAGCGCTA | CGCGTCACCC | CTGAAGAGAT | CGCCGCCGCC | GGCGCGCGTC | TGAGCGACGA | ATTAAAACAG |
| 4770 | 4780 | 4790 | 4800 | 4810 | 4820 | 4830 |
| GCGATGACCG | CTGCCGTCAA | AAATATTGAA | ACGTTCCATT | CCGCGCAGAC | GCTACCGCCT | GTAGATGTGG |
| 4840 | 4850 | 4860 | 4870 | 4880 | 4890 | 4900 |
| AAACCCAGCC | AGGCGTGCGT | TGCCAGCAGG | TTACGCGTCC | CGTCTCGTCT | GTCGGTCTGT | ATATTCCCGG |

FIG. 10E

| | | | | | | |
|---|---|---|---|---|---|---|
| 4910 | 4920 | 4930 | 4940 | 4950 | 4960 | 4970 |
| CGGCTCGGCT | CCGCTCTTCT | CAACGGTGCT | GATGCTGGCG | ACGCCGGCGC | GCATTGCGGG | ATGCCAGAAG |
| 4980 | 4990 | 5000 | 5010 | 5020 | 5030 | 5040 |
| GTGGTTCTGT | GCTCGCCGCC | GCCCATCGCT | GATGAAATCC | TCTATGCGGC | GCAACTGTGT | GGCGTGCAGG |
| 5050 | 5060 | 5070 | 5080 | 5090 | 5100 | 5110 |
| AAATCTTTAA | CGTCGGCGGC | GCGCAGGCGA | TTTGCCGCTCT | GGCCTTCGGC | AGCGAGTCCG | TACCGAAAGT |
| 5120 | 5130 | 5140 | 5150 | 5160 | 5170 | 5180 |
| GGATAAAATT | TTTGGCCCCG | GCAACGCCTT | TGTAACCGAA | GCCAAACGTC | AGGTCAGCCA | GCGTCTCGAC |
| 5190 | 5200 | 5210 | 5220 | 5230 | 5240 | 5250 |
| GGCGCGGCTA | TCGATATGCC | AGCCGGGCGG | TCTGAAGTAC | TGGTGATCGC | AGACAGCGGC | GCAACACCGG |
| 5260 | 5270 | 5280 | 5290 | 5300 | 5310 | 5320 |
| ATTTCGTCGC | TTCTGACCTG | CTCTTCCCAGG | CTGAGCACGG | CCCGGATTCC | CAGGTGATCC | TGCTGACGCC |
| 5330 | 5340 | 5350 | 5360 | 5370 | 5380 | 5390 |
| TGATGCTGAC | ATTGCCCGCA | AGGTGGCGGA | GGCGGTAGAA | CGTCAACTGG | CGGAACTGCC | GCGCGCGGAC |
| 5400 | 5410 | 5420 | 5430 | 5440 | 5450 | 5460 |
| ACCGCCCGGC | AGGCCCTGAG | CGCCAGTCGT | CTGATTGTGA | CCAAAGATTT | AGCGCAGTGC | GTCGCCATCT |
| 5470 | 5480 | 5490 | 5500 | 5510 | 5520 | 5530 |
| CTAATCAGTA | TGGGCCGGAA | CACTTAATCA | TCCAGACGCG | CAATGCGCGC | GATTTGGTGG | ATGCGATTAC |
| 5540 | 5550 | 5560 | 5570 | 5580 | 5590 | 5600 |
| CAGCGCAGGC | TCGGTATTTC | TCGGCGACTG | GTCGCCGGAA | TCCGCCGGTG | ATTACGCTTC | CGGAACCAAC |
| 5610 | 5620 | 5630 | 5640 | 5650 | 5660 | 5670 |
| CATGTTTTAC | CGACCTATGG | CTATACTGCT | ACCTGTTCCA | GCCTTGGGTT | AGCGGATTTC | CAGAAACGGA |
| 5680 | 5690 | 5700 | 5710 | 5720 | 5730 | 5740 |
| TGACCGTTCA | GGAACTGTCG | AAAGCGGGCT | TTTCCGCTCT | GGCATCAACC | ATTGAAACAT | TGGCGGCGGC |
| 5750 | 5760 | 5770 | 5780 | 5790 | 5800 | 5810 |
| AGAACGTCTG | ACCGCCCATA | AAAATGCCGT | GACCCTGCGC | GTAAACGCCC | TCAAGGAGCA | AGCATGAGCA |
| 5820 | 5830 | 5840 | 5850 | 5860 | 5870 | 5880 |
| CTGAAAACAC | TCTCAGCGTC | GCTGACTTAG | CCCGTGAAAA | TGTCCGCAAC | CTGGAGATCC | AGACATGGAT |

FIG. 10F

| | | | | | | |
|---|---|---|---|---|---|---|
| 5890 | 5900 | 5910 | 5920 | 5930 | 5940 | 5950 |
| AAGATACATT | GATGAGTTTG | GACAAACCAC | AACTAGAATG | CAGTGAAAAA | AATGCTTTAT | TTGTGAAATT |
| 5960 | 5970 | 5980 | 5990 | 6000 | 6010 | 6020 |
| TGTGATGCTA | TTGCTTTATT | TGTAACCATT | ATAAGCTGCA | ATAAACAAGT | TAACAACAAC | AATTGCATTC |
| 6030 | 6040 | 6050 | 6060 | 6070 | 6080 | 6090 |
| ATTTTATGTT | TCAGGTTCAG | GGGGAGGTGT | GGGAGGTTTT | TTAAAGCAAG | TAAAACCTCT | ACAAATGTGG |
| 6100 | 6110 | 6120 | 6130 | 6140 | 6150 | 6160 |
| TATGGCTGAT | TATGATCTCT | AGGGCCGGCC | CTCGACGGCG | CGTCTAGAGC | AGTGTGGTTT | TCAAGAGGAA |
| 6170 | 6180 | 6190 | 6200 | 6210 | 6220 | 6230 |
| GCAAAAAGCC | TCTCCACCCA | GGCCTGGAAT | GTTTCCACCC | AATGTCGAGC | AGTGTGGTTT | TGCAAGAGGA |
| 6240 | 6250 | 6260 | 6270 | 6280 | 6290 | 6300 |
| AGCAAAAAGC | CTCTCCACCC | AGGCCTGGAA | TGTTTCCACC | CAATGTCGAG | CAAACCCCGC | CCAGCGTCTT |
| 6310 | 6320 | 6330 | 6340 | 6350 | 6360 | 6370 |
| GTCATTGGCG | AATTGGAACA | CGCATATGCA | GTCGGGGCGG | CGCGGTCCCA | GGTCCACTTC | GCATATTAAG |
| 6380 | 6390 | 6400 | 6410 | 6420 | 6430 | 6440 |
| GTGGCGCGTG | TGGCCTCGAA | CACCGAGCGA | CCCTGCAGCC | AATATGGGAT | CGGCCATTGA | ACAAGATGGA |
| 6450 | 6460 | 6470 | 6480 | 6490 | 6500 | 6510 |
| TTGCACGCAG | GTTCTCCGGC | CGCTTGGGTG | GAGAGGCTAT | TCGGCTATGA | CTGGGCACAA | CAGACAATCG |
| 6520 | 6530 | 6540 | 6550 | 6560 | 6570 | 6580 |
| GCTGCTCTGA | TGCCGCCGTG | TTCCGGCTGT | CAGCGCAGGG | GCGCCCGGTT | CTTTTTGTCA | AGACCGACCT |
| 6590 | 6600 | 6610 | 6620 | 6630 | 6640 | 6650 |
| GTCCGGTGCC | CTGAATGAAC | TGCAGGTAAG | TGCGGCCGTC | GATGGCCGAG | GCGGCCTCGG | CCTCTGCATA |
| 6660 | 6670 | 6680 | 6690 | 6700 | 6710 | 6720 |
| AATAAAAAAA | ATTAGTCAGC | CATGCATGGG | GCGGAGAATG | GGCGGAACTG | GGCGGAGTTA | GGGGCGGGAT |
| 6730 | 6740 | 6750 | 6760 | 6770 | 6780 | 6790 |
| GGGCGGAGTT | AGGGGCGGGA | CTATGGTTGC | TGACTAATTG | AGATGCATGC | TTTGCATACT | TCTGCCTGCT |
| 6800 | 6810 | 6820 | 6830 | 6840 | 6850 | 6860 |
| GGGGAGCCTG | GGGACTTTCC | ACACCTGGTT | GCTGACTAAT | TGAGATGCAT | GCTTTGCATA | CTTCTGCCTG |

FIG. 10G

| | | | | | | |
|---|---|---|---|---|---|---|
| 6870 | 6880 | 6890 | 6900 | 6910 | 6920 | 6930 |
| CTGGGGAGCC | TGGGGACTTT | CCACACCCTA | ACTGACACAC | ATTCCACAGA | ATTAATTCCC | CTAGTTATTA |
| 6940 | 6950 | 6960 | 6970 | 6980 | 6990 | 7000 |
| ATAGTAATCA | ATTACGGGGT | CATTAGTTCA | TAGCCCATAT | ATGGAGTTCC | GCGTTACATA | ACTTACGGTA |
| 7010 | 7020 | 7030 | 7040 | 7050 | 7060 | 7070 |
| AATGGCCCGC | CTGGCTGACC | GCCCAACGAC | CCCCGCCCAT | TGACGTCAAT | AATGACGTAT | GTTCCCATAG |
| 7080 | 7090 | 7100 | 7110 | 7120 | 7130 | 7140 |
| TAACGCCAAT | AGGGACTTTC | CATTGACGTC | AATGGGTGGA | GTATTTACGG | TAAACTGCCC | ACTTGGCAGT |
| 7150 | 7160 | 7170 | 7180 | 7190 | 7200 | 7210 |
| ACATCAAGTG | TATCATATGC | CAAGTACGCC | CCCTATTGAC | GTCAATGACG | GTAAATGGCC | CGCCTGGCAT |
| 7220 | 7230 | 7240 | 7250 | 7260 | 7270 | 7280 |
| TATGCCCAGT | ACATGACCTT | ATGGGACTTT | CCTACTTGCC | AGTACATCTA | CGTATTAGTC | ATCGCTATTA |
| 7290 | 7300 | 7310 | 7320 | 7330 | 7340 | 7350 |
| CCATGGTGAT | GCGGTTTTGG | CAGTACATCA | ATGGGCGTGG | ATAGCGGTTT | GACTCACGGG | GATTTCCAAG |
| 7360 | 7370 | 7380 | 7390 | 7400 | 7410 | 7420 |
| TCTCCACCCC | ATTGACGTCA | ATGGGAGTTT | GTTTTGGCAC | CAAAATCAAC | GGGACTTTCC | AAAATGTCGT |
| 7430 | 7440 | 7450 | 7460 | 7470 | 7480 | 7490 |
| AACAACTCCG | CCCCATTGAC | GCAAATGGGC | GGTAGGCGTG | TACGGTGGGA | GGTCTATATA | AGCAGAGCTG |
| 7500 | 7510 | 7520 | 7530 | 7540 | 7550 | 7560 |
| GGTACGTGAA | CCGTCAGATC | GCCTGGAGAC | GCCATCACAG | ATCTCTCACC | ATGGACATGA | GGGTCCCCGC |
| 7570 | 7580 | 7590 | 7600 | 7610 | 7620 | 7630 |
| TCAGCTCCTG | GGGCTCCTTC | TGCTCTGGCT | CCCAGGTGCC | AGATGTGACA | TCCAGATGAC | CCAGTCTCCA |
| 7640 | 7650 | 7660 | 7670 | 7680 | 7690 | 7700 |
| TCTTCCCTGT | CTGCATCTGT | AGGGGACAGA | GTCACCATCA | CTTGCAGGGC | AAGTCAGGAC | ATTAGGTATT |
| 7710 | 7720 | 7730 | 7740 | 7750 | 7760 | 7770 |
| ATTTAAATTG | GTATCAGCAG | AAACCAGGAA | AAGCTCCTAA | GCTCCTGATC | TATGTTGCAT | CCAGTTTGCA |
| 7780 | 7790 | 7800 | 7810 | 7820 | 7830 | 7840 |
| AAGTGGGGTC | CCATCAAGGT | TCAGCGGCAG | TGGATCTGGG | ACAGAGTTCA | CTCTCACCGT | CAGCAGCCTG |

FIG. 10H

| | | | | | | |
|---|---|---|---|---|---|---|
| 7850 | 7860 | 7870 | 7880 | 7890 | 7900 | 7910 |
| CAGCCTGAAG | ATTTTGCGAC | TTATTACTGT | CTACAGGTTT | ATAGTACCCC | TCGGACGTTC | GGCCAAGGGA |
| 7920 | 7930 | 7940 | 7950 | 7960 | 7970 | 7980 |
| CCAAGGTGGA | AATCAAACGT | ACGGTGGCTG | CACCATCTGT | CTTCATCTTC | CCGCCATCTG | ATGAGCAGTT |
| 7990 | 8000 | 8010 | 8020 | 8030 | 8040 | 8050 |
| GAAATCTGGA | ACTGCCTCTG | TTGTGTGCCT | GCTGAATAAC | TTCTATCCCA | GAGAGGCCAA | AGTACAGTGG |
| 8060 | 8070 | 8080 | 8090 | 8100 | 8110 | 8120 |
| AAGGTGGATA | ACGCCCTCCA | ATCGGGTAAC | TCCCAGGAGA | GTGTCACAGA | GCAGGACAGC | AAGGACAGCA |
| 8130 | 8140 | 8150 | 8160 | 8170 | 8180 | 8190 |
| CCTACAGCCT | CAGCAGCACC | CTGACGCTGA | GCAAAGCAGA | CTACGAGAAA | CACAAAGTCT | ACGCCTGCGA |
| 8200 | 8210 | 8220 | 8230 | 8240 | 8250 | 8260 |
| AGTCACCCAT | CAGGGCCTGA | GCTCGCCCGT | CACAAAGAGC | TTCAACAGGG | GAGAGTGTTG | AATTCAGATC |
| 8270 | 8280 | 8290 | 8300 | 8310 | 8320 | 8330 |
| CGTTAACGGT | TACCAACTAC | CTAGACTGGA | TTCGTGACAA | CATGCGGCCG | TGATATCTAC | GTATGATCAG |
| 8340 | 8350 | 8360 | 8370 | 8380 | 8390 | 8400 |
| CCTCGACTGT | GCCTTCTAGT | TGCCAGCCAT | CTGTTGTTTG | CCCCTCCCCC | GTGCCTTCCT | TGACCCTGGA |
| 8410 | 8420 | 8430 | 8440 | 8450 | 8460 | 8470 |
| AGGTGCCACT | CCCACTGTCC | TTTCCTAATA | AAATGAGGAA | ATTGCATCGC | ATTGTCTGAG | TAGGTGTCAT |
| 8480 | 8490 | 8500 | 8510 | 8520 | 8530 | 8540 |
| TCTATTCTGG | GGGGTGGGGT | GGGGCAGGAC | AGCAAGGGGG | AGGATTGGGA | AGACAATAGC | AGGCATGCTG |
| 8550 | 8560 | 8570 | 8580 | 8590 | 8600 | 8610 |
| GGGATGCGGT | GGGCTCTATG | GCTTCTGAGG | CGGAAAGAAC | CAGCTGGGAC | TAGTCGCAAT | TGGGCGGAGT |
| 8620 | 8630 | 8640 | 8650 | 8660 | 8670 | 8680 |
| TAGGGGCGGG | ATGGGCGGAG | TTAGGGGCGG | GGACTATGGT | GCTGACTAAT | TGAGATGCAT | GCTTTGCATA |
| 8690 | 8700 | 8710 | 8720 | 8730 | 8740 | 8750 |
| CTTCTGCCTG | CTGGGGAGCC | TGGGGACTTT | CCACACCTGG | TTGCTGACTA | ATTGAGATGC | ATGCTTTGCA |
| 8760 | 8770 | 8780 | 8790 | 8800 | 8810 | 8820 |
| TACTTCTGCC | TGCTGGGGAG | CCTGGGGACT | TTCCACACCC | TAACTGACAC | ACATTCCACA | GAATTAATTC |

FIG. 10I

| | | | | | | |
|---|---|---|---|---|---|---|
| 8830 | 8840 | 8850 | 8860 | 8870 | 8880 | 8890 |
| CCCTAGTTAT | TAATAGTAAT | CAATTACGGG | GTCATTAGTT | CATAGCCCAT | ATATGGAGTT | CCGCGTTACA |
| 8900 | 8910 | 8920 | 8930 | 8940 | 8950 | 8960 |
| TAACTTACGG | TAAATGGCCC | GCCTGGCTGA | CCGCCCAACG | ACCCCCGCCC | ATTGACGTCA | ATAATGACGT |
| 8970 | 8980 | 8990 | 9000 | 9010 | 9020 | 9030 |
| ATGTTCCCAT | AGTAACGCCA | ATAGGGACTT | TCCATTGACG | TCAATGGGTG | GAGTATTTAC | GGTAAACTGC |
| 9040 | 9050 | 9060 | 9070 | 9080 | 9090 | 9100 |
| CCACTTGGCA | GTACATCAAG | TGTATCATAT | GCCAAGTACG | CCCCCTATTG | ACGTCAATGA | CGGTAAATGG |
| 9110 | 9120 | 9130 | 9140 | 9150 | 9160 | 9170 |
| CCCGCCTGGC | ATTATGCCCA | GTACATGACC | TTATGGGACT | TTCCTACTTG | GCAGTACATC | TACGTATTAG |
| 9180 | 9190 | 9200 | 9210 | 9220 | 9230 | 9240 |
| TCATCGCTGT | TACCATGGTG | ATGCGGTTTT | GGCAGTACAT | CAATGGGCGT | GGATAGCGGT | TTGACTCACG |
| 9250 | 9260 | 9270 | 9280 | 9290 | 9300 | 9310 |
| GGGATTTCCA | AGTCTCCACC | CCATTGACGT | CAATGGGAGT | TTGTTTTGGC | ACCAAAATCA | ACGGGACTTT |
| 9320 | 9330 | 9340 | 9350 | 9360 | 9370 | 9380 |
| CCAAAATGTC | GTAACAACTC | CGCCCCATTG | ACGCAAATGG | GCGGTAGGCG | TGTACGGTGG | GAGGTCTATA |
| 9390 | 9400 | 9410 | 9420 | 9430 | 9440 | 9450 |
| TAAGCAGAGC | TGGGTACGTG | AACCGTCAGA | TCGCCTGGAG | ACGCCGTCGA | CATGGGTTGG | AGCCTCATCT |
| 9460 | 9470 | 9480 | 9490 | 9500 | 9510 | 9520 |
| TGCTCTTCCT | TGTCGCTGTT | GCTACGCGTG | TCCTGTCCGA | GGTGCAGCTG | GTGGAGTCTG | GGGGCGGCTT |
| 9530 | 9540 | 9550 | 9560 | 9570 | 9580 | 9590 |
| GGCAAAGCCT | GGGGGGTCCC | TGAGACTCTC | CTGCGCAGCC | TCCGGGTTCA | GGTTCACCTT | CAATAACTAC |
| 9600 | 9610 | 9620 | 9630 | 9640 | 9650 | 9660 |
| TACATGGACT | GGGTCCGCCA | GGCTCCAGGG | CAGGGGCTGG | AGTGGGTCTC | ACGTATTAGT | AGTAGTGGTG |
| 9670 | 9680 | 9690 | 9700 | 9710 | 9720 | 9730 |
| ATCCCACATG | GTACGCAGAC | TCCGTGAAGG | GCAGATTCAC | CATCTCCAGA | GAGAACGCCA | AGAACACACT |
| 9740 | 9750 | 9760 | 9770 | 9780 | 9790 | 9800 |
| GTTTCTTCAA | ATGAACAGCC | TGAGAGCTGA | GGACACGGCT | GTCTATTACT | GTGCGAGCTT | GACTACAGGG |

FIG. 10J

| | | | | | | |
|---|---|---|---|---|---|---|
| 9810 | 9820 | 9830 | 9840 | 9850 | 9860 | 9870 |
| TCTGACTCCCT | GGGGCCAGGG | AGTCCTGGTC | ACCGTCTCCT | CAGCTAGCAC | CAAGGGCCCA | TCGGTCTTCC |
| 9880 | 9890 | 9900 | 9910 | 9920 | 9930 | 9940 |
| CCCTGGCACC | CTCCTCCAAG | AGCACCTCTG | GGGGCACAGC | GGCCCTGGGC | TGCCTGGTCA | AGGACTACTT |
| 9950 | 9960 | 9970 | 9980 | 9990 | 10000 | 10010 |
| CCCCGAACCG | GTGACGGTGT | CGTGGAACTC | AGGCGCCCTG | ACCAGCGGCG | TGCACACCTT | CCCGGCTGTC |
| 10020 | 10030 | 10040 | 10050 | 10060 | 10070 | 10080 |
| CTACAGTCCT | CAGGACTCTA | CTCCCTCAGC | AGCGTGGTGA | CCGTGCCCTC | CAGCAGCTTG | GGCACCCAGA |
| 10090 | 10100 | 10110 | 10120 | 10130 | 10140 | 10150 |
| CCTACATCTG | CAACGTGAAT | CACAAGCCCA | GCAACACCAA | GGTGGACAAG | AAAGTTGAGC | CCAAATCTTG |
| 10160 | 10170 | 10180 | 10190 | 10200 | 10210 | 10220 |
| TGACAAAACT | CACACATGCC | CACCGTGCCC | AGCACCTGAA | CTCCTGGGGG | GACCGTCAGT | CTTCCTCTTC |
| 10230 | 10240 | 10250 | 10260 | 10270 | 10280 | 10290 |
| CCCCCAAAAC | CCAAGGACAC | CCTCATGATC | TCCCGGACCC | CTGAGGTCAC | ATGCGTGGTG | GTGGACGTGA |
| 10300 | 10310 | 10320 | 10330 | 10340 | 10350 | 10360 |
| GCCACGAAGA | CCCTGAGGTC | AAGTTCAACT | GGTACGTGGA | CGGCGTGGAG | GTGCATAATG | CCAAGACAAA |
| 10370 | 10380 | 10390 | 10400 | 10410 | 10420 | 10430 |
| GCCGCGGGAG | GAGCAGTACA | ACAGCACGTA | CCGTGTGGTC | AGCGTCCTCA | CCGTCCTGCA | CCAGGACTGG |
| 10440 | 10450 | 10460 | 10470 | 10480 | 10490 | 10500 |
| CTGAATGGCA | AGGAGTACAA | GTGCAAGGTC | TCCAACAAAG | CCCTCCCAGC | CCCCATCGAG | AAAACCATCT |
| 10510 | 10520 | 10530 | 10540 | 10550 | 10560 | 10570 |
| CCAAAGCCAA | AGGGCAGCCC | CGAGAACCAC | AGGTGTACAC | CCTGCCCCCA | TCCCGGGATG | AGCTGACCAA |
| 10580 | 10590 | 10600 | 10610 | 10620 | 10630 | 10640 |
| GAACCAGGTC | AGCCTGACCT | GCCTGGTCAA | AGGCTTCTAT | CCCAGCGACA | TCGCCGTGGA | GTGGGAGAGC |
| 10650 | 10660 | 10670 | 10680 | 10690 | 10700 | 10710 |
| AATGGGCAGC | CGGAGAACAA | CTACAAGACC | ACGCCTCCCG | TGCTGGACTC | CGACGGCTCC | TTCTTCCTCT |
| 10720 | 10730 | 10740 | 10750 | 10760 | 10770 | 10780 |
| ACAGCAAGCT | CACCGTGGAC | AAGAGCAGGT | GGCAGCAGGG | GAACGTCTTC | TCATGCTCCG | TGATGCATGA |

FIG. 10K

| | | | | | | |
|---|---|---|---|---|---|---|
| 10790 | 10800 | 10810 | 10820 | 10830 | 10840 | 10850 |
| GGCTCTGCAC | AACCACTACA | CGCAGAAGAG | CCTCTCCCTG | TCTCCGGGTA | AATGAGGATC | CGTTAACGGT |
| 10860 | 10870 | 10880 | 10890 | 10900 | 10910 | 10920 |
| TACCAACTAC | CTAGACTGGA | TTCGTGACAA | CATGCGGCCG | TGATATCTAC | GTATGATCAG | CCTCGACTGT |
| 10930 | 10940 | 10950 | 10960 | 10970 | 10980 | 10990 |
| GCCTTCTAGT | TGCCAGCCAT | CTGTTGTTTGC | CCCCTCCCCC | GTGCCTTCCT | TGACCCTGGA | AGGTGCCACT |
| 11000 | 11010 | 11020 | 11030 | 11040 | 11050 | 11060 |
| CCCACTGTCC | TTTCCTAATA | AAATGAGGAA | ATTGCATCGC | ATTGTCTGAG | TAGGTGTCAT | TCTATTCTGG |
| 11070 | 11080 | 11090 | 11100 | 11110 | 11120 | 11130 |
| GGGGTGGGGT | GGGGCAGGAC | AGCAAGGGGG | AGGATTGGGA | AGACAATAGC | AGGCATGCTG | GGGATGCGGT |
| 11140 | 11150 | 11160 | 11170 | 11180 | 11190 | 11200 |
| GGGCTCTATG | GCTTCTGAGG | CGGAAAGAAC | CAGCTGGGGC | TCGACAGCAA | CGCTAGGTCG | AGGCCGCTAC |
| 11210 | 11220 | 11230 | 11240 | 11250 | 11260 | 11270 |
| TAACTCTCTC | CTCCCTCCTT | TTTCCTGCAG | GACGAGGCAG | CGCGGCTATC | GTGGCTGGCC | ACGACGGGCG |
| 11280 | 11290 | 11300 | 11310 | 11320 | 11330 | 11340 |
| TTCCTTGCGC | AGCTGTGCTC | GACGTTGTCA | CTGAAGCGGG | AAGGGACTGG | CTGCTATTGG | GCGAAGTGCC |
| 11350 | 11360 | 11370 | 11380 | 11390 | 11400 | 11410 |
| GGGGCAGGAT | CTCCTGTCAT | CTCACCTTGC | TCCTGCCGAG | AAAGTATCCA | TCATGGCTGA | TGCAATGCGG |
| 11420 | 11430 | 11440 | 11450 | 11460 | 11470 | 11480 |
| CGGCTGCATA | CGCTTGATCC | GGCTACCTGC | CCATTCGACC | ACCAAGCGAA | ACATCGCATC | GAGCGAGCAC |
| 11490 | 11500 | 11510 | 11520 | 11530 | 11540 | 11550 |
| GTACTCGGAT | GGAAGCCGGT | CTTGTCGATC | AGGATGATCT | GGACGAAGAG | CATCAGGGGC | TCGCGCCAGC |
| 11560 | 11570 | 11580 | 11590 | 11600 | 11610 | 11620 |
| CGAACTGTTC | GCCAGGTAAG | TGAGCTCCAA | TTCAAGCTCT | CGAGCTAGGG | CGGCCAGCTA | GTAGCTTTGC |
| 11630 | 11640 | 11650 | 11660 | 11670 | 11680 | 11690 |
| TTCTCAATTT | CTTATTTGCA | TAATGAGAAA | AAAAGGAAAA | TTAATTTTAA | CACCAATTCA | GTAGTTGATT |
| 11700 | 11710 | 11720 | 11730 | 11740 | 11750 | 11760 |
| GAGCAAATGC | GTTGCCAAAA | AGGATGCTTT | AGAGACAGTG | TTCTCTGCAC | AGATAAGGAC | AAACATTATT |

FIG. 10L

| | | | | | | |
|---|---|---|---|---|---|---|
| 11770 | 11780 | 11790 | 11800 | 11810 | 11820 | 11830 |
| CAGAGGGAGT | ACCCAGAGCT | GAGACTCCTA | AGCCAGTGAG | TGGCACAGCA | TCCAGGGAGA | AATATGCTTG |
| 11840 | 11850 | 11860 | 11870 | 11880 | 11890 | 11900 |
| TCATCACCGA | AGCCTGATTC | CGTAGAGCCA | CACCCTGGTA | AGGGCCAATC | TGCTCACACA | GGATAGAGAG |
| 11910 | 11920 | 11930 | 11940 | 11950 | 11960 | 11970 |
| GGCAGGAGCC | AGGCAGAGC | ATATAAGGTG | AGGTAGGATC | AGTTGCTCCT | CACATTTGCT | TCTGACATAG |
| 11980 | 11990 | 12000 | 12010 | 12020 | 12030 | 12040 |
| TTGTGTTGGG | AGCTTGGATA | GCTTGGGGGG | GGGACAGCTC | AGGGCTGCGA | TTTCGCGCCA | AACTTGACGG |
| 12050 | 12060 | 12070 | 12080 | 12090 | 12100 | 12110 |
| CAATCCTAGC | GTGAAGGCTG | GTAGGATTTT | ATCCCCGCTG | CCATCATGGT | TCGACCATTG | AACTGCATCG |
| 12120 | 12130 | 12140 | 12150 | 12160 | 12170 | 12180 |
| TCGCCGTGTC | CCAAAATATG | GGGATTGGCA | AGAACGGAGA | CCTACCCTGG | CCTCCGCTCA | GGAACGAGTT |
| 12190 | 12200 | 12210 | 12220 | 12230 | 12240 | 12250 |
| CAAGTACTTC | CAAAGAATGA | CCACAACCTC | TTCAGTGGAA | GGTAAACAGA | ATCTGGTGAT | TATGGGTAGG |
| 12260 | 12270 | 12280 | 12290 | 12300 | 12310 | 12320 |
| AAAACCTGGT | TCTCCATTCC | TGAGAAGAAT | CGACCTTTAA | AGGACAGAAT | TAATATAGTT | CTCAGTAGAG |
| 12330 | 12340 | 12350 | 12360 | 12370 | 12380 | 12390 |
| AACTCAAAGA | ACCACCACGA | GGAGCTCATT | TTCTTGCCAA | AAGTTTGGAT | GATGCCTTAA | CGTAGGCGCG |
| 12400 | 12410 | 12420 | 12430 | 12440 | 12450 | 12460 |
| CCATTAAGAC | TTATTGAACA | ACCGGAATTG | GCAAGTAAAG | TAGACATGGT | TTGGATAGTC | GGAGGCAGTT |
| 12470 | 12480 | 12490 | 12500 | 12510 | 12520 | 12530 |
| CTGTTTACCA | GGAAGCCATG | AATCAACCAG | GCAACCTCAG | ACTCTTTGTG | ACAAGGATCA | TGCAGGAATT |
| 12540 | 12550 | 12560 | 12570 | 12580 | 12590 | 12600 |
| TGAAAGTGAC | ACGTTTTTCC | CAGAAATTGA | TTTGGGGAAA | TATAAACTTC | TCCCAGAATA | CCCAGGCGTC |
| 12610 | 12620 | 12630 | 12640 | 12650 | 12660 | 12670 |
| CTCTCTGAGG | TCAAGGAGGA | AAAAGGCATC | AAGTATAAGT | TTGAAGTCTA | CGAGAAGAAA | GACTAACAGG |
| 12680 | 12690 | 12700 | 12710 | 12720 | 12730 | 12740 |
| AAGATGCTTT | CAAGTTCTCT | GCTCCCCTCC | TAAAGCTATG | CATTTTTATA | AGACCATGGG | ACTTTTGCTG |

FIG. 10M

| | | | | | | |
|---|---|---|---|---|---|---|
| 12750 | 12760 | 12770 | 12780 | 12790 | 12800 | 12810 |
| GCTTTAGATC | AGCCTCGACT | GTGCCTTCTA | GTTGCCAGCC | ATCTGTTGTT | TGCCCCTCCC | CCGTGCCTTC |
| 12820 | 12830 | 12840 | 12850 | 12860 | 12870 | 12880 |
| CTTGACCCTG | GAAGGTGCCA | CTCCCACTGT | CCTTTCCTAA | TAAAATGAGG | AAATTGCATC | GCATTGTCTG |
| 12890 | 12900 | 12910 | 12920 | 12930 | 12940 | 12950 |
| AGTAGGTGTC | ATTCTATTCT | GGGGGGTGGG | GTGGGGCAGG | ACAGCAAGGG | GGAGGATTGG | GAAGACAATA |
| 12960 | 12970 | 12980 | 12990 | 13000 | 13010 | 13020 |
| GCAGGCATGC | TGGGGATGCG | GTGGGCTCTA | TGGCTTCTGA | GGCGGAAAGA | ACCAGCTGGG | GCTCGAAGCG |
| 13030 | 13040 | 13050 | 13060 | 13070 | 13080 | 13090 |
| GCCGCCCATT | TCGCTGGTGG | TCAGATGCGG | GATGGCGTGG | GACGCGGCGG | GGAGCGTCAC | ACTGAGGTTT |
| 13100 | 13110 | 13120 | 13130 | 13140 | 13150 | 13160 |
| TCCGCCAGAC | GCCACTGCTG | CCAGGCGCTG | ATGTGCCCGG | CTTCTGACCA | TGCGGTCGCG | TTCGGTTGCA |
| 13170 | 13180 | 13190 | 13200 | 13210 | 13220 | 13230 |
| CTACGCGTAC | TGTGAGCCAG | AGTTGCCCGG | CGCTCTCCGG | CTGCGGTAGT | TCAGGCAGTT | CAATCAACTG |
| 13240 | 13250 | 13260 | 13270 | 13280 | 13290 | 13300 |
| TTTACCTTGT | GGAGCGACAT | CCAGAGGCAC | TTCACCGCTT | GCCAGCGGCT | TACCATCCAG | CGCCACCATC |
| 13310 | 13320 | 13330 | 13340 | 13350 | 13360 | 13370 |
| CAGTGCAGGA | GCTCGTTATC | GCTATGACGG | AACAGGTATT | CGCTGGTCAC | TTCGATGGTT | TGCCCGGATA |
| 13380 | 13390 | 13400 | 13410 | 13420 | 13430 | 13440 |
| AACGGAACTG | GAAAAACTGC | TGCTGGTGTT | TTGCTTCCGT | CAGCGCTGGA | TGCGGCGTGC | GGTCGGCAAA |
| 13450 | 13460 | 13470 | 13480 | 13490 | 13500 | 13510 |
| GACCAGACCG | TTCATACAGA | ACTGGCGATC | CGTTCGGCTA | TCGCCAAAAT | CACCGCCGTA | AGCCGACCAC |
| 13520 | 13530 | 13540 | 13550 | 13560 | 13570 | 13580 |
| GGGTTGCCGT | TTTCATCATA | TTTAATCAGC | GACTGATCCA | CCCAGTCCCA | GACGAAGCCG | CCCTGTAAAC |
| 13590 | 13600 | 13610 | 13620 | 13630 | 13640 | 13650 |
| GGGGATACTG | ACGAAACGCC | TGCCAGTATT | TAGCGAAACC | GCCAAGACTG | TTACCCATCG | CGTGGGCGTA |
| 13660 | 13670 | 13680 | 13690 | 13700 | 13710 | 13720 |
| TTCGCAAAGG | ATCAGCGGGC | GCGTCTCTCC | AGGTAGCGAA | AGCCATTTTT | TGATGGACCA | TTTCGGCACA |

FIG. 10N

| | | | | | | |
|---|---|---|---|---|---|---|
| 13730 | 13740 | 13750 | 13760 | 13770 | 13780 | 13790 |
| GCCGGGAAGG | GCTGGTCTTC | ATCCACGCGC | GCGTACATCG | GGCAAATAAT | ATCGGTGGCC | GTGGTGTCGG |
| 13800 | 13810 | 13820 | 13830 | 13840 | 13850 | 13860 |
| CTCCGCCGCC | TTCATACTGC | ACCGGGCGGG | AAGGATCGAC | AGATTTGATC | CAGCGATACA | GCGCGTCGTG |
| 13870 | 13880 | 13890 | 13900 | 13910 | 13920 | 13930 |
| ATTAGCGCCG | TGGCCTGATT | CATTCCCCAG | CGACCAGATG | ATCACACTCG | GGTGATTACG | ATCGCGCTGC |
| 13940 | 13950 | 13960 | 13970 | 13980 | 13990 | 14000 |
| ACCATTCGCG | TTACGCGTTC | GCTCATCGCC | GGTAGCCAGC | GCGGATCATC | GGTCAGACGA | TTCATTGGCA |
| 14010 | 14020 | 14030 | 14040 | 14050 | 14060 | 14070 |
| CCATGCCGTG | GGTTTCAATA | TTGGCTTCAT | CCACCACATA | CAGGCCGTAG | CGGTCGCACA | GCGTGTACCA |
| 14080 | 14090 | 14100 | 14110 | 14120 | 14130 | 14140 |
| CAGCGGATGG | TTCGGATAAT | GCGAACAGCG | CACGGCGTTA | AAGTTGTTCT | GCTTCATCAG | CAGGATATCC |
| 14150 | 14160 | 14170 | 14180 | 14190 | 14200 | 14210 |
| TGCACCATCG | TCTGCTCATC | CATGACCTGA | CCATGCAGAG | GATGATGCTC | GTGACGGTTA | ACGCCTCGAA |
| 14220 | 14230 | 14240 | 14250 | 14260 | 14270 | 14280 |
| TCAGCAACGG | CTTGCCGTTC | AGCAGCAGCA | GACCATTTTC | AATCCGCACC | TCGCGGAAAC | CGACATCGCA |
| 14290 | 14300 | 14310 | 14320 | 14330 | 14340 | 14350 |
| GGCTTCTGCT | TCAATCAGCG | TGCCGTCGGC | GGTGTGCAGT | TCAACCACCG | CACGATAGAG | ATTCGGGATT |
| 14360 | 14370 | 14380 | 14390 | 14400 | 14410 | 14420 |
| TCGGCGCTCC | ACAGTTTCGG | GTTTTCGACG | TTCAGACGTA | GTGTGACGCG | ATCGGCATAA | CCACCACGCT |
| 14430 | 14440 | 14450 | 14460 | 14470 | 14480 | 14490 |
| CATCGATAAT | TTCACCGCCG | AAAGGCGCGG | TGCCGCTGGC | GACCTGCGTT | TCACCCTGCC | ATAAAGAAAC |
| 14500 | 14510 | 14520 | 14530 | 14540 | 14550 | 14560 |
| TGTTACCCGT | AGGTAGTCAC | GCAACTCGCC | GCACATCTGA | ACTTCAGCCT | CCAGTACAGC | GCGGCTGAAA |
| 14570 | 14580 | 14590 | 14600 | 14610 | 14620 | 14630 |
| TCATCATTAA | AGCGAGTGGC | AACATGGAAA | TCGCTGATTT | GTGTAGTCGG | TTTATGCAGC | AACGAGACGT |
| 14640 | 14650 | 14660 | 14670 | 14680 | 14690 | 14700 |
| CACGGAAAAT | GCCGCTCATC | CGCCACATAT | CCTGATCTTC | CAGATAACTG | CCGTCACTCC | AGCGCAGCAC |

FIG. 10P

| | | | | | | |
|---|---|---|---|---|---|---|
| 14710 | 14720 | 14730 | 14740 | 14750 | 14760 | 14770 |
| CATCACCGCG | AGGCGGTTTT | CTCCGGCGCG | TAAAAATGCG | CTCAGGTCAA | ATTCAGACGG | CAAACGACTG |
| 14780 | 14790 | 14800 | 14810 | 14820 | 14830 | 14840 |
| TCCTGGCCGT | AACCGACCCA | GCGCCCGTTG | CACCACAGAT | GAAACGCCGA | GTTAACGCCA | TCAAAAATAA |
| 14850 | 14860 | 14870 | 14880 | 14890 | 14900 | 14910 |
| TTCGCGTCTG | GCCTTCCTGT | AGCCAGCTTT | CATCAACATT | AAATGTGAGC | GAGTAACAAC | CCGTCGGATT |
| 14920 | 14930 | 14940 | 14950 | 14960 | 14970 | 14980 |
| CTCCGTGGGA | ACAAACGGCG | GATTGACCGT | AATGGGATAG | GTCACGTTGG | TGTAGATGGG | CGCATCGTAA |
| 14990 | 15000 | 15010 | 15020 | 15030 | 15040 | 15050 |
| CCGTGCATCT | GCCAGTTTGA | GGGGACGACG | ACAGTATCGG | CCTCAGGAAG | ATCGCACTCC | AGCCAGCTTT |
| 15060 | 15070 | 15080 | 15090 | 15100 | 15110 | 15120 |
| CCGGCACCGC | TTCTGGTGCC | GGAAACCAGG | GCAAGCGCCA | TTCGCCATTC | AGGCTGCGCA | ACTGTTGGGA |
| 15130 | 15140 | 15150 | 15160 | 15170 | 15180 | 15190 |
| AGGGCGATCG | GTGCGGGCCT | CTTCGCTATT | ACGCCAGCTG | GCGAAAGGGG | GATGTGCTGC | AAGGCGATTA |
| 15200 | 15210 | 15220 | 15230 | 15240 | 15250 | 15260 |
| AGTTGGGTAA | CGCCAGGGTT | TTCCCAGTCA | CGACGTTGTA | AAACGACTTA | ATCCGTCGAG | GGGCTGCCTC |
| 15270 | 15280 | 15290 | 15300 | 15310 | 15320 | 15330 |
| GAAGCAGACG | ACCTTCCGTT | GTGCAGCCAG | CGGCGCCTGC | GCCGGTGCCC | ACAATCGTGC | GCGAACAAAC |
| 15340 | 15350 | 15360 | 15370 | 15380 | 15390 | 15400 |
| TAAACCAGAA | CAAATTATAC | CGGCGGCACC | GCCGCCACCA | CCTTCTCCCG | TGCCTAACAT | TCCAGCGCCT |
| 15410 | 15420 | 15430 | 15440 | 15450 | 15460 | 15470 |
| CCACCACCAC | CACCACCATC | GATGTCTGAA | TTGCCGCCCG | CTCCACCAAT | GCCGACGGAA | CCTCAACCCG |
| 15480 | 15490 | 15500 | 15510 | 15520 | 15530 | 15540 |
| CTGCACCTTT | AGACGACAGA | CAACAATTGT | TGGAAGCTAT | TAGAAACGAA | AAAAATCGCA | CTCGTCTCAG |
| 15550 | 15560 | 15570 | 15580 | 15590 | 15600 | 15610 |
| ACCGGTCAAA | CCAAAAACGG | CGCCCGAAAC | CAGTACAATA | GTTGAGGTGC | CGACTGTGTT | GCCTAAAGAG |
| 15620 | 15630 | 15640 | 15650 | 15660 | 15670 | 15680 |
| ACATTTGAGC | CTAAACCGCC | GTCTGCATCA | CCGCCACCAC | CTCCGCCTCC | GCCTCCGCCG | CCAGCCCCGC |

FIG. 10Q

| | | | | | | |
|---|---|---|---|---|---|---|
| 15690 | 15700 | 15710 | 15720 | 15730 | 15740 | 15750 |
| CTGCGCCTCC | ACCGATGGTA | GATTTATCAT | CAGCTCCACC | ACCGCCGCCA | TTAGTAGATT | TGCCGTCTGA |
| 15760 | 15770 | 15780 | 15790 | 15800 | 15810 | 15820 |
| AATGTTACCA | CCGCCTGCAC | CATCGCTTTC | TAACGTGTTG | TCTGAATTAA | AATCGGGCAC | AGTTAGATTG |
| 15830 | 15840 | 15850 | 15860 | 15870 | 15880 | 15890 |
| AAACCCGCCC | AAAAACGCCC | GCAATCAGAA | ATAATTCCAA | AAAGCTCAAC | TACAAATTTG | ATCGCGGACG |
| 15900 | 15910 | 15920 | 15930 | 15940 | 15950 | 15960 |
| TGTTAGCCGA | CACAATTAAT | AGGCGTCGTG | TGGCTATGGC | AAAATCGTCT | TCGGAAGCAA | CTTCTAACGA |
| 15970 | 15980 | 15990 | 16000 | 16010 | 16020 | 16030 |
| CGAGGGTTGG | GACGACGACG | ATAATCGGCC | TAATAAAGCT | AACACGCCCG | ATGTTAAATA | TGTCCAAGCT |
| 16040 | 16050 | 16060 | 16070 | 16080 | 16090 | 16100 |
| ACTAGTGGTA | CCGCTTGGCA | GAACATATCC | ATCGCGTCCG | CCATCTCCAG | CAGCCGCACG | CGGCGCATCT |
| 16110 | 16120 | 16130 | 16140 | 16150 | 16160 | 16170 |
| CGGGCAGCGT | TGGGTCCTGG | CCACGGGTGC | GCATGATCGT | GCTCCTGTCG | TTGAGGACCC | GGCTAGGCTG |
| 16180 | 16190 | 16200 | 16210 | 16220 | 16230 | 16240 |
| GCGGGGTTGC | CTTACTGGTT | AGCAGAATGA | ATCACCGATA | CGCGAGCGAA | CGTGAAGCGA | CTGCTGCTGC |
| 16250 | 16260 | 16270 | 16280 | 16290 | 16300 | 16310 |
| AAAACGTCTG | CGACCTGAGC | AACAACATGA | ATGGTCTTCG | GTTTCCGTGT | TTCGTAAAGT | CTGGAAACGC |
| 16320 | 16330 | 16340 | 16350 | 16360 | 16370 | 16380 |
| GGAAGTCAGC | GCCCTGCACC | ATTATGTTCC | GGATCTGCAT | CGCAGGATGC | TGCTGGCTAC | CCTGTGGAAC |
| 16390 | 16400 | 16410 | 16420 | 16430 | 16440 | 16450 |
| ACCTACATCT | GTATTAACGA | AGCGCTGGCA | TTGACCCTGA | GTGATTTTTC | TCTGGTCCCG | CCGCATCCAT |
| 16460 | 16470 | 16480 | 16490 | 16500 | 16510 | 16520 |
| ACCGCCAGTT | GTTTACCCTC | ACAACGTTCC | AGTAACCGGG | CATGTTCATC | ATCAGTAACC | CGTATCGTGA |
| 16530 | 16540 | 16550 | 16560 | 16570 | 16580 | 16590 |
| GCATCCTCTC | TCGTTTCATC | GGTATCATTA | CCCCCATGAA | CAGAAATCCC | CCTTACACGG | AGGCATCAGT |
| 16600 | 16610 | 16620 | 16630 | 16640 | 16650 | 16660 |
| GACCAAACAG | GAAAAAACCG | CCCTTAACAT | GGCCCGCTTT | ATCAGAAGCC | AGACATTAAC | GCTTCTGGAG |

FIG. 10R

| | | | | | | |
|---|---|---|---|---|---|---|
| 16670 | 16680 | 16690 | 16700 | 16710 | 16720 | 16730 |
| AAACTCAACG | AGCTGGACGC | GGATGAACAG | GCAGACATCT | GTGAATCGCT | TCACGACCAC | GCTGATGAGC |
| 16740 | 16750 | 16760 | 16770 | 16780 | 16790 | 16800 |
| TTTACCGCAG | CTGCCTCGCG | CGTTTCGGTG | ATGACGGTGA | AAACCTCTGA | CACATGCAGC | TCCCGGAGAC |
| 16810 | 16820 | 16830 | 16840 | 16850 | 16860 | 16870 |
| GGTCACAGCT | TGTCTGTAAG | CGGATGCCGG | GAGCAGACAA | GCCCGTCAGG | GCGCGTCAGC | GGGTGTTGGC |
| 16880 | 16890 | 16900 | 16910 | 16920 | 16930 | 16940 |
| GGGTGTCGGG | GCGCAGCCAT | GACCCAGTCA | CGTAGCGATA | GCGGAGTGTA | TACTGGCTTA | ACTATGCGGC |
| 16950 | 16960 | 16970 | 16980 | 16990 | 17000 | 17010 |
| ATCAGAGCAG | ATTGTACTGA | GAGTGCACCA | TATGCGGTGT | GAAATACCGC | ACAGATGCGT | AAGGAGAAAA |
| 17020 | 17030 | 17040 | 17050 | 17060 | 17070 | 17080 |
| TACCGCATCA | GGCGCTCTTC | CGCTTCCTCG | CTCACTGACT | CGCTGCGCTC | GGTCGTTCGG | CTGCGGCGAG |
| 17090 | 17100 | 17110 | 17120 | 17130 | 17140 | 17150 |
| CGGTATCAGC | TCACTCAAAG | GCGGTAATAC | GGTTATCCAC | AGAATCAGGG | GATAACGCAG | GAAAGAACAT |
| 17160 | 17170 | 17180 | 17190 | 17200 | 17210 | 17220 |
| GTGAGCAAAA | GGCCAGCAAA | AGGCCAGGAA | CCGTAAAAAG | GCCGCGTTGC | TGGCGTTTTT | CCATAGGCTC |
| 17230 | 17240 | 17250 | 17260 | 17270 | 17280 | 17290 |
| CGCCCCCCTG | ACGAGCATCA | CAAAAATCGA | CGCTCAAGTC | AGAGGTGGCG | AAACCCGACA | GGACTATAAA |
| 17300 | 17310 | 17320 | 17330 | 17340 | 17350 | 17360 |
| GATACCAGGC | GTTTCCCCCT | GGAAGCTCCC | TCGTGCGCTC | TCCTGTTCCG | ACCCTGCCGC | TTACCGGATA |
| 17370 | 17380 | 17390 | 17400 | 17410 | 17420 | 17430 |
| CCTGTCCGCC | TTTCTCCCTT | CGGGAAGCGT | GGCGCTTTCT | CATAGCTCAC | GCTGTAGGTA | TCTCAGTTCG |
| 17440 | 17450 | 17460 | 17470 | 17480 | 17490 | 17500 |
| GTGTAGGTCG | TTCGCTCCAA | GCTGGGCTGT | GTGCACGAAC | CCCCCGTTCA | GCCCGACCGC | TGCGCCTTAT |
| 17510 | 17520 | 17530 | 17540 | 17550 | 17560 | 17570 |
| CCGGTAACTA | TCGTCTTGAG | TCCAACCCGG | TAAGACACGA | CTTATCGCCA | CTGGCAGCAG | CCACTGGTAA |
| 17580 | 17590 | 17600 | 17610 | 17620 | 17630 | 17640 |
| CAGGATTAGC | AGAGCGAGGT | ATGTAGGCGG | TGCTACAGAG | TTCTTGAAGT | GGTGGCCTAA | CTACGGCTAC |

FIG. 10S

| | | | | | | |
|---|---|---|---|---|---|---|
| 17650 | 17660 | 17670 | 17680 | 17690 | 17700 | 17710 |
| ACTAGAAGGA | CAGTATTTGG | TATCTGCGCT | CTGCTGAAGC | CAGTTACCTT | CGGAAAAAGA | GTTGGTAGCT |
| 17720 | 17730 | 17740 | 17750 | 17760 | 17770 | 17780 |
| CTTGATCCGG | CAAACAAACC | ACCGCTGGTA | GCGGTGGTTT | TTTTGTTTGC | AAGCAGCAGA | TTACGCGCAG |
| 17790 | 17800 | 17810 | 17820 | 17830 | 17840 | 17850 |
| AAAAAAAGGA | TCTCAAGAAG | ATCCTTTGAT | CTTTTCTACG | GGGTCTGACG | CTCAGTGGAA | CGAAAACTCA |
| 17860 | 17870 | 17880 | 17890 | 17900 | 17910 | 17920 |
| CGTTAAGGGA | TTTTGGTCAT | GAGATTATCA | AAAAGGATCT | TCACCTAGAT | CCTTTTAAAT | TAAAAATGAA |
| 17930 | 17940 | 17950 | 17960 | 17970 | 17980 | 17990 |
| GTTTTAAATC | AATCTAAAGT | ATATATGAGT | AAACTTGGTC | TGACAGTTAC | CAATGCTTAA | TCAGTGAGGC |
| 18000 | 18010 | 18020 | 18030 | 18040 | 18050 | 18060 |
| ACCTATCTCA | GCGATCTGTC | TATTTCGTTC | ATCCATAGTT | GCCTGACTCC | CCGTCGTGTA | GATAACTACG |
| 18070 | 18080 | 18090 | 18100 | 18110 | 18120 | 18130 |
| ATACGGGAGG | GCTTACCATC | TGGCCCCAGT | GCTGCAATGA | TACCGCGAGA | CCCACGCTCA | CCGGCTCCAG |
| 18140 | 18150 | 18160 | 18170 | 18180 | 18190 | 18200 |
| ATTTATCAGC | AATAAACCAG | CCAGCCGGAA | GGGCCGAGCG | CAGAAGTGGT | CCTGCAACTT | TATCCGCCTC |
| 18210 | 18220 | 18230 | 18240 | 18250 | 18260 | 18270 |
| CATCCAGTCT | ATTAATTGTT | GCCGGGAAGC | TAGAGTAAGT | AGTTCGCCAG | TTAATAGTTT | GCGCAACGTT |
| 18280 | 18290 | 18300 | 18310 | 18320 | 18330 | 18340 |
| GTTGCCATTG | CTGCAGGCAT | CGTGGTGTCA | CGCTCGTCGT | TTGGTATGGC | TTCATTCAGC | TCCGGTTCCC |
| 18350 | 18360 | 18370 | 18380 | 18390 | 18400 | 18410 |
| AACGATCAAG | GCGAGTTACA | TGATCCCCCA | TGTTGTGCAA | AAAAGCGGTT | AGCTCCTTCG | GTCCTCCGAT |
| 18420 | 18430 | 18440 | 18450 | 18460 | 18470 | 18480 |
| CGTTGTCAGA | AGTAAGTTGG | CCGCAGTGTT | ATCACTCATG | GTTATGGCAG | CACTGCATAA | TTCTCTTACT |
| 18490 | 18500 | 18510 | 18520 | 18530 | 18540 | 18550 |
| GTCATGCCAT | CCGTAAGATG | CTTTTCTGTG | ACTGGTGAGT | ACTCAACCAA | GTCATTCTGA | GAATAGTGTA |
| 18560 | 18570 | 18580 | 18590 | 18600 | 18610 | 18620 |
| TGCGGCGACC | GAGTTGCTCT | TGCCCGGCGT | CAACACGGGA | TAATACCGCG | CCACATAGCA | GAACTTTAAA |

FIG. 10T

```
     18630      18640      18650      18660      18670      18680      18690
AGTGCTCATC ATTGGAAAAC GTTCTTCGGG GCGAAAACTC TCAAGGATCT TACCGCTGTT GAGATCCAGT
     18700      18710      18720      18730      18740      18750      18760
TCGATGTAAC CCACTCGTGC ACCCAACTGA TCTTCAGCAT CTTTTACTTT CACCAGCGTT TCTGGGTGAG
     18770      18780      18790      18800      18810      18820      18830
CAAAAACAGG AAGGCAAAAT GCCGCAAAAA AGGGAATAAG GGCGACACGG AAATGTTGAA TACTCATACT
     18840      18850      18860      18870      18880      18890      18900
CTTCCTTTTT CAATATTATT GAAGCATTTA TCAGGGTTAT TGTCTCATGA GCGGATACAT ATTTGAATGT
     18910      18920      18930      18940      18950      18960      18970
ATTTAGAAAA ATAAACAAAT AGGGGTTCCG CGCACATTTC CCCGAAAAGT GCCACCTGAC GTCTAAGAAA
     18980      18990      19000      19010      19020      19030      19040
CCATTATTAT CATGACATTA ACCTATAAAA ATAGGCGTAT CACGAGGCCC TTTCGTCTTC AAGAA. . . .
     19050      19060      19070      19080
```

FIG. 10U

```
                         SEQUENCE LISTING

<160> NUMBER OF SEQ ID NOS: 3

<210> SEQ ID NO 1
<211> LENGTH: 14683
<212> TYPE: DNA
<213> ORGANISM: Artificial Sequence
<220> FEATURE:
<223> OTHER INFORMATION: Description of Artificial Sequence: Synthetic
      DNA referred to as "Desmond"

<400> SEQUENCE: 1

tttctagacc tagggcggcc agctagtagc tttgcttctc aatttcttat ttgcataatg     60

agaaaaaaag gaaaattaat tttaacacca attcagtagt tgattgagca aatgcgttgc    120

caaaaaggat gctttagaga cagtgttctc tgcacagata aggacaaaca ttattcagag    180

ggagtaccca gagctgagac tcctaagcca gtgagtggca cagcattcta gggagaaata    240

tgcttgtcat caccgaagcc tgattccgta gagccacacc ttggtaaggg ccaatctgct    300

cacacaggat agagagggca ggagccaggg cagagcatat aaggtgaggt aggatcagtt    360

gctcctcaca tttgcttctg acatagttgt gttgggagct tggatagctt ggacagctca    420

gggctgcgat ttcgcgccaa acttgacggc aatcctagcg tgaaggctgg taggatttta    480

tccccgctgc catcatggtt cgaccattga actgcatcgt cgccgtgtcc caaaatatgg    540

ggattggcaa gaacggagac ctaccctggc ctccgctcag gaacgagttc aagtacttcc    600

aaagaatgac cacaacctct tcagtggaag gtaaacagaa tctggtgatt atgggtagga    660

aaacctggtt ctccattcct gagaagaatc gacctttaaa ggacagaatt aatatagttc    720

tcagtagaga actcaaagaa ccaccacgag gagctcattt tcttgccaaa agtttggatg    780

atgccttaag acttattgaa caaccggaat tggcaagtaa agtagacatg gtttggatag    840

tcggaggcag ttctgtttac caggaagcca tgaatcaacc aggccacctt agactctttg    900

tgacaaggat catgcaggaa tttgaaagtg acacgttttt cccagaaatt gatttgggga    960

aatataaact tctcccagaa tacccaggcg tcctctctga ggtccaggag gaaaaaggca   1020

tcaagtataa gtttgaagtc tacgagaaga aagactaaca ggaagatgct ttcaagttct   1080

ctgctcccct cctaaagcta tgcattttta taagaccatg ggacttttgc tggctttaga   1140
```

-continued

```
tcagcctcga ctgtgccttc tagttgccag ccatctgttg tttgcccctc ccccgtgcct   1200
tccttgaccc tggaaggtgc cactcccact gtcctttcct aataaaatga ggaaattgca   1260
tcgcattgtc tgagtaggtg tcattctatt ctggggggtg gggtggggca ggacagcaag   1320
ggggaggatt gggaagacaa tagcaggcat gctggggatg cggtgggctc tatggaacca   1380
gctggggctc gaagcggccg cccatttcgc tggtggtcag atgcgggatg gcgtgggacg   1440
cggcggggac cgtcacactg aggttttccg ccagacgcca ctgctgccag gcgctgatgt   1500
gcccggcttc tgaccatgcg gtcgcgttcg gttgcactac gcgtactgtg agccagagtt   1560
gcccggcgct ctccggctgc ggtagttcag gcagttcaat caactgttta ccttgtggag   1620
cgacatccag aggcacttca ccgcttgcta gcggcttacc atccagcgcc accatccagt   1680
gcaggagctc gttatcgcta tgacggaaca ggtattcgct ggtcacttcg atggtttgcc   1740
cggataaacg gaactggaaa aactgctgct ggtgttttgc ttccgtcagc gctggatgcg   1800
gcgtgcggtc ggcaaagacc agaccgttca tacagaactg gcgatcgttc ggcgtatcac   1860
caaaatcacc gccgtaagcc gaccacgggt tgccgttttc atcatattta atcagcgact   1920
gatccaccca gtcccagacg aagccgccct gtaaacgggg atactgacga aacgcctgcc   1980
agtatttagc gaaaccgcca agactgttac ccatcgcgtg ggcgtattcg caaaggatca   2040
gcgggcgcgt ctctccgggt agcgaaagcc atttttgat ggaccatttc ggaccagccg   2100
ggaagggctg gtcttcatcc acgcgcgcgt acatcgggca aataatatcg gtggccgtgg   2160
tgtcggctcc gccgccttca tactgcaccg ggcgggaagg atcgacagat ttgatccagc   2220
gatacagcgc gtcgtgatta gcgccgtggc ctgattcatt ccccagcgac cagatgatca   2280
cactcgggtg attacgatcg cgctgcacca ttcgcgttac gcgttcgctc atcgccggta   2340
gccagcgcgg atcatcggtc agacgattca ttggcaccat gccgtgggtt tcaatattgg   2400
cttcatccac cacatacagg ccgtagcggt cgcacagcgt gtaccacagc ggatggttcg   2460
gataatgcga acagcgcacg gcgttaaagt tgttctgctt catcagcagg atatcctgca   2520
ccatcgtctg ctcatccatg acctgaccat gcagaggatg atgctcgtga cggttaacgc   2580
ctcgaatcag caacggcttg ccgttcagca gcagcagacc atttccaatc cgcacctcgc   2640
ggaaaccgac atcgcaggct tctgcttcaa tcagcgtgcc gtcggcggtg tgcagttcaa   2700
ccaccgcacg atagagattc gggatttcgg cgctccacag tttcgggttt tcgacgttca   2760
gacgcagtgt gacgcgatcg gcataaccac caggctcatc gataatttca ccgccgaaag   2820
gcgcggtgcc gctggcgacc tgcgtttcac cctgccataa agaaactgtt acccgtaggt   2880
agtcacgcaa ctcgccgcac atctgaactt cagcctccag tacagcgcgg ctgaaatcat   2940
cattaaagcg agtggcaaca tggaaatcgc tgatttgtgt agtcggttta tgcagcaacg   3000
agacgtcacg gaaaatgccg ctcatccgcc acatatcctg atcttccaga taactgccgt   3060
cactccaacg cagcaccatc accgcgaggc ggttttctcc ggcgcgtaaa aatgcgctca   3120
ggtcaaattc agacggcaaa cgactgtcct ggctgtaacc gacccacgcc ccgttgcacc   3180
acagatgaaa cgccgagtta acgccatcaa aaataattcg cgtctggcct tcctgtagcc   3240
agctttcatc aacattaaat gtgagcgagt aacaacccgt cggattctcc gtgggaacaa   3300
acggcggatt gaccgtaatg ggataggtta cgttggtgta gatgggcgca tcgtaaccgt   3360
gcatctgcca gtttgagggg acgacgacag tatcggcctc aggaagatcg cactccagcc   3420
agctttccgg cactgcttct ggtgccggaa accaggcaaa gcgccattcg ccattcaggc   3480
```

-continued

```
tgcgcaactg ttgggaaggg cgatcggtgc gggcctcttc gctattacgc cagctggcga   3540
aagcgggatg tgctgcaagg cgattaagtt gggtaacgcc agggttttcc cagtcacgac   3600
gttgtaaaac gacttaatcc gtcgaggggc tgcctcgaag cagacgacct tccgttgtgc   3660
agccagcggc gcctgcgccg gtgcccacaa tcgtgcgcga acaaactaaa ccagaacaaa   3720
tcataccggc ggcaccgccg ccaccacctt ctcctgtgcc taacattcca gcgcctccac   3780
cactaccacc accatcgatg tctgaattgc cgcccgctcc accaatgccg acggaacctc   3840
aacccgctgc acctttagac gacagacaac aattgttgga agctattaga aacgaaaaaa   3900
atcgcactcg tctcagaccg gctctcttaa ggtagctcaa accaaaaacg gcgcccgaaa   3960
ccagtacaat agttgaggtg ccgactgtgt tgcctaaaga gacatttgag cttaaaccgc   4020
cgtctgcacc accgccacca cctccgcctc cgcctccgcc gccagccccg cctgcgcctc   4080
caccgatggt agattcatca tcagctccac caccgccgcc attagtagat ttgccgtctg   4140
aaatgttacc accgcctgca ccatcgcttt ctaacgtgtt gtctgaatta aaatcgggca   4200
cagttagatt gaaacccgcc caaaaacgcc cgcaatcaga aataattcca aaaagctcaa   4260
ctacaaattt gatcgcggac gtgttagccg acacaattaa taggcgtcgt gtggctatgg   4320
caaaatcgtc ttcggaagca acttctaacg acgagggttg ggacgacgac gataatcggc   4380
ctaataaagc taacacgccc gatgttaaat atgtccaagc tactagtggt accttaatta   4440
aggggcggag aatgggcgga actgggcgga gttaggggcg ggatgggcgg agttaggggc   4500
gggactatgg ttgctgacta attgagatgc atgctttgca tacttctgcc tgctggggag   4560
cctggggact ttccacacct ggttgctgac taattgagat gcatgctttg catacttctg   4620
cctgctgggg agcctgggga ctttccacac cctaactgac acacattcca cagaattaat   4680
tcccctagtt attaatagta atcaattacg gggtcattag ttcatagccc atatatggag   4740
ttccgcgtta cataacttac ggtaaatggc ccgcctggct gaccgctcaa cgacccccgc   4800
ccattgacgt caataatgac gtatgttccc atagtaacgc caatagggac tttccattga   4860
cgtcaatggg tggactattt acggtaaact gcccacttgg cagtacatca agtgtatcat   4920
atgccaagta cgccccctat tgacgtcaat gacggtaaat ggcccgcctg gcattatgcc   4980
cagtacatga ccttatggga ctttcctact tggcagtaca tctacgtatt agtcatcgct   5040
attaccatgg tgatgcggtt ttggcagtac atcaatgggc gtggatagcg gtttgactca   5100
cggggatttc caagtctcca ccccattgac gtcaatggga gtttgttttg aagcttggcc   5160
ggccatataa acggcggcca gctttattta acgtgtttac gtcgagtcaa ttgtacacta   5220
acgacagtga tgaaagaaat acaaaagcgc ataatatttt gaacgacgtc gaacctttat   5280
tacaaaacaa aacacaaacg aatatcgaca aagctagatt gctgctacaa gatttggcaa   5340
gttttgtggc gttgagcgaa aatccattag atagtccagc catcggttcg gaaaaacaac   5400
ccttgtttga aactaatcga aacctatttt acaaatctat tgaggattta atatttaaat   5460
tcagatataa agacgctgaa aatcatttga ttttcgctct aacataccac cctaaagatt   5520
ataaatttaa tgaattatta aaatacatca gcaactatat attgatagac atttccagtt   5580
tgtgatatta gtttgtgcgt ctcattacaa tggctgttat ttttaacaac aaacaactgc   5640
tcgcagacaa tagtatagaa aagggaggtg aactgttttt gtttaacggt tcgtacaaca   5700
ttttggaaag ttatgttaat ccggtgctgc taaaaaatgg tgtaattgaa ctagaagaag   5760
ctgcgtacta tgccggcaac atattgtaca aaaccgacga tcccaaattc attgattata   5820
taaatttaat aattaaagca acacactccg aagaactacc agaaaatagc actgttgtaa   5880
```

-continued

```
attacagaaa aactatgcgc agcggtacta tacaccccat taaaaaagac atatatattt   5940
atgacaacaa aaaatttact ctatacgata gatacatata tggatacgat aataactatg   6000
ttaattttta tgaggagaaa aatgaaaaag agaaggaata cgaagaagaa gacgacaagg   6060
cgtctagttt atgtgaaaat aaaattatat tgtcgcaaat taactgtgaa tcatttgaaa   6120
atgattttaa atattacctc agcgattata actacgcgtt ttcaattata gataacacta   6180
caaatgttct tgttgcgttt ggtttgtatc gttaataaaa aacaaattta gcatttataa   6240
ttgttttatt attcaataat tacaaatagg attgagaccc ttgcagttgc cagcaaacgg   6300
acagagcttg tcgaggagag ttgttgattc attgtttgcc tccctgctgc ggtttttgac   6360
cgaagttcat gccagtccag cgtttttgca gcagaaaagc cgccgacttc ggtttgcggt   6420
cgcgagtgaa gatccctttc ttgttaccgc caacgcgcaa tatgccttgc gaggtcgcaa   6480
aatcggcgaa attccatacc tgttcaccga cgacggcgct gacgcgatca aagacgcggt   6540
gatacatatc cagccatgca cactgatact cttcactcca catgtcggtg tacattgagt   6600
gcagcccggc taacgtatcc acgccgtatt cggtgatgat aatcggctga tgcagtttct   6660
cctgccaggc cagaagttct ttttccagta ccttctctgc cgtttccaaa tcgccgcttt   6720
ggacatacca tccgtaataa cggttcaggc acagcacatc aaagagatcg ctgatggtat   6780
cggtgtgagc gtcgcagaac attacattga cgcaggtgat cggacgcgtc gggtcgagtt   6840
tacgcgttgc ttccgccagt ggcgcgaaat attcccgtgc accttgcgga cgggtatccg   6900
gttcgttggc aatactccac atcaccacgc ttgggtggtt tttgtcacgc gctatcagct   6960
ctttaatcgc ctgtaagtgc gcttggtgag tttccccgtt gactgcctct tcgttgtaca   7020
gttctttcgg cttgttgccc gcttcgaaac caatgcctaa agagaggtta aagccgacag   7080
cagcagtttc atcaatcacc acgatgccat gttcatctgc ccagtcgagc atctcttcag   7140
cgtaagggta atgcgaggta cggtaggagt tggccctaat ccagtccatt aatgcgtggt   7200
cgtgcaccat cagcacgtta tcgaatcctt tgccacgcaa gtccgcatct tcatgacgac   7260
caaagccagt aaagtagaac ggtttgtggt taatcaggaa ctgttcgccc ttcactgcca   7320
ctgaccggat gccgacgcga agcgggtaga tatcacactc tgtctggctt ttggctgtga   7380
cgcacagttc atagagataa ccttcacccg gttgccagag gtgcggattc accacttgca   7440
aagtcccgct agtgccttgt ccagttgcaa ccacctgttg atccgcatca cgcagttcaa   7500
cgctgacatc accattggcc accacctgcc agtcaacaga cgcgtggtta cagtcttgcg   7560
cgacatgcgt cactacggtg atatcgtcca cccaggtgtt cggcgtggtg tagagcatta   7620
cgctgcgatg gattccggca tagttaaaga aatcatggaa gtaagattgc tttttcttgc   7680
cgttttcgtt ggtaatcacc attcccggcg ggatagtctg ccagttcagt tcgttgttca   7740
cacaaacggt gatacccctc gacggattaa agacttcaag cggtcaacta tgaagaagtg   7800
ttcgtcttcg tcccagtaag ctatgtctct agaatgtagc catccatcct tgtcaatcaa   7860
ggcgttggtc gcttccggat tgtttacata accggacata atcataggtc ctctgacaca   7920
taatacgcct ctctgattaa cgcccagcgt ttcccggta tccagatcca caaccttcgc   7980
ttcaaaaaat ggaacaactt taccgaccgc gcccggttta tcatccccct cgggtgtaat   8040
cagaatagct gatgtagtct cagtgagccc atatccttgt cgtatccctg gaagatggaa   8100
gcgttttgca accgcttccc cgactttcttt cgaaagaggt gcgcccccag aagcaatttc   8160
gtgtaaatta gataaatcgt atttgtcaat cagagtgctt ttggcgaaga atgaaaatag   8220
```

-continued

```
ggttggtact agcaacgcac tttgaatttt gtaatcctga agggatcgta aaaacagctc   8280
ttcttcaaat ctatacatta agacgactcg aaatctacat atcaaatatc cgagtgtagt   8340
aaacattcca aaaccgtgat ggaatggaac aacacttaaa atcgcagtat ccggaatgat   8400
ttgattgcca aaaataggat ctctggcatg cgagaatcta gcgcaggcag ttctatgcgg   8460
aagggccaca cccttaggta acccagtaga tccagaggaa ttgttttgtc acgatcaaag   8520
gactctggta caaaatcgta ttcattaaaa ccgggaggta gatgagatgt gacgaaggtg   8580
tacatcgact gaaatccctg gtaatccgtt ttagaatcca tgataataat tttctggatt   8640
attggtaatt ttttttgcac gttcaaaatt ttttgcaacc ccttttttgga aacaaacact   8700
acggtaggct gcgaaatgtt catactgttg agcaattcac gttcattata aatgtcgttc   8760
gcgggcgcaa ctgcaactcc gataaataac gcgcccaaca ccggcataaa gaattgaaga   8820
gagttttcac tgcatacgac gattctgtga tttgtattca gcccatatcg tttcatagct   8880
tctgccaacc gaacggacat ttcgaagtat tccgcgtacg tgatgttcac ctcgatatgt   8940
gcatctgtaa aaggaattgt tccaggaacc agggcgtatc tcttcatagc cttatgcagt   9000
tgctctccag cggttccatt ctctagcttt gcttctcaat ttcttatttg cataatgaga   9060
aaaaaaggaa aattaatttt aacaccaatt cagtagttga ttgagcaaat gcgttgccaa   9120
aaaggatgct ttagagacag tgttctctgc acagataagg acaaacatca ttcagaggga   9180
gtacccagag ctgagactcc taagccagtg agtggcacag cattctaggg agaaatatgc   9240
ttgtcatcac cgaagcctga ttccgtagag ccacaccttg gtaagggcca atctgctcac   9300
acaggataga gagggcagga gccagggcag agcatataag gtgaggtagg atcagttgct   9360
cctcacattt gcttctgaca tagttgtgtt gggagcttgg atcgatccac catgggcttc   9420
aataccctga ttgactggaa cagctgtagc cctgaacagc agcgtgcgct gctgacgcgt   9480
ccggcgattt ccgcctctga cagtattacc cggacggtca gcgatattct ggataatgca   9540
aaaacgcgcg gtgacgatgc cctgcgtgaa tacagcgcta aatttgataa aacagaagtg   9600
acagcgctac gcgtcacccc tgaagagatc gccgccgccg gcgcgcgtct gagcgacgaa   9660
ttaaaacagg cgatgaccgc tgccgtcaaa aatattgaaa cgttccattc cgcgcagacg   9720
ctaccgcttg tagatgtgga aacccagcca ggcgtgcgtt gccagcaggt tacgcgtccc   9780
gtctcgtctg tcggtctgta tattcccggc ggctcggctc cgctcttctc aacggtgctg   9840
atgctggcga cgccggcgcg cattgcggga tgctagaagg tggttctgtg ctcgccgccg   9900
cccatcgctg atgaaatcct ctatgcggcg caactgtgtg gcgtgcagga attctttaac   9960
ctcggcggcg cgcaggcgat tgccgctctg gccttcggca gcgagtccgt accgaaagtg  10020
gataaaattt ttggccccgg caacgccttt gtaaccgaag ccaaacgtca ggtcagccag  10080
cgtctcgacg gcgcggctat cgatatgcca gccgagccgt ctgaagtact ggtgatcgca  10140
gacagcggcg caacaccgga tttcgtcgct tctgacctgc tctcccagac tgagcacggc  10200
ccggattccc aggtgatcct gctgacgcct gatgctgaca ttgcccgcaa ggtggcggag  10260
gcggtagaac gtcaactggc ggaactgccg cgcgcggaca ccgcctggca ggccctgagc  10320
gccagtcgtc tgattgtgac caaagattta gcgcagtgcg tcgccatctc taatcagtat  10380
gggccggaac acttaatcat ccagacgcgc aatgcgcgcg atttggtgga tgcgattacc  10440
agcgcaggct cggtatttct cggcgactgg tcgccggaat ccgccggtga ttacgcttcc  10500
ggaaccaacc atgttttacc gacctatggc catactgcta cctgttccag ccttgggtta  10560
gcggatttcc agaaacggat gaccgttcag gaactgtcga aagcgggctt ttccgctctg  10620
```

-continued

```
gcatcaacca ttgaaacatt ggcgggggca gaacgtctga ccgcccataa aaatgccgtg  10680
accctgcgcg taaacgccct caaggagcaa gcatgagcac tgaaaacact ctcagcgtcg  10740
ctgacttagc ccgtgaaaat gtccgcaacc tggagatcca gacatgataa gatacattga  10800
tgagtttgga caaaccacaa ctagaatgca gtgaaaaaaa tgctttattt gtgaaatttg  10860
tgatgctatt gctttatttg taaccattat aagctgcaat aaacaagtta acaacaacaa  10920
ttgcattcat tttatgtttc aggttcaggg ggaggtgtgg gaggtttttt aaagcaagta  10980
aaacctctac aaatgtggta tggctgatta tgatctctag ctcgacgggg cgcctggccg  11040
ctactaactc tctcctccct cctttttcct gcaggctcaa ggcgcgcatg cccgacggcg  11100
aggatctcgt cgtgacccat ggcgatgcct gcttgccgaa tatcatggtg gaaaatggcc  11160
gcttttctgg attcatcgac tgtggccggc tgggtgtggc ggaccgctat caggacatag  11220
cgttggctac ccgtgatatt gctgaagagc ttggcggcga atgggctgac cgcttcctcg  11280
tgctttacgg tatcgccgct cccgattcgc agcgcatcgc cttctatcgc cttcttgacg  11340
agttcttctg agcgggactc tggggttcga aatgaccgac caagcgacgc ccaacctgcc  11400
atcacgagat ttcgattcca ccgccgcctt ctatgaaagg ttgggcttcg gaatcgtttt  11460
ccgggacgcc ggctggatga tcctccagcg cggggatctc atgctggagt tcttcgccca  11520
ccccaacttg tttattgcag cttataatgg ttacaaataa agcaatagca tcacaaattt  11580
cacaaataaa gcattttttt cactgcattc tagttgtggt ttgtccaaac tcatcaatct  11640
atcttatcat gtctggatcg cggccggtct ctctctagcc ctaggtctag acttggcaga  11700
acatatccat cgcgtccgcc atctccagca gccgcacgcg gcgcatctcg ggcagcgttg  11760
ggtcctggcc acgggtgcgc atgatcgtgc tcctgtcgtt gaggacccgg ctaggctggc  11820
ggggttgcct tactggttag cagaatgaat caccgatacg cgagcgaacg tgaagcgact  11880
gctgctgcaa aacgtctgcg acctgagcaa caacatgaat ggtcttcggt ttccgtgttt  11940
cgtaaagtct ggaaacgcgg aagtcagcgc cctgcaccat tatgttccgg atctgcatcg  12000
caggatgctg ctggctaccc tgtggaacac ctacatctgt attaacgaag cgctggcatt  12060
gaccctgagt gatttttctc tggtcccgcc gcatccatac cgccagttgt ttaccctcac  12120
aacgttccag taaccgggca tgttcatcat cagtaacccg tatcgtgagc atcctctctc  12180
gtttcatcgg tatcattacc cccatgaaca gaaatccccc ttacacggag gcatcagtga  12240
ccaaacagga aaaaaccgcc cttaacatgg cccgctttat cagaagccag acattaacgc  12300
ttctggagaa actcaacgag ctggacgcgg atgaacaggc agacatctgt gaatcgcttc  12360
acgaccacgc tgatgagctt taccgcagct gcctcgcgcg tttcggtgat gacggtgaaa  12420
acctctgaca catgcagctc ccggagacgg tcacagcttg tctgtaagcg gatgccggga  12480
gcagacaagc ccgtcagggc gcgtcagcgg gtgttggcgg gtgtcggggc gcagccatga  12540
cccagtcacg tagcgatagc ggagtgtata ctggcttaac tatgcggcat cagagcagat  12600
tgtactgaga gtgcaccata tgcggtgtga aataccgcac agatgcgtaa ggagaaaata  12660
ccgcatcagg cgctcttccg cttcctcgct cactgactcg ctgcgctcgg tcgttcggct  12720
gcggcgagcg gtatcagctc actcaaaggc ggtaatacgg ttatccacag aatcagggga  12780
taacgcagga aagaacatgt gagcaaaagg ccagcaaaag gccaggaacc gtaaaaaggc  12840
cgcgttgctg gcgtttttcc ataggctccg cccccctgac gagcatcaca aaaatcgacg  12900
ctcaagtcag aggtggcgaa acccgacagg actataaaga taccaggcgt ttccccctgg  12960
```

-continued

```
aagctccctc gtgcgctctc ctgttccgac cctgccgctt accggatacc tgtccgcctt  13020

tctcccttcg ggaagcgtgg cgctttctca tagctcacgc tgtaggtatc tcagttcggt  13080

gtaggtcgtt cgctccaagc tgggctgtgt gcacgaaccc cccgttcagc ccgaccgctg  13140

cgccttatcc ggtaactatc gtcttgagtc caacccggta agacacgact tatcgccact  13200

ggcagcagcc actggtaaca ggattagcag agcgaggtat gtaggcggtg ctacagagtt  13260

cttgaagtgg tggcctaact acggctacac tagaaggaca gtatttggta tctgcgctct  13320

gctgaagcca gttaccttcg gaaaaagagt tggtagctct tgatccggca aacaaaccac  13380

cgctggtagc ggtggttttt ttgtttgcaa gcagcagatt acgcgcagaa aaaaaggatc  13440

tcaagaagat cctttgatct tttctacggg gtctgacgct cagtggaacg aaaactcacg  13500

ttaagggatt ttggtcatga gattatcaaa aaggatcttc acctagatcc ttttaaatta  13560

aaaatgaagt tttaaatcaa tctaaagtat atatgagtaa acttggtctg acagttacca  13620

atgcttaatc agtgaggcac ctatctcagc gatctgtcta tttcgttcat ccatagttgc  13680

ctgactcccc gtcgtgtaga taactacgat acgggagggc ttaccatctg gccccagtgc  13740

tgcaatgata ccgcgagacc cacgctcacc ggctccagat ttatcagcaa taaaccagcc  13800

agccggaagg gccgagcgca gaagtggtcc tgcaacttta tccgcctcca tccagtctat  13860

taattgttgc cgggaagcta gagtaagtag ttcgccagtt aatagtttgc gcaacgttgt  13920

tgccattgct gcaggcatcg tggtgtcacg ctcgtcgttt ggtatggctt cattcagctc  13980

cggttcccaa cgatcaaggc gagttacatg atcccccatg ttgtgcaaaa aagcggttag  14040

ctccttcggt cctccgatcg ttgtcagaag taagttggcc gcagtgttat cactcatggt  14100

tatggcagca ctgcataatt ctcttactgt catgccatcc gtaagatgct tttctgtgac  14160

tggtgagtac tcaaccaagt cattctgaga atagtgtatg cggcgaccga gttgctcttg  14220

cccggcgtca acacgggata ataccgcgcc acatagcaga actttaaaag tgctcatcat  14280

tggaaaacgt tcttcggggc gaaaactctc aaggatctta ccgctgttga gatccagttc  14340

gatgtaaccc actcgtgcac ccaactgatc ttcagcatct tttactttca ccagcgtttc  14400

tgggtgagca aaaacaggaa ggcaaaatgc cgcaaaaaag ggaataaggg cgacacggaa  14460

atgttgaata ctcatactct tcctttttca atattattga agcatttatc agggttattg  14520

tctcatgagc ggatacatat ttgaatgtat ttagaaaaat aaacaaatag gggttccgcg  14580

cacatttccc cgaaaagtgc cacctgacgt ctaagaaacc attattatca tgacattaac  14640

ctataaaaat aggcgtatca cgaggccctt tcgtcttcaa gaa                     14683
```

```
<210> SEQ ID NO 2
<211> LENGTH: 18986
<212> TYPE: DNA
<213> ORGANISM: Artificial Sequence
<220> FEATURE:
<223> OTHER INFORMATION: Description of Artificial Sequence: Synthetic
      DNA referred to as "Molly"

<400> SEQUENCE: 2

ttaattaagg ggcggagaat gggcggaact gggcggagtt aggggcggga tgggcggagt     60

taggggcggg actatggttg ctgactaatt gagatgcatg ctttgcatac ttctgcctgc    120

tggggagcct ggggactttc cacacctggt tgctgactaa ttgagatgca tgctttgcat    180

acttctgcct gctggggagc ctggggactt tccacaccct aactgacaca cattccacag    240

aattaattcc cctagttatt aatagtaatc aattacgggg tcattaggtc atagcccata    300
```

-continued

```
tatggagttc cgcgttacat aacttacggt aaatggcccg cctggctgac cgcccaacga    360
cccccgccca ttgacgtcaa taatgacgta tgttcccata gtaacgccaa tagggacttt    420
ccattgacgt caatgggtgg actatttacg gtaaactgcc cacttggcag tacatcaagt    480
gtatcatatg ccaagtacgc cccctattga cgtcaatgac ggtaaatggc ccgcctggca    540
ttatgcccag tacatgacct tatgggactt tcctacttgg cagtacatct acgtattagt    600
catcgctatt accatggtga tgcggttttg gcagtacatc aatgggcgtg gatagcggtt    660
tgactcacgg ggatttccaa gtctccaccc cattgacgtc aatgggagtt tgttttgaag    720
cttggccggc catataaacg gcggccagct ttatttaacg tgtttacgtc gagtcaattg    780
tacactaacg acagtgatga aagaaataca aaagcgcata atattttgaa cgacgtcgaa    840
cctttattac aaaacaaaac acaaacgaat atcgacaaag ctagattgct gctacaagat    900
ttggcaagtt ttgtggcgtt gagcgaaaat ccattagata gtccagccat cggttcggaa    960
aaacaaccct tgtttgaaac taatcgaaac ctattttaca aatctattga ggatttaata   1020
tttaaattca gatataaaga cgctgaaaat catttgattt tcgctctaac ataccaccct   1080
aaagattata aatttaatga attattaaaa tacatcagca actatatatt gatagacatt   1140
tccagtttgt gatattagtt tgtgcgtctc attacaatgg ctgttatttt taacaacaaa   1200
caactgctcg cagacaatag tatagaaaag ggaggtgaac tgtttttgtt taacggttcg   1260
tacaacattt tggaaagtta tgttaatccg gtgctgctaa aaaatggtgt aattgaacta   1320
gaagaagctg cgtactatgc cggcaacata ttgtacaaaa ccgacgatcc caaattcatt   1380
gattatataa atttaataat taaagcaaca cactccgaag aactaccaga aaatagcact   1440
gttgtaaatt acagaaaaac tatgcgcagc ggtactatac accccattaa aaaagacata   1500
tatatttatg acaacaaaaa atttactcta tacgatagat acatatatgg atacgataat   1560
aactatgtta atttttatga ggagaaaaat gaaaaagaga aggaatacga agaagaagac   1620
gacaaggcgt ctagtttatg tgaaaataaa attatattgt cgcaaattaa ctgtgaatca   1680
tttgaaaatg attttaaata ttacctcagc gattataact acgcgttttc aattatagat   1740
aatactacaa atgttcttgt tgcgtttggt ttgtatcgtt aataaaaaac aaatttagca   1800
tttataattg ttttattatt caataattac aaataggatt gagacccttg cagttgccag   1860
caaacggaca gagcttgtcg aggagagttg ttgattcatt gtttgcctcc ctgctgcggt   1920
ttttcaccga agttcatgcc agtccagcgt ttttgcagca gaaaagccgc cgacttcggt   1980
ttgcggtcgc gagtgaagat ccctttcttg ttaccgccaa cgcgcaatat gccttgcgag   2040
gtcgcaaaat cggcgaaatt ccatacctgt tcaccgacga cggcgctgac gcgatcaaag   2100
acgcggtgat acatatccag ccatgcacac tgatactctt cactccacat gtcggtgtac   2160
attgagtgca gcccggctaa cgtatccacg ccgtattcgg tgatgataat cggctgatgc   2220
agtttctcct gccaggccag aagttctttt tccagtacct tctctgccgt ttccaaatcg   2280
ccgctttgga cataccatcc gtaataacgg ttcaggcaca gcacatcaaa gagatcgctg   2340
atggtatcgg tgtgagcgtc gcagaacatt acattgacgc aggtgatcgg acgcgtcggg   2400
tcgagtttac gcgttgcttc cgccagtggc gcgaaatatt cccgtgcacc ttgcggacgg   2460
gtatccggtt cgttggcaat actccacatc accacgcttg ggtggttttt gtcacgcgct   2520
atcagctctt taatcgcctg taagtgcgct tgctgagttt ccccgttgac tgcctcttcg   2580
ctgtacagtt ctttcggctt gttgcccgct tcgaaaccaa tgcctaaaga gaggttaaag   2640
ccgacagcag cagtttcatc aatcaccacg atgccatgtt catctgccca gtcgagcatc   2700
```

-continued

```
tcttcagcgt aagggtaatg cgaggtacgg taggagttgg ccccaatcca gtccattaat   2760
gcgtggtcgt gcaccatcag cacgttatcg aatcctttgc cacgcaagtc cgcatcttca   2820
tgacgaccaa agccagtaaa gtagaacggt ttgtggttaa tcaggaactg ttcgcccttc   2880
actgccactg accggatgcc gacgcgaagc gggtagatat cacactctgt ctggcttttg   2940
gctgtgacgc acagttcata gagataacct tcacccggtt gccagaggtg cggattcacc   3000
acttgcaaag tcccgctagt gccttgtcca gttgcaacca cctgttgatc cgcatcacgc   3060
agttcaacgc tgacatcacc attggccacc acctgccagt caacagacgc gtggttacag   3120
tcttgcgcga catgcgtcac cacggtgata tcgtccaccc aggtgttcgg cgtggtgtag   3180
agcattacgc tgcgatggat tccggcatag ttaaagaaat catggaagta agactgcttt   3240
ttcttgccgt tttcgtcggt aatcaccatt cccggcggga tagtctgcca gttcagttcg   3300
ttgttcacac aaacggtgat acccctcgac ggattaaaga cttcaagcgg tcaactatga   3360
agaagtgttc gtcttcgtcc cagtaagcta tgtctccaga atgtagccat ccatccttgt   3420
caatcaaggc gttggtcgct tccggattgt ttacataacc ggacataatc ataggtcctc   3480
tgacacataa ttcgcctctc tgattaacgc ccagcgtttt cccggtatcc agatccacaa   3540
ccttcgcttc aaaaaatgga acaactttac cgaccgcgcc cggtttatca tccccctcgg   3600
gtgtaatcag aatagctgat gtagtctcag tgagcccata tccttgtcgt atccctggaa   3660
gatggaagcg ttttgcaacc gcttccccga cttctttcga aagaggtgcg cccccagaag   3720
caatttcgtg taaattagat aaatcgtatt tgtcaatcag agtgcttttg gcgaagaatg   3780
aaaatagggt tggtactagc aacgcacttt gaattttgta atcctgaagg gatcgtaaaa   3840
acagctcttc ttcaaatcta tacattaaga cgactcgaaa tccacatatc aaatatccga   3900
gtgtagtaaa cattccaaaa ccgtgatgga atggaacaac acttaaaatc gcagtatccg   3960
gaatgatttg attgccaaaa ataggatctc tggcatgcga gaatctagcg caggcagttc   4020
tatgcggaag ggccacaccc ttaggtaacc cagtagatcc agaggaattg ttttgtcacg   4080
atcaaaggac tctggtacaa aatcgtattc attaaaaccg ggaggtagat gagatgtgac   4140
gaacgtgtac atcgactgaa atccctggta atccgtttta gaatccatga taataatttt   4200
ctggattatt ggtaattttt tttgcacgtt caaaattttt tgcaacccct ttttggaaac   4260
aaacactacg gtaggctgcg aaatgttcat actgttgagc aattcacgtt cattataaat   4320
gtcgttcgcg ggcgcaactg caactccgat aaataacgcg cccaacaccg gcataaagaa   4380
ttgaagagag ttttcactgc atacgacgat tctgtgattt gtattcagcc catatcgttt   4440
catagcttct gccaaccgaa cggacatttc gaagtattcc gcgtacgtga tgttcacctc   4500
gatatgtgca tctgtaaaag gaattgttcc aggaaccagg gcgtatctct tcatagcctt   4560
atgcagttgc tctccagcgg ttccatcctc tagctttgct tctcaatttc ttatttgcat   4620
aatgagaaaa aaaggaaaat taattttaac accaattcag tagttgattg agcaaatgcg   4680
ttgccaaaaa ggatgcttta gagacagtgt tctctgcaca gataaggaca aacattattc   4740
agagggagta cccagagctg agactcctaa gccagtgagt ggcacagcat tctagggaga   4800
aatatgcttg tcatcaccga agcctgattc cgtagagcca caccttggta agggccaatc   4860
tgctcacaca ggatagagag ggcaggagcc agggcagagc atataaggtg aggtaggatc   4920
agttgctcct cacatttgct tctgacatag ttgtgttggg agcttggatc gatccaccat   4980
gggcttcaat accctgattg actggaacag ctgtagccct gaacagcagc gtgcgctgct   5040
```

-continued

```
gacgcgtccg gcgatttccg cctctgacag tattacccgg acggtcagcg atattctgga   5100
taatgtaaaa acgcgcggtg acgatgccct gcgtgaatac agcgctaaat ttgataaaac   5160
agaagtgaca gcgctacgcg tcacccctga agagatcgcc gccgccggcg cgcgtctgag   5220
cgacgaatta aaacaggcga tgaccgctgc cgtcaaaaat attgaaacgt tccattccgc   5280
gcagacgcta ccgcctgtag atgtggaaac ccagccaggc gtgcgttgcc agcaggttac   5340
gcgtcccgtc tcgtctgtcg gtctgtatat tcccggcggc tcggctccgc tcttctcaac   5400
ggtgctgatg ctggcgacgc cggcgcgcat tgcgggatgc cagaaggtgg ttctgtgctc   5460
gccgccgccc atcgctgatg aaatcctcta tgcggcgcaa ctgtgtggcg tgcaggaaat   5520
ctttaacgtc ggcggcgcgc aggcgattgc cgctctggcc ttcggcagcg agtccgtacc   5580
gaaagtggat aaaatttttg gccccggcaa cgcctttgta accgaagcca aacgtcaggt   5640
cagccagcgt ctcgacggcg cggctatcga tatgccagcc gggccgtctg aagtactggt   5700
gatcgcagac agcggcgcaa caccggattt cgtcgcttct gacctgctct cccaggctga   5760
gcacggcccg gattcccagg tgatcctgct gacgcctgat gctgacattg cccgcaaggt   5820
ggcggaggcg gtagaacgta aactggcgga actgccgcgc gcggacaccg cccggcaggc   5880
cctgagcgcc agtcgtctga ttgtgaccaa agatttagcg cagtgcgtcg ccatctctaa   5940
tcagtatggg ccggaacact taatcatcca gacgcgcaat gcgcgcgatt tggtggatgc   6000
gattaccagc gcaggctcgg tatttctcgg cgactggtcg ccggaatccg ccggtgatta   6060
cgcttccgga accaaccatg ttttaccgac ctatggctat actgctacct gttccagcct   6120
tgggttagcg gatttccaga aacggatgac cgttcaggaa ctgtcgaaag cgggcttttc   6180
cgctctggca tcaaccattg aaacattggc ggcggcagaa cgtctgaccg cccataaaaa   6240
tgccgtgacc ctgcgcgtaa acgccctcaa ggagcaagca tgagcactga aaacactctc   6300
agcgtcgctg acttagcccg tgaaaatgtc cgcaacctgg agatccagac atgataagat   6360
acattgatga gtttggacaa accacaacta gaatgcagtg aaaaaaatgc tttatttgtg   6420
aaatttgtga tgctattgct ttatttgtaa ccattataag ctgcaataaa caagttaaca   6480
acaacaattg cattcatttt atgtttcagg ttcaggggga ggtgtgggag gtttttttaaa   6540
gcaagtaaaa cctctacaaa tgtggtatgg ctgattatga tctctagctc gacggcgcgc   6600
ctctagagca gtgtggtttt gcaagaggaa gcaaaaagcc tctccaccca ggcctggaat   6660
gtttccaccc aatgtcgagc agtgtggttt tgcaagagga agcaaaaagc ctctccaccc   6720
aggcctggaa tgtttccacc caatgtcgag caaaccccgc ccagcgtctt gtcattggcg   6780
aattcgaaca cgcagatgca gtcggggcgg cgcggtccca gtcccacttc gcatattaag   6840
gtgacgcgtg tggcctcgaa caccgagcga ccctgcagcc aatatgggat cggccattga   6900
acaagatgga ttgcacgcag gttctccggc cgcttgggtg gagaggctat tcggctatga   6960
ctgggcacaa cagacaatcg gctgctctga tgccgccgtg ttccggctgt cagcgcaggg   7020
gcgcccggtt ctttttgtca agaccgacct gtccggtgcc ctgaatgaac tgcaggtaag   7080
tgcggccgtc gatggccgag gcggcctcgg cctctgcata aataaaaaaa attagtcagc   7140
catgcatggg gcggagaatg ggcggaactg ggcggagtta ggggcgggat gggcggagtt   7200
aggggcggga ctatggttgc tgactaattg agatgcatgc tttgcatact tctgcctgct   7260
ggggagcctg gggactttcc acacctggtt gctgactaat tgagatgcat gctttgcata   7320
cttctgcctg ctggggagcc tggggacttt ccacacccta actgacacac attccacaga   7380
attaattccc ctagttatta atagtaatca attacggggt cattagttca tagcccatat   7440
```

-continued

```
atggagttcc gcgttacata acttacggta aatggcccgc ctggctgacc gcccaacgac   7500
ccccgcccat tgacgtcaat aatgacgtat gttcccatag taacgccaat agggactttc   7560
cattgacgtc aatgggtgga ctatttacgg taaactgccc acttggcagt acatcaagtg   7620
tatcatatgc caagtacgcc ccctattgac gtcaatgacg gtaaatggcc cgcctggcat   7680
tatgcccagt acatgacctt atgggacttt cctacttggc agtacatcta gctattagtc   7740
atcgctatta ccatggtgat gcggttttgg cagtacatca atgggcgtgg atagcggttt   7800
gactcacggg gatttccaag tctccacccc attgacgtca atgggagttt gttttggcac   7860
caaaatcaac gggactttcc aaaatgtcgt aacaactccg ccccattgac gcaaatgggc   7920
ggtaggcgtg tacggtggga ggtctatata agcagagctg ggtacgtgaa ccgtcagatc   7980
gcctggagac gccatcacag atctctcact atggattttc aggtgcagat tatcagcttc   8040
ctgctaatca gtgcttcagt cataatgtcc agaggacaaa ttgttctctc ccagtctcca   8100
gcaatcctgt ctgcatctcc aggggagaag gtcacaatga cttgcagggc cagctcaagt   8160
gtaagttaca tccactggtt ccagcagaag ccaggatcct cccccaaacc ctggatttat   8220
gccacatcca acctggcttc tggagtccct gttcgcttca gtggcagtgg gtctgggact   8280
tcttactctc tcacaatcag cagagtggag gctgaagatg ctgccactta ttactgccag   8340
cagtggacta gtaacccacc cacgttcgga ggggggacca agctggaaat caaacgtacg   8400
gtggctgcac catctgtctt catcttcccg ccatctgatg agcagttgaa atctggaact   8460
gcctctgttg tgtgcctgct gaataacttc tatcccagag aggccaaagt acagtggaag   8520
gtggataacg ccctccaatc gggtaactcc caggagagtg tcacagagca ggacagcaag   8580
gacagcacct acagcctcag cagcaccctg acgctgagca aagcagacta cgagaaacac   8640
aaagtctacg cctgcgaagt cacccatcag ggcctgagct cgcccgtcac aaagagcttc   8700
aacaggggag agtgttgaat tcagatccgt taacggttac caactaccta gactggattc   8760
gtgacaacat gcggccgtga tatctacgta tgatcagcct cgactgtgcc ttctagttgc   8820
cagccatctg ttgtttgccc ctcccccgtg ccttccttga ccctggaagg tgccactccc   8880
actgtccttt cctaataaaa tgaggaaatt gcatcgcatt gtctgagtag gtgtcattct   8940
attctggggg gtggggtggg gcaggacagc aagggggagg attgggaaga caatagcagg   9000
catgctgggg atgcggtggg ctctatggaa ccagctgggg ctcgacagct atgccaagta   9060
cgccccctat tgacgtcaat gacggtaaat ggcccgcctg gcattatgcc cagtacatga   9120
ccttatggga ctttcctact tggcagtaca tctacgtatt agtcatcgct attaccatgg   9180
tgatgcggtt ttggcagtac atcaatgggc gtggatagcg gtttgactca cggggatttc   9240
caagtctcca ccccattgac gtcaatggga gtttgttttg gcaccaaaat caacgggact   9300
ttccaaaatg tcgtaacaac tccgccccat tgacgcaaat gggcggtagg cgtgtacggt   9360
gggaggtcta tataagcaga gctgggtacg tcctcacatt cagtgatcag cactgaacac   9420
agacccgtcg acatgggttg gagcctcatc ttgctcttcc ttgtcgctgt tgctacgcgt   9480
gtcctgtccc aggtacaact gcagcagcct ggggctgagc tggtgaagcc tggggcctca   9540
gtgaagatgt cctgcaaggc ttctggctac acatttacca gttacaatat gcactgggta   9600
aaacagacac ctggtcgggg cctggaatgg attggagcta tttatcccgg aaatggtgat   9660
acttcctaca atcagaagtt caaaggcaag gccacattga ctgcagacaa atcctccagc   9720
acagcctaca tgcagctcag cagcctgaca tctgaggact ctgcggtcta ttactgtgca   9780
```

-continued

```
agatcgactt actacggcgg tgactggtac ttcaatgtct ggggcgcagg gaccacggtc   9840
accgtctctg cagctagcac caagggccca tcggtcttcc ccctggcacc ctcctccaag   9900
agcacctctg ggggcacagc ggccctgggc tgcctggtca aggactactt ccccgaaccg   9960
gtgacggtgt cgtggaactc aggcgccctg accagcggcg tgcacacctt cccggctgtc  10020
ctacagtcct caggactcta ctccctcagc agcgtggtga ccgtgccctc cagcagcttg  10080
ggcacccaga cctacatctg caacgtgaat cacaagccca gcaacaccaa ggtggacaag  10140
aaagcagagc ccaaatcttg tgacaaaact cacacatgcc caccgtgccc agcacctgaa  10200
ctcctggggg gaccgtcagt cttcctcttc cccccaaaac ccaaggacac cctcatgatc  10260
tcccggaccc ctgaggtcac atgcgtggtg gtggacgtga gccacgaaga ccctgaggtc  10320
aagttcaact ggtacgtgga cggcgtggag gtgcataatg ccaagacaaa gccgcgggag  10380
gagcagtaca acagcacgta ccgtgtggtc agcgtcctca ccgtcctgca ccaggactgg  10440
ctgaatggca aggagtacaa gtgcaaggtc tccaacaaag ccctcccagc ccccatcgag  10500
aaaaccatct ccaaagccaa agggcagccc cgagaaccac aggtgtacac cctgccccca  10560
tcccgggatg agctgaccaa gaaccaggtc agcctgacct gcctggtcaa aggcttctat  10620
cccagcgaca tcgccgtgga gtgggagagc aatgggcagc cggagaacaa ctacaagacc  10680
acgcctcccg tgctggactc cgacggctcc ttcttcctct acagcaagct caccgtggac  10740
aagagcaggt ggcagcaggg gaacgtcttc tcatgctccg tgatgcatga ggctctgcac  10800
aaccactaca cgcagaagag cctctccctg tctccgggta aatgaggatc cgttaacggt  10860
taccaactac ctagactgga ttcgtgacaa catgcggccg tgatatctac gtatgatcag  10920
cctcgactgt gccttctagt tgccagccat ctgttgtttg cccctccccc gtgccttcct  10980
tgaccctgga aggtgccact cccactgtcc tttcctaata aaatgaggaa attgcatcgc  11040
attgtctgag taggtgtcat tctattctgg ggggtggggt ggggcaggac agcaaggggg  11100
aggattggga agacaatagc aggcatgctg gggatgcggt gggctctatg gaaccagctg  11160
gggctcgaca gcaacgctag gtcgaggccg ctactaactc tctcctccct ccttttttcct  11220
gcaggacgag gcagcgcggc tatcgtggct ggccacgacg ggcgttcctt gcgcagctgt  11280
gctcgacgtt gtcactgaag cgggaaggga ctggctgcta ttgggcgaag tgccggggca  11340
ggatctcctg tcatctcacc ttgctcctgc cgagaaagta tccatcatgg ctgatgcaat  11400
gcggcggctg catacgcttg atccggctac ctgcccattc gaccaccaag cgaaacatcg  11460
catcgagcga gcacgtactc ggatggaagc cggtcttgtc gatcaggatg atctggacga  11520
agagcatcag gggctcgcgc cagccgaact gttcgccagg taagtgagct ccaattcaag  11580
cttcctaggg cggccagcta gtagctttgc ttctcaattt cttatttgca taatgagaaa  11640
aaaaggaaaa ttaattttaa caccaattca gtagttgatt gagcaaatgc gttgccaaaa  11700
aggatgcttt agagacagtg ttctctgcac agataaggac aaacattatt cagagggagt  11760
acccagagct gagactccta agccagtgag tggcacagca ttctagggag aaatatgctt  11820
gtcatcaccg aagcctgatt ccgtagagcc acaccttggt aagggccaat ctgctcacac  11880
aggatagaga gggcaggagc cagggcagag catataaggt gaggtaggat cagttgctcc  11940
tcacatttgc ttctgacata gttgtgttgg gagcttggat agcttggaca gctcagggct  12000
gcgatttcgc gccaaacttg acggcaatcc tagcgtgaag gctggtagga ttttatcccc  12060
gctgccatca tggttcgacc attgaactgc atcgtcgccg tgtcccaaaa tatggggatt  12120
ggcaagaacg gagacctacc ctggcctccg ctcaggaacg agttcaagta cttccaaaga  12180
```

-continued atgaccacaa cctcttcagt ggaaggtaaa cagaatctgg tgattatggg taggaaaacc 12240
tggttctcca ttcctgagaa gaatcgacct ttaaaggaca gaattaatat agttctcagt 12300
agagaactca aagaaccacc acgaggagct cattttcttg ccaaaagttt ggatgatgcc 12360
ttaagactta ttgaacaacc ggaattggca agtaaagtag acatggtttg gatagtcgga 12420
ggcagttctg tttaccagga agccatgaat caaccaggcc accttagact ctttgtgaca 12480
aggatcatgc aggaatttga aagtgacacg tttttcccag aaattgattt ggggaaatat 12540
aaacttctcc cagaataccc aggcgtcctc tctgaggtcc aggaggaaaa aggcatcaag 12600
tataagtttg aagtctacga gaagaaagac taacaggaag atgctttcaa gttctctgct 12660
cccctcctaa agctatgcat ttttataaga ccatgggact tttgctggct ttagatcagc 12720
ctcgactgtg ccttctagtt gccagccatc tgttgtttgc ccctcccccg tgccttcctt 12780
gaccctggaa ggtgccactc ccactgtcct ttcctaataa aatgaggaaa ttgcatcgca 12840
ttgtctgagt aggtgtcatt ctattctggg gggtggggtg gggcaggaca gcaaggggga 12900
ggattgggaa gacaatagca ggcatgctgg ggatgcggtg ggctctatgg aaccagctgg 12960
ggctcgaagc ggccgcccat ttcgctggtg gtcagatgcg ggatggcgtg ggacgcggcg 13020
gggagcgtca cactgaggtt ttccgccaga cgccactgct gccaggcgct gatgtgcccg 13080
gcttctgacc atgcggtcgc gttcggttgc actacgcgta ctgtgagcca gagttgcccg 13140
gcgctctccg gctgcggtag ttcaggcagt tcaatcaact gtttaccttg tggaccgaca 13200
tccagaggca cttcaccgct tgccagcggc ttaccatcca gcgccaccat ccagtgcagg 13260
agctcgttat cgctatgacg gaacaggtat tcgctggtca cttcgatggt ttgcccggat 13320
aaacggaact ggaaaaactg ctgctggtgt tttgcttccg tcagcgctgg atgcggcgtg 13380
cggtcggcaa agaccagacc gttcatacag aactggcgat cgttcggcgt atcgccaaaa 13440
tcaccgccgt aagccgacca cgggttgccg ttttcatcat atttaatcag cgactgatcc 13500
acccagtccc agacgaagcc gccctgtaaa cggggatact gacgaaacgc ctgccagtat 13560
ttagcgaaac cgccaagact gttacccatc gctggggcgt attcgcaaag gatcagcggg 13620
cgcgtctctc cgggtagcga aagccatttt ttgatggacc atttcggacc agccgggaag 13680
ggctggtctt catccacgcg cgcgtacatc gggcaaataa tatcggtggc cgtggtgtcg 13740
gctccgccgc cttcatactg caccgggcgg gaaggatcga cagatttgat ccagcgatac 13800
agcgcgtcgt gattagcgcc gtggcctgat tcattcccca gcgaccagat gatcacactc 13860
gggtgattac gatcgcgctg caccattcgc gttacgcgtt cgctcatcgc cggtagccag 13920
cgcggatcat cggtcagacg attcattggc accatgccgt gggtttcaat attggcttca 13980
tccaccacat acaggccgta gcggtcgcac agcgtgtacc acagcggatg gttcggataa 14040
tgccaacagc gcacggcgtt aaagttgttc tgcttcatca gcaggatatc ctgcaccatc 14100
gtctgctcat ccatgacctg accatgcaga ggatgatgct cgtgacggtt aacgcctcga 14160
atcagcaacg gcttgccgtt cagcagcagc agaccatttt caatccgcac ctcgcggaaa 14220
ccgacatcgc aggcttctgc ttcaatcagc gtgccgtcgg cggtgtgcag ttcaaccacc 14280
gcacgataga gattcgggat ttcggcgctc cacagtttcg ggttttcgac gttcagacgc 14340
agtgtgacgc gatcggcata accaccacgc tcatcgataa tttcaccgcc gaaaggcgcg 14400
gtgccgctgg cgacctgcgt ttcaccctgc cataaagaaa ctgttacccg taggtagtca 14460
cgcaactcgc cgcacatctg aacttcagcc tccagtacag cgcggctgaa atcatcatta 14520

-continued

```
aagcgagtgg caacatggaa atcgctgatt tgtgtagtcg gtttatgcag caacgagacg  14580
tcacggaaaa tgccgctcat ccgccacata tcctgatctt ccagataact gccgtcactc  14640
caacgcagca ccatcaccgc gaggcggttt tctccggcgc gtaaaaatgc gctcaggtca  14700
aattcagacg gcaaacgact gtcctggccg taaccgaccc acgccccgtt gcaccacaga  14760
tgaaacgccg agttaacgcc atcaaaaata attcgcgtct ggccttcctg tagccagctt  14820
tcatcaacat taaatgtgag cgagtaacaa cccgtcggat tctccgtggg aacaaacggc  14880
ggattgaccg taatgggata ggttacgttg gtgtagatgg gcgcatcgta accgtgcatc  14940
tgccagtttg aggggacgac gacagtatcg gcctcaggaa gatcgcactc cagccagctt  15000
tccggcaccg cttctggtgc cggaaaccag gcaaagcgcc attcgccatt caggctgcgc  15060
aactgttggg aagggcgatc ggtgcgggcc tcttcgctat tacgccagct ggcgaaaggg  15120
ggatgtgctg caaggcgatt aagttgggta acgccagggt tttcccagtc acgacgttgt  15180
aaaacgactt aatccgtcga ggggctgcct cgaagcagac gaccttccgt tgtgcagcca  15240
gcggcgcctg cgccggtgcc cacaatcgtg cgcgaacaaa ctaaaccaga acaaattata  15300
ccggcggcac cgccgccacc accttctccc gtgcctaaca ttccagcgcc tccaccacca  15360
ccaccaccat cgatgtctga attgccgccc gctccaccaa tgccgacgga acctcaaccc  15420
gctgcacctt tagacgacag acaacaattg ttggaagcta ttagaaacga aaaaaatcgc  15480
actcgtctca gaccggtcaa accaaaaacg gcgcccgaaa ccagtacaat agttgaggtg  15540
ccgactgtgt tgcctaaaga gacatttgag cctaaaccgc cgtctgcatc accgccacca  15600
cctccgcctc cgcctccgcc gccagccccg cctgcgcctc caccgatggt agatttatca  15660
tcagctccac caccgccgcc attagtagat ttgccgtctg aaatgttacc accgcctgca  15720
ccatcgcttt ctaacgtgtt gtctgaatta aaatcgggca cagttagatt gaaacccgcc  15780
caaaaacgcc cgcaatcaga aataattcca aaaagctcaa ctacaaattt gatcgcggac  15840
gtgttagccg acacaattaa taggcgtcgt gtggctatgg caaaatcgtc ttcggaagca  15900
acttctaacg acgagggttg ggacgacgac gataatcggc ctaataaagc taacacgccc  15960
gatgttaaat atgtccaagc tactagtggt accgcttggc agaacatatc catcgcgtcc  16020
gccatctcca gcagccgcac gcggcgcatc tcgggcagcg ttgggtcctg gccacgggtg  16080
cgcatgatcg tgctcctgtc gttgaggacc cggctaggct ggcggggttg ccttactggt  16140
tagcagaatg aatcaccgat acgcgagcga acgtgaagcg actgctgctg caaaacgtct  16200
gcgacctgag caacaacatg aatggtcttc ggtttccgtg tttcgtaaag tctggaaacg  16260
cggaagtcag cgccctgcac cattatgttc cggatctgca tcgcaggatg ctgctggcta  16320
ccctgtggaa cacctacatc tgtattaacg aagcgctggc attgaccctg agtgattttt  16380
ctctggtccc gccgcatcca taccgccagt tgtttaccct cacaacgttc cagtaaccgg  16440
gcatgttcat catcagtaac ccgtatcgtg agcatcctct ctcgtttcat cggtatcatt  16500
acccccatga acagaaatcc cccttacacg gaggcatcag tgaccaaaca ggaaaaaacc  16560
gcccttaaca tggcccgctt tatcagaagc cagacattaa cgcttctgga gaaactcaac  16620
gagctggacg cggatgaaca ggcagacatc tgtgaatcgc ttcacgacca cgctgatgag  16680
ctttaccgca gctgcctcgc gcgtttcggt gatgacggtg aaaacctctg acacatgcag  16740
ctcccggaga cggtcacagc ttgtctgtaa gcggatgccg ggagcagaca agcccgtcag  16800
ggcgcgtcag cgggtgttgg cgggtgtcgg ggcgcagcca tgacccagtc acgtagcgat  16860
agcggagtgt atactggctt aactatgcgg catcagagca gattgtactg agagtgcacc  16920
```

-continued atatgcggtg tgaaataccg cacagatgcg taaggagaaa ataccgcatc aggcgctctt 16980
ccgcttcctc gctcactgac tcgctgcgct cggtcgttcg gctgcggcga gcggtatcag 17040
ctcactcaaa ggcggtaata cggttatcca cagaatcagg ggataacgca ggaaagaaca 17100
tgtgagcaaa aggccagcaa aaggccagga accgtaaaaa ggccgcgttg ctggcgtttt 17160
tccataggct ccgcccccct gacgagcatc acaaaaatcg acgctcaagt cagaggtggc 17220
gaaacccgac aggactataa agataccagg cgtttccccc tggaagctcc ctcgtgcgct 17280
ctcctgttcc gaccctgccg cttaccggat acctgtccgc ctttctccct tcgggaagcg 17340
tggcgctttc tcatagctca cgctgtaggt atctcagttc ggtgtaggtc gttcgctcca 17400
agctgggctg tgtgcacgaa ccccccgttc agcccgaccg ctgcgcctta tccggtaact 17460
atcgtcttga gtccaacccg gtaagacacg acttatcgcc actggcagca gccactggta 17520
acaggattag cagagcgagg tatgtaggcg gtgctacaga gttcttgaag tggtggccta 17580
actacggcta cactagaagg acagtatttg gtatctgcgc tctgctgaag ccagttacct 17640
tcggaaaaag agttggtagc tcttgatccg gcaaacaaac caccgctggt agcggtggtt 17700
tttttgtttg caagcagcag attacgcgca gaaaaaaagg atctcaagaa gatcctttga 17760
tcttttctac ggggtctgac gctcagtgga acgaaaactc acgttaaggg attttggtca 17820
tgagattatc aaaaaggatc ttcacctaga tccttttaaa ttaaaaatga agttttaaat 17880
caatctaaag tatatatgag taaacttggt ctgacagtta ccaatgctta atcagtgagg 17940
cacctatctc agcgatctgt ctatttcgtt catccatagt tgcctgactc cccgtcgtgt 18000
agataactac gatacgggag ggcttaccat ctggccccag tgctgcaatg ataccgcgag 18060
acccacgctc accggctcca gatttatcag caataaacca gccagccgga agggccgagc 18120
gcagaagtgg tcctgcaact ttatccgcct ccatccagtc tattaattgt tgccgggaag 18180
ctagagtaag tagttcgcca gttaatagtt tgcgcaacgt tgttgccatt gctgcaggca 18240
tcgtggtgtc acgctcgtcg tttggtatgg cttcattcag ctccggttcc caacgatcaa 18300
ggcgagttac atgatccccc atgttgtgca aaaaagcggt tagctccttc ggtcctccga 18360
tcgttgtcag aagtaagttg gccgcagtgt tatcactcat ggttatggca gcactgcata 18420
attctcttac tgtcatgcca tccgtaagat gcttttctgt gactggtgag tactcaacca 18480
agtcattctg agaatagtgt atgcggcgac cgagttgctc ttgcccggcg tcaacacggg 18540
ataataccgc gccacatagc agaactttaa aagtgctcat cattggaaaa cgttcttcgg 18600
ggcgaaaact ctcaaggatc ttaccgctgt tgagatccag ttcgatgtaa cccactcgtg 18660
cacccaactg atcttcagca tcttttactt tcaccagcgt ttctgggtga gcaaaaacag 18720
gaaggcaaaa tgccgcaaaa aagggaataa gggcgacacg gaaatgttga atactcatac 18780
tcttcctttt tcaatattat tgaagcattt atcagggtta ttgtctcatg agcggataca 18840
tatttgaatg tatttagaaa aataaacaaa taggggttcc gcgcacattt ccccgaaaag 18900
tgccacctga cgtctaagaa accattatta tcatgacatt aacctataaa aataggcgta 18960
tcacgaggcc ctttcgtctt caagaa 18986

<210> SEQ ID NO 3
<211> LENGTH: 19040
<212> TYPE: DNA
<213> ORGANISM: Artificial Sequence
<220> FEATURE:
<223> OTHER INFORMATION: Description of Artificial Sequence: Synthetic
DNA referred to as “Mandy”

-continued

<400> SEQUENCE: 3
ttaattaagg ggcggagaat gggcggaact gggcggagtt aggggcggga tgggcggagt 60
taggggcggg actatggttg ctgactaatt gagatgcatg ctttgcatac ttctgcctgc 120
tggggagcct ggggactttc cacacctggt tgctgactaa ttgagatgca tgctttgcat 180
acttctgcct gctggggagc ctggggactt tccacaccct aactgacaca cattccacag 240
aattaattcc cctagttatt aatagtaatc aattacgggg tcattagttc atagcccata 300
tatggagttc cgcgttacat aacttacggt aaatggcccg cctggctgac cgcccaacga 360
cccccgccca ttgacgtcaa taatgacgta tgttcccata gtaacgccaa tagggacttt 420
ccattgacgt caatgggtgg agtatttacg gtaaactgcc cacttggcag tacatcaagt 480
gtatcatatg ccaagtacgc cccctattga cgtcaatgac ggtaaatggc ccgcctggca 540
ttatgcccag tacatgacct tatgggactt tcctacttgg cagtacatct acgtattagt 600
catcgctatt accatggtga tgcggttttg gcagtacatc aatgggcgtg gatagcggtt 660
tgactcacgg ggatttccaa gtctccaccc cattgacgtc aatgggagtt tgttttgaag 720
ctgtttaaac agcttggccg gccagcttta tttaacgtgt ttacgtcgag tcaattgtac 780
actaacgaca gtgatgaaag aaatacaaaa gcgcataata ttttgaacga cgtcgaacct 840
ttattacaaa acaaaacaca aacgaatatc gacaaagcta gattgctgct acaagatttg 900
gcaagttttg tggcgttgag cgaaaatcca ttagatagtc cagccatcgg ttcggaaaaa 960
caacccttgt ttgaaactaa tcgaaaccta ttttacaaat ctattgagga tttaatattt 1020
aaattcagat ataaagacgc tgaaaatcat ttgattttcg ctctaacata ccaccctaaa 1080
gattataaat ttaatgaatt attaaaatac atcagcaact atatattgat agacatttcc 1140
agtttgtgat attagtttgt gcgtctcatt acaatggctg ttatttttaa caacaaacaa 1200
ctgctcgcag acaatagtat agaaaaggga ggtgaactgt tttgtttaa cggttcgtac 1260
aacattttgg aaagttatgt taatccggtg ctgctaaaaa atggtgtaat tgaactagaa 1320
gaagctgcgt actatgccgg caacatattg tacaaaaccg acgatcccaa attcattgat 1380
tatataaatt taataattaa agcaacacac tccgaagaac taccagaaaa tagcactgtt 1440
gtaaattaca gaaaaactat gcgcagcggt actatacacc ccattaaaaa agacatatat 1500
atttatgaca acaaaaaatt tactctatac gatagataca tatatggata cgataataac 1560
tatgttaatt tttatgagga gaaaaatgaa aaagagaagg aatacgaaga agaagacgac 1620
aaggcgtcta gtttatgtga aaataaaatt atattgtcgc aaattaactg tgaatcattt 1680
gaaaatgatt ttaaatatta cctcagcgat tataactacg cgttttcaat tatagataat 1740
actacaaatg ttcttgttgc gtttggtttg tatcgttaat aaaaaacaaa tttgacattt 1800
ataattgttt tattattcaa taattacaaa taggattgag acccttgcag ttgccagcaa 1860
acggacagag cttgtcgagg agagttgttg attcattgtt tgcctccctg ctgcggtttt 1920
tcaccgaagt tcatgccagt ccagcgtttt tgcagcagaa aagccgccga cttcggtttg 1980
cggtcggcga gtgaagatcc ctttcttgtt accgccaacg cgcaatatgc cttgcgaggt 2040
cgcaaaatcg gcgaaattcc atacctgttc accgacgacg gcgctgacgc gatcaaagac 2100
gcggtgatac atatccagcc atgcacactg atactcttca ctccacatgt cggtgtacat 2160
tgagtgcagc ccggctaacg tatccacgcc gtattcggtg atgataatcg gctgatgcag 2220
tttctcctgc caggccagaa gttctttttc cagtaccttc tctgccgttt ccaaatcgcc 2280

-continued gctttgggac ataccatccg taataacggt tcaggcacag cacatcaaag agatcgctga 2340
tggtatcggt gtgagcgtcg cagaacatta cattgacgca ggtgatcgga cgcgtcgggt 2400
cgagtttacg cgttgcttcc gccagtggcg cgaaatattc ccgtgcacct tgcggacggg 2460
tatccggttc gttggcaata ctccacatca ccacgcttgg gtggtttttg tcacgcgcta 2520
tcagctcttt aatcgcctgt aagtgcgctt gctgagtttc cccgttgact gcctcttcgc 2580
tgtacagttc tttcggcttg ttgcccgctt cgaaaccaat gcctaaagag aggttaaagc 2640
cgacagcagc agtttcatca atcaccacga tgccatgttc atctgcccag tcgagcatct 2700
cttcagcgta agggtaatgc gaggtacggt aggagttggc cccaatccag tccattaatg 2760
cgtggtcgtg caccatcagc acgttatcga atcctttgcc acgcaagtcc gcatcttcat 2820
gacgaccaaa gccagtaaag tagaacggtt tgtggttaat caggaactgt tcgcccttca 2880
ctgccactga ccggatgccg acgcgaagcg ggtagatatc acactctgtc tggcttttgg 2940
ctgtgacgca cagttcatag agataacctt cacccggttg ccagaggtgc ggattcacca 3000
cttgcaaagt cccgctagtg ccttgtccag ttgcaaccac ctgttgatcc gcatcacgca 3060
gttcaacgct gacatcacca ttggccacca cctgccagtc aacagacgcg tggttacagt 3120
cttgcgcgac atgcgtcacc acggtgatat cgtccaccca ggtgttcggc gtggtgtaga 3180
gcattacgct gcgatggatt ccggcatagt taaagaaatc atggaagtaa gactgctttt 3240
tcttgccgtt ttcgtcggta atcaccattc ccggcgggat agtctgccag ttcagttcgt 3300
tgttcacaca aacggtgata cccctcgacg gattaaagac ttcaagcggt caactatgaa 3360
gaagtgttcg tcttcgtccc agtaagctat gtctccagaa tgtagccatc catccttgtc 3420
aatcaaggcg ttggtcgctt ccggattgtt tacataaccg gacataatca taggtcctct 3480
gacacataat tcgcctctct gattaacgcc cagcgttttc ccggtatcca gatccacaac 3540
cttcgcttca aaaaatggaa caactttacc gaccgcgccc ggtttatcat ccccctcggg 3600
tgtaatcaga atagctgatg tagtctcagt gagcccatat ccttgtcgta tccctggaag 3660
atggaagcgt tttgcaaccg cttccccgac ttctttcgaa agaggtgcgc ccccagaagc 3720
aatttcgtgt aaattagata aatcgtattt gtcaatcaga gtgcttttgg cgaagaatga 3780
aaatagggtt ggtactagca acgcactttg aattttgtaa tcctgaaggg atcgtaaaaa 3840
cagctcttct tcaaatctat acattaagac gactcgaaat ccacatatca aatatccgag 3900
tgtagtaaac attccaaaac cgtgatggaa tggaacaaca cttaaaatcg cagtatccgg 3960
aatgatttga ttgccaaaaa taggatctct ggcatgcgag aatctgacgc aggcagttct 4020
atgcggaagg gccacaccct taggtaaccc agtagatcca gaggaattgt tttgtcacga 4080
tcaaaggact ctggtacaaa atcgtattca ttaaaaccgg gaggtagatg agatgtgacg 4140
aacgtgtaca tcgactgaaa tccctggtaa tccgttttag aatccatgat aataattttc 4200
tggattattg gtaatttttt ttgcacgttc aaaatttttt gcaacccctt tttggaaaca 4260
aacactacgg taggctgcga aatgttcata ctgttgagca attcacgttc attataaatg 4320
tcgttcgcgg gcgcaactgc aactccgata aataacgcgc ccaacaccgg cataaagaat 4380
tgaagagagt tttcactgca tacgacgatt ctgtgatttg tattcagccc atatcgtttc 4440
atagcttctg ccaaccgaac ggacatttcg aagtattccg cgtacagccc ggccgtttaa 4500
acggccgggc ttcaataccc tgattgactg gaacagctgt agccctgaac agcagcgtgc 4560
gctgctgacg cgtccggcga tttccgcctc tgacagtatt acccggacgg tcagcgatat 4620
tctggataat gtaaaaacgc gcggtgacga tgccctgcgt gaatacagcg ctaaatttga 4680

-continued

```
taaaacagaa gtgacagcgc tacgcgtcac ccctgaagag atcgccgccg ccggcgcgcg   4740
tctgagcgac gaattaaaac aggcgatgac cgctgccgtc aaaaatattg aaacgttcca   4800
ttccgcgcag acgctaccgc ctgtagatgt ggaaacccag ccaggcgtgc gttgccagca   4860
ggttacgcgt cccgtctcgt ctgtcggtct gtatattccc ggcggctcgg ctccgctctt   4920
ctcaacggtg ctgatgctgg cgacgccggc gcgcattgcg ggatgccaga aggtggttct   4980
gtgctcgccg ccgcccatcg ctgatgaaat cctctatgcg gcgcaactgt gtggcgtgca   5040
ggaaatcttt aacgtcggcg gcgcgcaggc gatttgccgc tctggccttc ggcagcgagt   5100
ccgtaccgaa agtggataaa atttttggcc ccggcaacgc ctttgtaacc gaagccaaac   5160
gtcaggtcag ccagcgtctc gacggcgcgg ctatcgatat gccagccggg cggtctgaag   5220
tactggtgat cgcagacagc ggcgcaacac cggatttcgt cgcttctgac ctgctcttcc   5280
caggctgagc acggcccgga ttcccaggtg atcctgctga cgcctgatgc tgacattgcc   5340
cgcaaggtgg cggaggcggt agaacgtcaa ctggcggaac tgccgcgcgc ggacaccgcc   5400
cggcaggccc tgagcgccag tcgtctgatt gtgaccaaag atttagcgca gtgcgtcgcc   5460
atctctaatc agtatgggcc ggaacactta atcatccaga cgcgcaatgc gcgcgatttg   5520
gtggatgcga ttaccagcgc aggctcggta tttctcggcg actggtcgcc ggaatccgcc   5580
ggtgattacg cttccggaac caaccatgtt ttaccgacct atggctatac tgctacctgt   5640
tccagccttg ggttagcgga tttccagaaa cggatgaccg ttcaggaact gtcgaaagcg   5700
ggcttttccg ctctggcatc aaccattgaa acattggcgg cggcagaacg tctgaccgcc   5760
cataaaaatg ccgtgaccct gcgcgtaaac gccctcaagg agcaagcatg agcactgaaa   5820
acactctcag cgtcgctgac ttagcccgtg aaaatgtccg caacctggag atccagacat   5880
ggataagata cattgatgag tttggacaaa ccacaactag aatgcagtga aaaaaatgct   5940
ttatttgtga aatttgtgat gctattgctt tatttgtaac cattataagc tgcaataaac   6000
aagttaacaa caacaattgc attcatttta tgtttcaggt tcagggggag gtgtgggagg   6060
tttttaaag caagtaaaac ctctacaaat gtggtatggc tgattatgat ctctagggcc   6120
ggccctcgac ggcgcgtcta gagcagtgtg gttttcaaga ggaagcaaaa agcctctcca   6180
cccaggcctg gaatgtttcc acccaatgtc gagcagtgtg gttttgcaag aggaagcaaa   6240
aagcctctcc acccaggcct ggaatgtttc cacccaatgt cgagcaaacc ccgcccagcg   6300
tcttgtcatt ggcgaattgg aacacgcata tgcagtcggg gcggcgcggt cccaggtcca   6360
cttcgcatat taaggtggcg cgtgtggcct cgaacaccga gcgaccctgc agccaatatg   6420
ggatcggcca ttgaacaaga tggattgcac gcaggttctc cggccgcttg ggtggagagg   6480
ctattcggct atgactgggc acaacagaca atcggctgct ctgatgccgc cgtgttccgg   6540
ctgtcagcgc aggggcgccc ggttcttttt gtcaagaccg acctgtccgg tgccctgaat   6600
gaactgcagg taagtgcggc cgtcgatggc cgaggcggcc tcggcctctg cataaataaa   6660
aaaaattagt cagccatgca tggggcggag aatgggcgga actgggcgga gttaggggcg   6720
ggatgggcgg agttaggggc gggactatgg ttgctgacta attgagatgc atgctttgca   6780
tacttctgcc tgctggggag cctggggact ttccacacct ggttgctgac taattgagat   6840
gcatgctttg catacttctg cctgctgggg agcctgggga ctttccacac cctaactgac   6900
acacattcca cagaattaat tcccctagtt attaatagta atcaattacg gggtcattag   6960
ttcatagccc atatatggag ttccgcgtta cataacttac ggtaaatggc ccgcctggct   7020
```

-continued

```
gaccgcccaa cgacccccgc ccattgacgt caataatgac gtatgttccc atagtaacgc   7080
caatagggac tttccattga cgtcaatggg tggagtattt acggtaaact gcccacttgg   7140
cagtacatca agtgtatcat atgccaagta cgccccctat tgacgtcaat gacggtaaat   7200
ggcccgcctg gcattatgcc cagtacatga ccttatggga ctttcctact tgccagtaca   7260
tctacgtatt agtcatcgct attaccatgg tgatgcggtt ttggcagtac atcaatgggc   7320
gtggatagcg gtttgactca cggggatttc caagtctcca ccccattgac gtcaatggga   7380
gtttgttttg gcaccaaaat caacgggact ttccaaaatg tcgtaacaac tccgccccat   7440
tgacgcaaat gggcggtagg cgtgtacggt gggaggtcta tataagcaga gctgggtacg   7500
tgaaccgtca gatcgcctgg agacgccatc acagatctct caccatggac atgagggtcc   7560
ccgctcagct cctggggctc cttctgctct ggctcccagg tgccagatgt gacatccaga   7620
tgacccagtc tccatcttcc ctgtctgcat ctgtagggga cagagtcacc atcacttgca   7680
gggcaagtca ggacattagg tattatttaa attggtatca gcagaaacca ggaaaagctc   7740
ctaagctcct gatctatgtt gcatccagtt tgcaaagtgg ggtcccatca aggttcagcg   7800
gcagtggatc tgggacagag ttcactctca ccgtcagcag cctgcagcct gaagattttg   7860
cgacttatta ctgtctacag gtttatagta cccctcggac gttcggccaa gggaccaagg   7920
tggaaatcaa acgtacggtg gctgcaccat ctgtcttcat cttcccgcca tctgatgagc   7980
agttgaaatc tggaactgcc tctgttgtgt gcctgctgaa taacttctat cccagagagg   8040
ccaaagtaca gtggaaggtg gataacgccc tccaatcggg taactcccag gagagtgtca   8100
cagagcagga cagcaaggac agcacctaca gcctcagcag caccctgacg ctgagcaaag   8160
cagactacga gaaacacaaa gtctacgcct gcgaagtcac ccatcagggc ctgagctcgc   8220
ccgtcacaaa gagcttcaac aggggagagt gttgaattca gatccgttaa cggttaccaa   8280
ctacctagac tggattcgtg acaacatgcg gccgtgatat ctacgtatga tcagcctcga   8340
ctgtgccttc tagttgccag ccatctgttg tttgcccctc ccccgtgcct tccttgaccc   8400
tggaaggtgc cactcccact gtcctttcct aataaaatga ggaaattgca tcgcattgtc   8460
tgagtaggtg tcattctatt ctggggggtg gggtggggca ggacagcaag ggggaggatt   8520
gggaagacaa tagcaggcat gctggggatg cggtgggctc tatggcttct gaggcggaaa   8580
gaaccagctg gggctagtcg caattgggcg gagttagggg cgggatgggc ggagttaggg   8640
gcggggacta tggtgctgac taattgagat gcatgctttg catacttctg cctgctgggg   8700
agcctgggga ctttccacac ctggttgctg actaattgag atgcatgctt tgcatacttc   8760
tgcctgctgg ggagcctggg gactttccac accctaactg acacacattc cacagaatta   8820
attcccctag ttattaatag taatcaatta cggggtcatt agttcatagc ccatatatgg   8880
agttccgcgt tacataactt acggtaaatg gcccgcctgg ctgaccgccc aacgaccccc   8940
gcccattgac gtcaataatg acgtatgttc ccatagtaac gccaataggg actttccatt   9000
gacgtcaatg ggtggagtat ttacggtaaa ctgcccactt ggcagtacat caagtgtatc   9060
atatgccaag tacgccccct attgacgtca atgacggtaa atggcccgcc tggcattatg   9120
cccagtacat gaccttatgg gactttccta cttggcagta catctacgta ttagtcatcg   9180
ctgttaccat ggtgatgcgg ttttggcagt acatcaatgg gcgtggatag cggtttgact   9240
cacggggatt tccaagtctc caccccattg acgtcaatgg gagtttgttt tggcaccaaa   9300
atcaacggga ctttccaaaa tgtcgtaaca actccgcccc attgacgcaa atgggcggta   9360
ggcgtgtacg gtgggaggtc tatataagca gagctgggta cgtgaaccgt cagatcgcct   9420
```

-continued

```
ggagacgccg tcgacatggg ttggagcctc atcttgctct tccttgtcgc tgttgctacg   9480
cgtgtcctgt ccgaggtgca gctggtggag tctgggggcg gcttggcaaa gcctgggggg   9540
tccctgagac tctcctgcgc agcctccggg ttcaggttca ccttcaataa ctactacatg   9600
gactgggtcc gccaggctcc agggcagggg ctggagtggg tctcacgtat tagtagtagt   9660
ggtgatccca catggtacgc agactccgtg aagggcagat tcaccatctc cagagagaac   9720
gccaagaaca cactgtttct tcaaatgaac agcctgagag ctgaggacac ggctgtctat   9780
tactgtgcga gcttgactac agggtctgac tccctggggc cagggagtcc tggtcaccgt   9840
ctcctcagct agcaccaagg gcccatcggt cttccccctg gcaccctcct ccaagagcac   9900
ctctgggggc acagcggccc tgggctgcct ggtcaaggac tacttccccg aaccggtgac   9960
ggtgtcgtgg aactcaggcg ccctgaccag cggcgtgcac accttcccgg ctgtcctaca  10020
gtcctcagga ctctactccc tcagcagcgt ggtgaccgtg ccctccagca gcttgggcac  10080
ccagacctac atctgcaacg tgaatcacaa gcccagcaac accaaggtgg acaagaaagt  10140
tgagcccaaa tcttgtgaca aaactcacac atgcccaccg tgcccagcac ctgaactcct  10200
ggggggaccg tcagtcttcc tcttcccccc aaaacccaag gacaccctca tgatctcccg  10260
gacccctgag gtcacatgcg tggtggtgga cgtgagccac gaagaccctg aggtcaagtt  10320
caactggtac gtggacggcg tggaggtgca taatgccaag acaaagccgc gggaggagca  10380
gtacaacagc acgtaccgtg tggtcagcgt cctcaccgtc ctgcaccagg actggctgaa  10440
tggcaaggag tacaagtgca aggtctccaa caaagccctc ccagccccca tcgagaaaac  10500
catctccaaa gccaaagggc agccccgaga accacaggtg tacaccctgc ccccatcccg  10560
ggatgagctg accaagaacc aggtcagcct gacctgcctg gtcaaaggct tctatcccag  10620
cgacatcgcc gtggagtggg agagcaatgg gcagccggag aacaactaca agaccacgcc  10680
tcccgtgctg gactccgacg gctccttctt cctctacagc aagctcaccg tggacaagag  10740
caggtggcag caggggaacg tcttctcatg ctccgtgatg catgaggctc tgcacaacca  10800
ctacacgcag aagagcctct ccctgtctcc gggtaaatga ggatccgtta acggttacca  10860
actacctaga ctggattcgt gacaacatgc ggccgtgata tctacgtatg atcagcctcg  10920
actgtgcctt ctagttgcca gccatctgtt gtttgccccc tcccccgtgc cttccttgac  10980
cctggaaggt gccactccca ctgtcctttc ctaataaaat gaggaaattg catcgcattg  11040
tctgagtagg tgtcattcta ttctgggggg tggggtgggg caggacagca agggggagga  11100
ttgggaagac aatagcaggc atgctgggga tgcggtgggc tctatggctt ctgaggcgga  11160
aagaaccagc tggggctcga cagcaacgct aggtcgaggc cgctactaac tctctcctcc  11220
ctcctttttc ctgcaggacg aggcagcgcg gctatcgtgg ctggccacga cgggcgttcc  11280
ttgcgcagct gtgctcgacg ttgtcactga agcgggaagg gactggctgc tattgggcga  11340
agtgccgggg caggatctcc tgtcatctca ccttgctcct gccgagaaag tatccatcat  11400
ggctgatgca atgcggcggc tgcatacgct tgatccggct acctgcccat tcgaccacca  11460
agcgaaacat cgcatcgagc gagcacgtac tcggatggaa gccggtcttg tcgatcagga  11520
tgatctggac gaagagcatc aggggctcgc gccagccgaa ctgttcgcca ggtaagtgag  11580
ctccaattca agctctcgag ctagggcggc cagctagtag ctttgcttct caatttctta  11640
tttgcataat gagaaaaaaa ggaaaattaa ttttaacacc aattcagtag ttgattgagc  11700
aaatgcgttg ccaaaaagga tgctttagag acagtgttct ctgcacagat aaggacaaac  11760
```

-continued

```
attattcaga gggagtaccc agagctgaga ctcctaagcc agtgagtggc acagcatcca  11820
gggagaaata tgcttgtcat caccgaagcc tgattccgta gagccacacc ctggtaaggg  11880
ccaatctgct cacacaggat agagagggca ggagccaggc agagcatata aggtgaggta  11940
ggatcagttg ctcctcacat ttgcttctga catagttgtg ttgggagctt ggatagcttg  12000
ggggggggac agctcagggc tgcgatttcg cgccaaactt gacggcaatc ctagcgtgaa  12060
ggctggtagg attttatccc cgctgccatc atggttcgac cattgaactg catcgtcgcc  12120
gtgtcccaaa atatggggat tggcaagaac ggagacctac cctggcctcc gctcaggaac  12180
gagttcaagt acttccaaag aatgaccaca acctcttcag tggaaggtaa acagaatctg  12240
gtgattatgg gtaggaaaac ctggttctcc attcctgaga agaatcgacc tttaaaggac  12300
agaattaata tagttctcag tagagaactc aaagaaccac cacgaggagc tcattttctt  12360
gccaaaagtt tggatgatgc cttaacgtag gcgcgccatt aagacttatt gaacaaccgg  12420
aattggcaag taaagtagac atggtttgga tagtcggagg cagttctgtt taccaggaag  12480
ccatgaatca accaggcaac ctcagactct ttgtgacaag gatcatgcag gaatttgaaa  12540
gtgacacgtt tttcccagaa attgatttgg ggaaatataa acttctccca gaatacccag  12600
gcgtcctctc tgaggtcaag gaggaaaaag gcatcaagta taagtttgaa gtctacgaga  12660
agaaagacta acaggaagat gctttcaagt tctctgctcc cctcctaaag ctatgcattt  12720
ttataagacc atgggacttt tgctggcttt agatcagcct cgactgtgcc ttctagttgc  12780
cagccatctg ttgtttgccc ctcccccgtg ccttccttga ccctggaagg tgccactccc  12840
actgtccttt cctaataaaa tgaggaaatt gcatcgcatt gtctgagtag gtgtcattct  12900
attctggggg gtggggtggg gcaggacagc aagggggagg attgggaaga caatagcagg  12960
catgctgggg atgcggtggg ctctatggct tctgaggcgg aaagaaccag ctggggctcg  13020
aagcggccgc ccatttcgct ggtggtcaga tgcgggatgg cgtgggacgc ggcggggagc  13080
gtcacactga ggttttccgc cagacgccac tgctgccagg cgctgatgtg cccggcttct  13140
gaccatgcgg tcgcgttcgg ttgcactacg cgtactgtga gccagagttg cccggcgctc  13200
tccggctgcg gtagttcagg cagttcaatc aactgtttac cttgtggagc gacatccaga  13260
ggcacttcac cgcttgccag cggcttacca tccagcgcca ccatccagtg caggagctcg  13320
ttatcgctat gacggaacag gtattcgctg gtcacttcga tggtttgccc ggataaacgg  13380
aactggaaaa actgctgctg gtgttttgct tccgtcagcg ctggatgcgg cgtgcggtcg  13440
gcaaagacca gaccgttcat acagaactgg cgatccgttc ggctatcgcc aaaatcaccg  13500
ccgtaagccg accacgggtt gccgttttca tcatatttaa tcagcgactg atccacccag  13560
tcccagacga agccgccctg taaacgggga tactgacgaa acgcctgcca gtatttagcg  13620
aaaccgccaa gactgttacc catcgcgtgg gcgtattcgc aaaggatcag cgggcgcgtc  13680
tctccaggta gcgaaagcca ttttttgatg gaccatttcg gcacagccgg gaagggctgg  13740
tcttcatcca cgcgcgcgta catcgggcaa ataatatcgg tggccgtggt gtcggctccg  13800
ccgccttcat actgcaccgg gcgggaagga tcgacagatt tgatccagcg atacagcgcg  13860
tcgtgattag cgccgtggcc tgattcattc cccagcgacc agatgatcac actcgggtga  13920
ttacgatcgc gctgcaccat tcgcgttacg cgttcgctca tcgccggtag ccagcgcgga  13980
tcatcggtca gacgattcat tggcaccatg ccgtgggttt caatattggc ttcatccacc  14040
acatacaggc cgtagcggtc gcacagcgtg taccacagcg gatggttcgg ataatgcgaa  14100
cagcgcacgg cgttaaagtt gttctgcttc atcagcagga tatcctgcac catcgtctgc  14160
```

-continued

```
tcatccatga cctgaccatg cagaggatga tgctcgtgac ggttaacgcc tcgaatcagc  14220
aacggcttgc cgttcagcag cagcagacca ttttcaatcc gcacctcgcg gaaaccgaca  14280
tcgcaggctt ctgcttcaat cagcgtgccg tcggcggtgt gcagttcaac caccgcacga  14340
tagagattcg ggatttcggc gctccacagt ttcgggtttt cgacgttcag acgtagtgtg  14400
acgcgatcgg cataaccacc acgctcatcg ataatttcac cgccgaaagg cgcggtgccg  14460
ctggcgacct gcgtttcacc ctgccataaa gaaactgtta cccgtaggta gtcacgcaac  14520
tcgccgcaca tctgaacttc agcctccagt acagcgcggc tgaaatcatc attaaagcga  14580
gtggcaacat ggaaatcgct gatttgtgta gtcggtttat gcagcaacga gacgtcacgg  14640
aaaatgccgc tcatccgcca catatcctga tcttccagat aactgccgtc actccagcgc  14700
agcaccatca ccgcgaggcg gttttctccg gcgcgtaaaa atgcgctcag gtcaaattca  14760
gacggcaaac gactgtcctg gccgtaaccg acccagcgcc cgttgcacca cagatgaaac  14820
gccgagttaa cgccatcaaa aataattcgc gtctggcctt cctgtagcca gctttcatca  14880
acattaaatg tgagcgagta acaacccgtc ggattctccg tgggaacaaa cggcggattg  14940
accgtaatgg gataggtcac gttggtgtag atgggcgcat cgtaaccgtg catctgccag  15000
tttgagggga cgacgacagt atcggcctca ggaagatcgc actccagcca gctttccggc  15060
accgcttctg gtgccggaaa ccagggcaag cgccattcgc cattcaggct gcgcaactgt  15120
tgggaagggc gatcggtgcg ggcctcttcg ctattacgcc agctggcgaa agggggatgt  15180
gctgcaaggc gattaagttg ggtaacgcca gggttttccc agtcacgacg ttgtaaaacg  15240
acttaatccg tcgaggggct gcctcgaagc agacgacctt ccgttgtgca gccagcggcg  15300
cctgcgccgg tgcccacaat cgtgcgcgaa caaactaaac cagaacaaat tataccggcg  15360
gcaccgccgc caccaccttc tcccgtgcct aacattccag cgcctccacc accaccacca  15420
ccatcgatgt ctgaattgcc gcccgctcca ccaatgccga cggaacctca acccgctgca  15480
cctttagacg acagacaaca attgttggaa gctattagaa acgaaaaaaa tcgcactcgt  15540
ctcagaccgg tcaaaccaaa aacggcgccc gaaaccagta caatagttga ggtgccgact  15600
gtgttgccta aagagacatt tgagcctaaa ccgccgtctg catcaccgcc accacctccg  15660
cctccgcctc cgccgccagc cccgcctgcg cctccaccga tggtagattt atcatcagct  15720
ccaccaccgc cgccattagt agatttgccg tctgaaatgt taccaccgcc tgcaccatcg  15780
ctttctaacg tgttgtctga attaaaatcg ggcacagtta gattgaaacc cgcccaaaaa  15840
cgcccgcaat cagaaataat tccaaaaagc tcaactacaa atttgatcgc ggacgtgtta  15900
gccgacacaa ttaataggcg tcgtgtggct atggcaaaat cgtcttcgga agcaacttct  15960
aacgacgagg gttgggacga cgacgataat cggcctaata aagctaacac gcccgatgtt  16020
aaatatgtcc aagctactag tggtaccgct tggcagaaca tatccatcgc gtccgccatc  16080
tccagcagcc gcacgcggcg catctcgggc agcgttgggt cctggccacg ggtgcgcatg  16140
atcgtgctcc tgtcgttgag gacccggcta ggctggcggg gttgccttac tggttagcag  16200
aatgaatcac cgatacgcga gcgaacgtga agcgactgct gctgcaaaac gtctgcgacc  16260
tgagcaacaa catgaatggt cttcggtttc cgtgtttcgt aaagtctgga aacgcggaag  16320
tcagcgccct gcaccattat gttccggatc tgcatcgcag gatgctgctg gctaccctgt  16380
ggaacaccta catctgtatt aacgaagcgc tggcattgac cctgagtgat ttttctctgg  16440
tcccgccgca tccataccgc cagttgttta ccctcacaac gttccagtaa ccgggcatgt  16500
```

-continued

```
tcatcatcag taacccgtat cgtgagcatc ctctctcgtt tcatcggtat cattaccccc  16560
atgaacagaa atccccctta cacggaggca tcagtgacca aacaggaaaa aaccgccctt  16620
aacatggccc gctttatcag aagccagaca ttaacgcttc tggagaaact caacgagctg  16680
gacgcggatg aacaggcaga catctgtgaa tcgcttcacg accacgctga tgagctttac  16740
cgcagctgcc tcgcgcgttt cggtgatgac ggtgaaaacc tctgacacat gcagctcccg  16800
gagacggtca cagcttgtct gtaagcggat gccgggagca gacaagcccg tcagggcgcg  16860
tcagcgggtg ttggcgggtg tcggggcgca gccatgaccc agtcacgtag cgatagcgga  16920
gtgtatactg gcttaactat gcggcatcag agcagattgt actgagagtg caccatatgc  16980
ggtgtgaaat accgcacaga tgcgtaagga gaaaataccg catcaggcgc tcttccgctt  17040
cctcgctcac tgactcgctg cgctcggtcg ttcggctgcg gcgagcggta tcagctcact  17100
caaaggcggt aatacggtta tccacagaat caggggataa cgcaggaaag aacatgtgag  17160
caaaaggcca gcaaaaggcc aggaaccgta aaaaggccgc gttgctggcg tttttccata  17220
ggctccgccc ccctgacgag catcacaaaa atcgacgctc aagtcagagg tggcgaaacc  17280
cgacaggact ataaagatac caggcgtttc cccctggaag ctccctcgtg cgctctcctg  17340
ttccgaccct gccgcttacc ggatacctgt ccgcctttct cccttcggga agcgtggcgc  17400
tttctcatag ctcacgctgt aggtatctca gttcggtgta ggtcgttcgc tccaagctgg  17460
gctgtgtgca cgaacccccc gttcagcccg accgctgcgc cttatccggt aactatcgtc  17520
ttgagtccaa cccggtaaga cacgacttat cgccactggc agcagccact ggtaacagga  17580
ttagcagagc gaggtatgta ggcggtgcta cagagttctt gaagtggtgg cctaactacg  17640
gctacactag aaggacagta tttggtatct gcgctctgct gaagccagtt accttcggaa  17700
aaagagttgg tagctcttga tccggcaaac aaaccaccgc tggtagcggt ggtttttttg  17760
tttgcaagca gcagattacg cgcagaaaaa aaggatctca agaagatcct ttgatctttt  17820
ctacggggtc tgacgctcag tggaacgaaa actcacgtta agggattttg gtcatgagat  17880
tatcaaaaag gatcttcacc tagatccttt taaattaaaa atgaagtttt aaatcaatct  17940
aaagtatata tgagtaaact tggtctgaca gttaccaatg cttaatcagt gaggcaccta  18000
tctcagcgat ctgtctattt cgttcatcca tagttgcctg actccccgtc gtgtagataa  18060
ctacgatacg ggagggctta ccatctggcc ccagtgctgc aatgataccg cgagacccac  18120
gctcaccggc tccagattta tcagcaataa accagccagc cggaagggcc gagcgcagaa  18180
gtggtcctgc aactttatcc gcctccatcc agtctattaa ttgttgccgg gaagctagag  18240
taagtagttc gccagttaat agtttgcgca acgttgttgc cattgctgca ggcatcgtgg  18300
tgtcacgctc gtcgtttggt atggcttcat tcagctccgg ttcccaacga tcaaggcgag  18360
ttacatgatc ccccatgttg tgcaaaaaag cggttagctc cttcggtcct ccgatcgttg  18420
tcagaagtaa gttggccgca gtgttatcac tcatggttat ggcagcactg cataattctc  18480
ttactgtcat gccatccgta agatgctttt ctgtgactgg tgagtactca accaagtcat  18540
tctgagaata gtgtatgcgg cgaccgagtt gctcttgccc ggcgtcaaca cgggataata  18600
ccgcgccaca tagcagaact ttaaaagtgc tcatcattgg aaaacgttct tcggggcgaa  18660
aactctcaag gatcttaccg ctgttgagat ccagttcgat gtaacccact cgtgcaccca  18720
actgatcttc agcatctttt actttcacca gcgtttctgg gtgagcaaaa acaggaaggc  18780
aaaatgccgc aaaaaaggga ataagggcga cacggaaatg ttgaatactc atactcttcc  18840
tttttcaata ttattgaagc atttatcagg gttattgtct catgagcgga tacatatttg  18900
```

-continued

```
aatgtattta gaaaaataaa caaatagggg ttccgcgcac atttccccga aaagtgccac  18960

ctgacgtcta agaaaccatt attatcatga cattaaccta taaaaatagg cgtatcacga  19020

ggccctttcg tcttcaagaa                                              19040
```

METHOD FOR INTEGRATING GENES AT SPECIFIC SITES IN MAMMALIAN CELLS VIA HOMOLOGOUS RECOMBINATION AND VECTORS FOR ACCOMPLISHING THE SAME

RELATED APPLICATIONS

This is a continuation of U.S. patent application Ser. No. 10/109,853, filed Apr. 1, 2002, now U.S. Pat. No. 6,841,383 B2, which is a continuation of U.S. patent application Ser. No. 09/343,485, filed Jun. 30, 1999, now U.S. Pat. No. 6,413,777, which is a continuation of U.S. patent application Ser. No. 09/023,715, filed Feb. 13, 1998 now U.S. Pat. No. 5,998,144, which is a continuation-in-part of U.S. patent application Ser. No. 08/819,866, filed Mar. 14, 1997, now U.S. Pat. No. 5,830,698. Each of the foregoing priority documents is incorporated herein in its entirety.

FIELD OF THE INVENTION

The present invention relates to a process of targeting the integration of a desired exogenous DNA to a specific location within the genome of a mammalian cell. More specifically, the invention describes a novel method for identifying a transcriptionally active target site ("hot spot") in the mammalian genome, and inserting a desired DNA at this site via homologous recombination. The invention also optionally provides the ability for gene amplification of the desired DNA at this location by co-integrating an amplifiable selectable marker, e.g., DHFR, in combination with the exogenous DNA. The invention additionally describes the construction of novel vectors suitable for accomplishing the above, and further provides mammalian cell lines produced by such methods which contain a desired exogenous DNA integrated at a target hot spot.

BACKGROUND

Technology for expressing recombinant proteins in both prokaryotic and eukaryotic organisms is well established. Mammalian cells offer significant advantages over bacteria or yeast for protein Production, resulting from their ability to correctly assemble, glycosylate. and post-translationally modify recombinantly expressed proteins. After transfection into the host cells, recombinant expression constructs can be maintained as extrachromosomal elements, or may be integrated into the host cell genome. Generation of-stably transfected mammalian cell lines usually involves the latter; a DNA construct encoding a gene of interest along with a drug resistance gene (dominant selectable marker) is introduced into the host cell, and subsequent growth in the presence of the drug allows for the selection of cells that have successfully integrated the exogenous DNA. In many instances, the gene of interest is linked to a drug resistant selectable marker which can later be subjected to gene amplification. The gene encoding dihydrofolate reductase (DHFR) is most commonly used for this purpose. Growth of cells in the presence of methotrexate, a competitive inhibitor of DHFR, leads to increased DHFR production by means of amplification of the DHFR gene. As flanking regions of DNA will also become amplified, the resultant coamplification of a DHFR linked gene in the transfected cell line can lead to increased protein production, thereby resulting in high level expression of the gene of interest.

While this approach has proven successful, there are a number of problems with the system because of the random nature of the integration event. These problems exist because expression levels are greatly influenced by the effects of the local genetic environment at the gene locus, a phenomena well documented in the literature and generally referred to as "position effects" (for example, see Al-Shawi et al, *Mol. Cell. Biol.,* 10:1192–1198 (1990); Yoshimura et al, *Mol. Cell. Biol.,* 7:1296–1299 (1987)). As the vast majority of mammalian DNA is in a transcriptionally inactive state, random integration methods offer no control over the transcriptional fate of the integrated DNA. Consequently, wide variations in the expression level of integrated genes can occur, depending on the site of integration. For example, integration of exogenous DNA into inactive, or transcriptionally "silent" regions of the genome will result in little or no expression. By contrast integration into a transcriptionally active site may result in high expression.

Therefore, when the goal of the work is to obtain a high level of gene expression, as is typically the desired outcome of genetic engineering methods, it is generally necessary to screen large numbers of transfectants to find such a high producing clone. Additionally, random integration of exogenous DNA into the genome can in some instances disrupt important cellular genes, resulting in an altered phenotype. These factors can make the generation of high expressing stable mammalian cell lines a complicated and laborious process.

Recently, the use of DNA vectors containing translationally impaired dominant selectable markers in mammalian gene expression has been described. (This is disclosed in co-owned U.S. Ser. No. 08/147,696 filed Nov. 3, 1993, now U.S. Pat. No. 5,736,137).

These vectors contain a translationally impaired neomycin phosphotransferase (neo) gene as the dominant selectable marker, artificially engineered to contain an intron into which a DHFR gene along with a gene or genes of interest is inserted. Use of these vectors as expression constructs has been found to significantly reduce the total number of drug resistant colonies produced, thereby facilitating the screening procedure in relation to conventional mammalian expression vectors. Furthermore, a significant percentage of the clones obtained using this system are high expressing clones. These results are apparently attributable to the modifications made to the neo selectable marker. Due to the translational impairment of the neo gene, transfected cells will not produce enough neo protein to survive drug selection, thereby decreasing the overall number of drug resistant colonies. Additionally, a higher percentage of the surviving clones will contain the expression vector integrated into sites in the genome where basal transcription levels are high, resulting in overproduction of neo, thereby allowing the cells to overcome the impairment of the neo gene. Concomitantly, the genes of interest linked to neo will be subject to similar elevated levels of transcription. This same advantage is also true as a result of the artificial intron created within neo; survival is dependent on the synthesis of a functional neo gene, which is in turn dependent on correct and efficient splicing of the neo introns. Moreover, these criteria are more likely to be met if the vector DNA has integrated into a region which is already highly transcriptionally active.

Following integration of the vector into a transcriptionally active region, gene amplification is performed by selection for the DHFR gene. Using this system, it has been possible to obtain clones selected using low levels of methotrexate (50 nM), containing few (<10) copies of the vector which secrete high levels of protein (>55 pg/cell/day). Furthermore, this can be achieved in a relatively short period of time. However, the success in amplification is variable. Some transcriptionally active sites cannot be amplified and therefore the frequency and extent of amplification from a particular site is not predictable.

Overall, the use of these translationally impaired vectors represents a significant improvement over other methods of random integration. However, as discussed, the problem of lack of control over the integration site remains a significant concern.

One approach to overcome the problems of random integration is by means of gene targeting, whereby the exogenbus DNA is directed to specific locus within the host genome. The exogenous DNA is inserted by means of homologous recombination occurring between sequences of DNA in the expression vector and the corresponding homologous sequence in the genome. However, while this type of recombination occurs at a high frequency naturally in yeast and other fungal organisms, in higher eukaryotic organisms it is an extremely rare event. In mammalian cells, the frequency-of homologous versus non-homologous (random integration) recombination is reported to range from 1/100 to 1/5000 (for example, see Capecchi., *Science,* 244:1288–1292 (1989); Morrow and Kucherlapati, *Curr. Op. Biotech.,* 4:577–582 (1993)).

One of the earliest reports describing homologous recombination in mammalian cells comprised an artificial system created in mouse fibroblasts (Thomas et al, *Cell,* 44:419–428 (1986)). A cell line containing a mutated, non-functional version of the neo gene integrated into the host genome was created, and subsequently targeted with a second non-functional copy of neo containing a different mutation. Reconstruction of a functional neo gene could occur only by gene targeting. Homologous recombinants were identified by selecting for G418 resistant cells, and confirmed by analysis of genomic DNA isolated from the resistant clones.

Recently, the use of homologous recombination to replace the heavy and light immunoglobulin genes at endogenous loci in antibody secreting cells has been reported. (U.S. Pat. No. 5,202,238, Fell et al, (1993).) However, this particular approach is not widely applicable, because it is limited to the production of immunoglobulins in cells which endogenously express immunoglobulins, e.g., B cells and myeloma cells. Also, expression is limited to single copy gene levels because co-amplification after homologous recombination is not included. The method is further complicated by the fact that two separate integration events are required to produce a functional immunoglobulin: one for the light chain gene followed by one for the heavy chain gene.

An additional example of this type of system has been reported in NS/0 cells, where recombinant immunoglobulins are expressed by homologous recombination into the immunoglobulin gamma 2A locus (Hollis et al, international patent application #PCT/IB95 (00014).) Expression levels obtained from this site were extremely high—on the order of 20 pg/cell/day from a single copy integrant. However, as in the above example, expression is limited to this level because an amplifiable gene is not contegrated in this system. Also, other researchers have reported aberrant glycosylation of recombinant proteins expressed in NS/0 cells (for example, see Flesher et al, *Biotech. and Bioeng.,* 48:399–407 (1995)), thereby limiting the applicability of this approach.

The cre-loxP recombination system from bacteriophage P1 has recently been adapted and used as a means of gene targeting in eukaryotic cells. Specifically, the site specific integration of exogenous DNA into the Chinese hamster ovary (CHO) cell genome using cre recombinase and a series of lox containing vectors have been described. (Fukushige and Sauer, *Proc. Natl. Acad. Sci. USA,* 89:7905–7909 (1992).) This system is attractive in that it provides for reproducible expression at the same chromosomal location. However, no effort was made to identify a chromosomal site from which gene expression is optimal, and as in the above example, expression is limited to single copy levels in this system. Also, it is complicated by the fact that one needs to provide for expression of a functional recombinase enzyme in the mammalian cell.

The use of homologous recombination between an introduced DNA sequence and its endogenous chromosomal locus has also beer reported to provide a useful means of genetic manipulation in mammalian cells, as well as in yeast cells. (See e.g., Bradley et al, *Meth. Enzymol.,* 223:855–879 (1993); Capecchi, *Science,* 244:1288–1292 (1989); Rothstein et al, *Meth. Enzymol.,* 194:281–301 (1991)). To date, most mammalian gene targeting studies have been directed toward gene disruption ("knockout") or site-specific mutagenesis of selected target gene loci in mouse embryonic stem (ES) cells. The creation of these "knockout" mouse models has enabled scientists to examine specific structure-function issues and examine the biological importance of a myriad of mouse genes. This field of research also has important implications in terms of potential gene therapy applications.

Also, vectors have recently been reported by Cell-tech (Kent, U.K.) which purportedly are targeted to transcriptionally active sites in NSO cells, which do not require gene amplification (Peakman et al, *Hum. Antibod. Hybridomas,* 5:65–74 (1994)). However, levels of immunoglobulin secretion in these unamplified cells have not been reported to exceed 20 pg/cell/day, while in amplified CHO cells, levels as high as 100 pg/cell/day can be obtained (Id.).

It would be highly desirable to develop a gene targeting system which reproducibly provided for the integration of exogenous DNA into a predetermined site in the genome known to be transcriptionally active. Also, it would be desirable if such a gene targeting system would further facilitate co-amplification of the inserted DNA after integration. The design of such a system would allow for the reproducible and high level expression of any cloned gene of interest in a mammalian cell, and undoubtedly would be of significant interest to many researchers.

In this application, we provide a novel mammalian expression system, based on homologous recombination occurring between two artificial substrates contained in two different vectors. Specifically, this system uses a combination of two novel mammalian expression vectors, referred to as a "marking" vector and a "targeting" vector.

Essentially, the marking vector enables the identification and marking of a site in the mammalian genome which is transcriptionally active, i.e., a site at which gene expression levels are high. This site can be regarded as a "hot spot" in the genome. After integration of the marking vector, the subject expression system enables another DNA to be integrated at this site, i.e., the targeting vector, by means of homologous recombination occurring between DNA sequences common to both vectors. This system affords significant advantages over other homologous recomboination systems.

Unlike most other homologous systems employed in mammalian cells, this system exhibits no background. Therefore, cells which have only undergone random integration of the vector do not survive the selection. Thus, any gene of interest cloned into the targeting plasmid is expressed at high levels from the marked hot spot. Accordingly, the subject method of gene expression substantially or completely eliminates the problems inherent to systems of random integration, discussed in detail above. Moreover, this system provides reproducible and high level expression of any recombinant protein at the same transcriptionally active site in the mammalian genome. In addition, gene amplification may be effected at this particular transcriptionally active site by including an amplifiable dominant selectable marker (e.g. DHFR) as part of the marking vector.

OBJECTS OF THE INVENTION

Thus, it is an object of the invention to provide an improved method for targeting a desired DNA to a specific site in a mammalian cell.

It is a more specific object of the invention to provide a novel method for targeting a desired DNA to a specific site in a mammalian cell via homologous recombination.

It is another specific object of the invention to provide novel vectors for achieving site specific integration of a desired DNA in a mammalian cell.

It is still another object of the invention to provide novel mammalian cell lines which contain a desired DNA integrated at a predetermined site which provides for high expression.

It is a more specific object of the invention to provide a novel method for achieving site specific integration of a desired DNA in a Chinese hamster ovary (CHO) cell.

It is another more specific object of the invention to provide a novel method for integrating immunoglobulin genes, or any other genes, in mammalian cells at predetermined chromosomal sites that provide for high expression.

It is another specific object of the invention to provide novel vectors and vector combinations suitable for integrating immunoglobulin genes into mammalian cells at predetermined sites that provide for high expression.

It is another object of the invention to provide mammalian cell lines which contain immunoglobulin genes integrated at predetermined sites that provide for high expression.

It is an even more specific object of the invention to provide a novel method for integrating immunoglobulin genes into CHO cells that provide for high expression, as well as novel vectors and vector combinations that provide for such integration of immunoglobulin genes into CHO cells.

In addition, it is a specific object of the invention to provide novel CHO cell lines which contain immunoglobin genes integrated at predetermined sites that provide for high expression, and have been amplified by methotrexate selection to secrete even greater amounts of functional immunoglobulins.

BRIEF DESCRIPTION OF THE FIGURES

FIG. 2(*b*) shows a linearized version of Molly, after digestion with the restriction enzymes Kpn1 and Pac1. This linearized form was used for transfection.

Lane 1: λHindIII DNA size marker
Lane 2: Desmond clone 10F3
Lane 3: Desmond clone 10C12
Lane 4: Desmond clone 15C9
Lane 5: Desmond clone 14B5
Lane 6: Desmond clone 9B2

Figure 5:
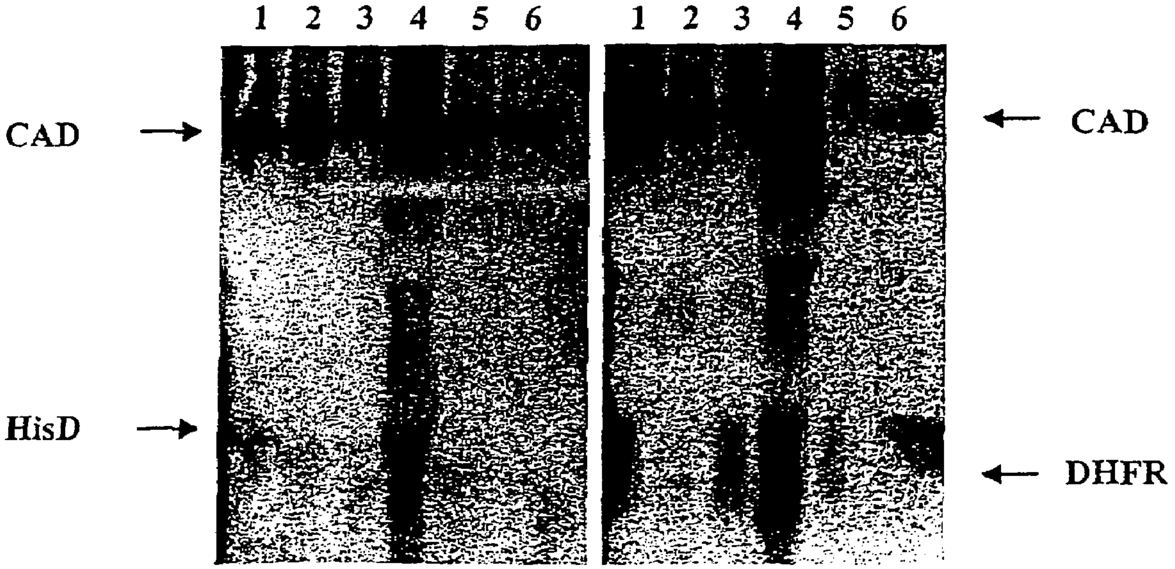

FIG. 5 shows a Northern analysis of single copy Desmond clones. Samples are as follows: Panel A: northern probed with CAD and DHFR probes, as indicated on the figure. Panel B: duplicate northern, probed with CAD and HisD probes, as indicated. The RNA samples loaded in panels A and B are as follows: Lane 1: clone 9B2, lane 2; clone 10C12, lane 3; clone 14B5, lane 4; clone 15C9, lane 5; control RNA from CHO transfected with a HisD and DHFR containing plasmid, lane 6; untransfected CHO.

Figure 6:
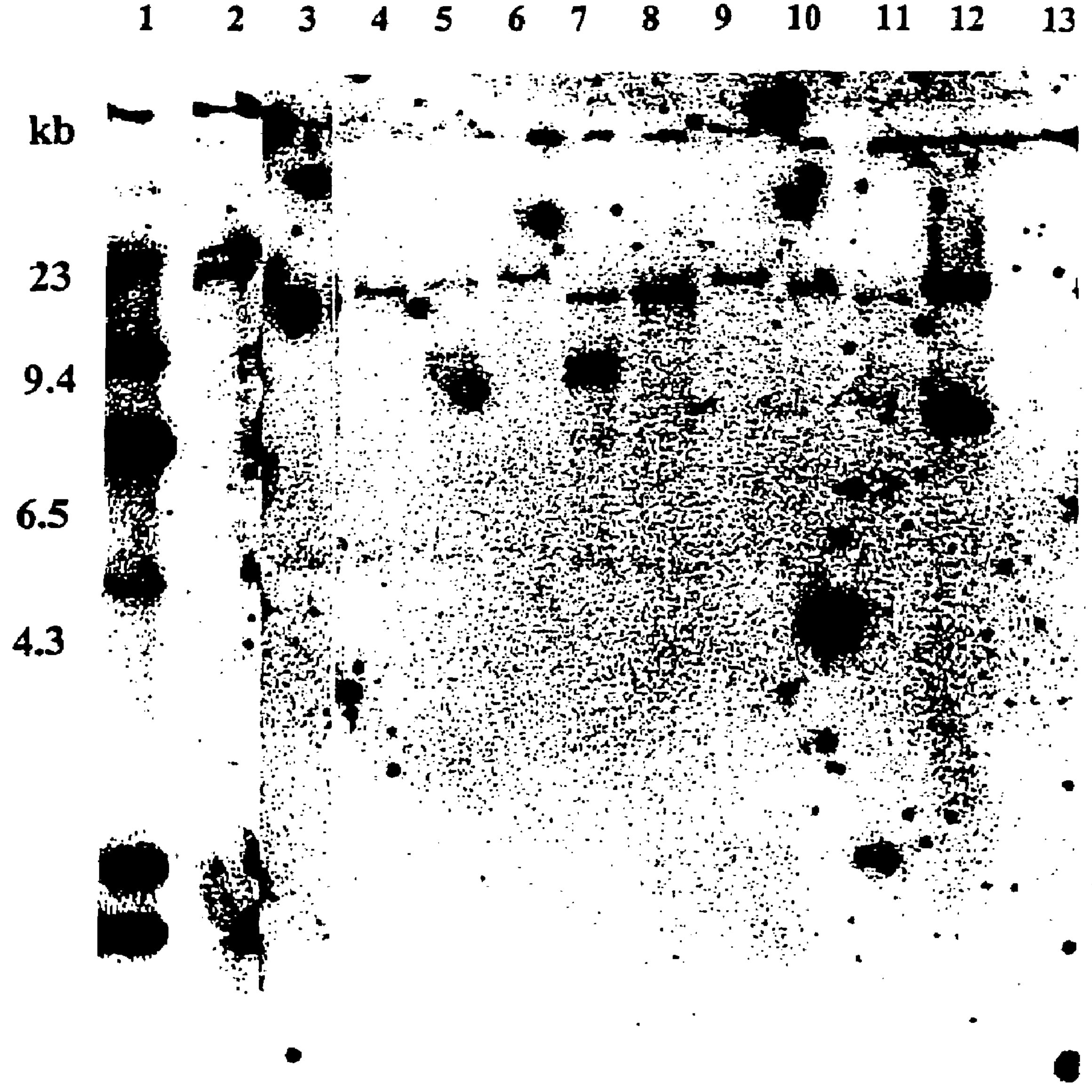

FIG. 6 shows a Southern analysis of clones resulting from the homologous integration of Molly into Desmond. Samples are as follows: Lane 1: λHindIII DNA size markers, Lane 2: 20F4, lane 3; 5F9, lane 4; 21C7, lane 5; 24G2, lane 6; 25E1, lane 7; 28C9, lane 8; 29F9, lane 9; 39G11, lane 10; 42F9, lane 11; 50G10, lane 12; Molly plasmid DNA, linearized with BglII(top band) and cut with BglII and KpnI (lower band), lane 13; untransfected Desmond.

FIGS. 7A through 7N and 7P–7X (SEQ ID NO:1) contain the nucleic acid sequence of Desmond.

FIGS. 8A through 8N and 8P–8X (SEQ ID NO:2) contain the nucleic acid sequence of Molly containing genes encoding the anti-CD20 antibody C2B8 as disclosed in Example 4.

FIG. 9 contains a map of the targeting plasmid, "Mandy," shown here encoding anti-CD23 genes, the expression of which is disclosed in Example 5.

FIGS. 10A through 10N and 10P–10U (SEQ ID NO:3) contain the nucleic acid sequence of "Mandy" containing genes encoding the anti-CD23 antibody 5E8 as disclosed in Example 5.

DETAILED DESCRIPTION OF THE INVENTION

The invention provides a novel method for integrating a desired exogenous DNA at a target site within the genome of a mammalian cell via homologous recombination. Also, the invention provides novel vectors for achieving the site specific integration of a DNA at a target site in the genome of a mammalian cell.

More specifically, the subject cloning method provides for site specific integration of a desired DNA in a mammalian cell by transfection of such cell with a "marker plasmid" which contains a unique sequence that is foreign to the mammalian cell genome and which provides a substrate for homologous recombination, followed by transfection with a "target plasmid" containing a sequence which provides for homologous recombination with the unique sequence contained in the marker plasmid, and further comprising a desired DNA that is to be integrated into the mammalian cell. Typically, the integrated DNA will encode a protein of interest, such as an immuncglobulin or other secreted mammalian glycoprotein.

The exemplified homologous recombination system uses the neomycin phosphotransferase gene as a dominant selectable marker. This particular marker was utilized based on the following previously published observations;

(i) the demonstrated ability to target and restore function to a mutated version of the neo gene (cited earlier) and (ii) our development of translationally impaired expression vectors, in which the neo gene has been artificially created as two exons with a gene of interest inserted in the intervening intron; neo exons are correctly spliced and translated in vivo, producing a functional protein and thereby conferring G418 resistance on the resultant cell population. In this application, the neo gene is split into three exons. The third exon of neo is present on the "marker" plasmid and becomes integrated into the host cell genome upon integration of the marker plasmid into the mammalian cells. Exons 1 and 2 are present on the targeting plasmid, and are separated by an intervening intron into which at least one gene of interest is cloned. Homologous recombination of the targeting vector with the integrated marking vector results in correct splicing of all three exons of the neo gene and thereby expression of a functional neo protein (as determined by selection for G418 resistant colonies). Prior to designing the current expression system, we had experimentally tested the functionality of such a triply spliced neo construct in mammalian cells. The results of this control experiment indicated that all three neo exons were properly spliced and therefore suggested the feasibility of the subject invention.

However, while the present invention is exemplified using the neo gene, and more specifically a triple split neo gene, the general methodology should be efficacious with other dominant selectable markers.

As discussed in greater detail infra, the present invention affords numerous advantages to conventional gene expression methods, including both random integration and gene targeting methods. Specifically, the subject invention provides a method which reproducibly allows for site-specific integration of a desired DNA into a transcriptionally active domain of a mammalian cell. Moreover, because the subject method introduces an artificial region of "homology" which acts as a unique substrate for homologous recombination and the insertion of a desired DNA, the efficacy of subject invention does not require that the cell endogenously contain or express a specific DNA. Thus, the method is generically applicable to all mammalian cells, and can be used to express any type of recombinant protein.

The use of a triply spliced selectable marker, e.g., the exemplified triply spliced neo construct, guarantees that all G418 resistant colonies produced will arise from a homologous recombination event (random integrants will not produce a functional neo gene and consequently will not survive G418 selection). Thus, the subject invention makes it easy to screen for the desired homologous event. Furthermore, the frequency of additional random integrations in a cell that has undergone a homologous recombination event appears to be low.

Based on the foregoing, it is apparent that a significant advantage of the invention is that it substantially reduces the number of colonies that need be screened to identify high producer clones, i.e., cell lines containing a desired DNA which secrete the corresponding protein at high levels. On average, clones containing integrated desired DNA may be identified by screening about 5 to 20 colonies (compared to several thousand which must be screened when using standard random integration techniques, or several hundred using the previously described intronic insertion vectors) Additionally, as the site of integration was preselected and comprises a transcriptionally active domain, all exogenous DNA expressed at this site should produce comparable, i.e. high levels of the protein of interest.

Moreover, the subject invention is further advantageous in that it enables an amplifiable gene to be inserted on integration of the marking vector. Thus, when a desired gene is targeted to this site via. homologous recombination, the subject invention allows for expression of the gene to be further enhanced by gene amplification. In this regard, it has been reported in from the literature that different qenomic sites have different capacities for gene amplification (Meinkoth et al, *Mol. Cell Biol.,* 7:1415–1424 (1987)). Therefore, this technique is further advantageous as it allows for the placement of a desired gene of interest at a specific site that is both transcriptionally active and easily amplified. Therefore, this should significantly reduce the amount of time required to isolate such high producers.

Specifically, while conventional methods for the construction of high expressing mammalian cell lines can take 6 to 9 months, the present invention allows for such clones to be isolated on average after only about 3–6 months. This is due to the fact that conventionally isolated clones typically must be subjected to at least three rounds of drug resistant gene amplification in order to reach satisfactory levels of gene expression. As the homologously produced clones are generated from a preselected site which is a high expression site, fewer rounds of amplification should be required before reaching a satisfactory level of production.

Still further, the subject invention enables the reproducible selection of high producer clones wherein the vector is integrated at low copy number, typically single copy. This is advantageous as it enhances the stability of the clones and avoids other potential adverse side-effects associated with high copy number. As described supra, the subject homologous recombination system uses the combination of a "marker plasmid" and a "targeting plasmid" which are described in more detail below.

The "marker plasmid" which is used to mark and identify a transcriptionally hot spot will comprise at least the following sequences:

(i) a region of DNA that is heterologous or unique to the genome of the mammalian cell, which functions as a source of homology, allows for homologous recombination (with a DNA contained in a second target plasmid). More specifically, the unique region of DNA (i) will generally comprise a bacterial, viral, yeast synthetic, or other DNA which is not normally present in the mammalian cell genome and which further does not comprise significant homology or sequence identity to DNA contained in the genome of the mammalian cell. Essentially, this sequence should be sufficiently different to mammalian DNA that it will not significantly recombine with the host cell genome via homologous recombination. The size of such unique DNA will generally be at least about 2 to 10 kilobases in size, or higher, more preferably at least about 10 kb, as several other investigators have noted an increased frequency of targeted recombination as the size of the homology region is increased (Capecchi, *Science,* 244:1288–1292 (1989)).

The upper size limit of the unique DNA which acts as a site for homologous recombination with a sequence in the second target vector is largely dictated by potential stability constraints (if DNA is too large it may not be easily integrated into a chromosome and the difficulties in working with very large DNAs.

(ii) a DNA including a fragment of a selectable marker DNA, typically an exon of a dominant selectable marker gene. The only essential feature of this DNA is that it not encode a functional selectable marker protein unless it is expressed in association with a sequence contained in the target plasmid. Typically, the target plasmid will comprise the remaining exons of the dominant selectable marker gene (those not comprised in "targeting" plasmid). Essentially, a functional selectable marker should only be produced if homologous recombination occurs (resulting in the association and expression of this marker DNA (i) sequence together with the portion(s) of the selectable marker DNA fragment which is (are) contained in the target plasmid).

As noted, the current invention exemplifies the use of the neomycin phosphotransferase gene as the dominant selectable marker which is "split" in the two vectors. However, other selectable markers should also be suitable, e.g., the *Salmonella* histidinol dehydrogenase gene, hygromycin phosphotransferase gene, herpes simplex virus thymidine kinase gene, adenosine deaminase gene, glutamine synthetase gene and hypoxanthine-guanine phosphoribosyl transferase gene.

(iii) a DNA which encodes a functional selectable marker protein, which selectable marker is different from the selectable marker DNA (ii). This selectable marker provides for the successful selection of mammalian cells wherein the marker plasmid is successfully integrated into the cellular DNA. More preferably, it is desirable that the marker plasmid comprise two such dominant selectable marker DNAs, situated at opposite ends of the vector. This is advantageous as it enables integrants to be selected using different selection agents and further enables cells which contain the entire vector to be selected. Additionally, one marker can be an amplifiable marker to facilitate gene dominant selectable marker listed in (ii) can be used as well as others generally known in the art.

Moreover, the marker plasmid may optionally further comprise a rare endonuclease restriction site. This is potentially desirable as this may facilitate cleavage. If present, such rare restriction site should be situated close to the middle of the unique region that acts as a substrate for homologous recombination. Preferably such sequence will be at least about 12 nucleotides. The introduction of a double stranded break by similar methodology has been reported to enhance the frequency of homologous recombination. (Choulika et al, *Mol. Cell. Biol.,* 15:1968–1973 (1995)). However, the presence of such sequence is not essential.

The "targeting plasmid" will comprise at least the following sequences:

(1) the same unique region of DNA contained in the marker plasmid or one having sufficient homology or sequence identity therewith that said DNA is capable of combining via homologous recombination with the unique region (i) in the marker plasmid. Suitable types of DNAs are described supra in the description of the unique region of DNA (1) in the marker plasmid.

(2) The remaining exons of the dominant selectable marker, one exon of which is included as (ii) in the marker plasmid listed above. The essential features of this DNA fragment is that it result in a functional (selectable) marker protein only if the target plasmid integrates via homologous recombination (wherein such recombination results in the association of this DNA with the other fragment of the selectable marker DNA contained in the marker plasmid) and further that it allow for insertion of a desired exogenous DNA. Typically, this DNA will comprise the remaining exons of the selectable marker DNA which are separated by an intron. For example, this DNA may comprise the first two exons of the neo gene and the marker plasmid may comprise the third exon (back third of neo).

(3) The target plasmid will also comprise a desired DNA, e.g., one encoding a desired polypeptide, preferably inserted within the selectable marker DNA fragment contained in the plasmid. Typically, the DNA will be inserted in an intron which is comprised between the exons of the selectable marker DNA. This ensures that the desired DNA is also integrated if homologous recombination of the target plasmid and the marker plasmid occurs. This intron may be naturally occurring or it may be engineered into the dominant selectable marker DNA fragment.

This DNA will encode any desired protein, preferably one having pharmaceutical or other desirable properties. Most typically the DNA will encode a mammalian protein, and in the current examples provided, an immunoglobulin or an immunoadhesin. However the invention is not in any way limited to the production of immunoglobulins.

As discussed previously, the subject cloning method is suitable for any mammalian cell as it does not require for efficacy that any specific mammalian sequence or sequences be present. In general, such mammalian cells will comprise those typically used for protein expression, e.g., CHO cells, myeloma cells, COS cells, BHK cells, Sp2/0 cells, NIH 3T3 and HeLa cells. In the examples which follow, CHO cells were utilized. The advantages thereof include the availability of suitable growth medium, their ability to crow efficiently and to high density in culture, and their ability to express mammalian proteins such as immunoglobulins in biologically active form.

Further, CHO cells were selected in large part because of previous usage of such cells by the inventors for the expression of immunoglobulins (using the translationally impaired dominant selectable marker containing vectors described previously). Thus, the present laboratory has considerable experience in using such cells for expression. However, based on the examples. which follow, it is reasonable to expect similar results will be obtained with other mammalian cells.

In general, transformation or transfection of mammalian cells according to the subject invention will be effected according to conventional methods. So that the invention may be better understood, the construction of exemplary vectors and their usage in producing integrants is described in the examples below.

EXAMPLE 1

Design and Preparation of Marker and Targeting Plasmid DNA Vectors

The marker plasmid herein referred to as "Desmond" was assembled from the following DNA elements:

(a) Murine dihydrofolate reductase gene (DHFR), incorporated into a transcription cassette, comprising the mouse beta globin promoter 5" to the DHFR start site, and bovine growth hormone poly adenylation signal 3" to the stop codon. The DHFR transcriptional cassette was isolated from TCAE6, an expression vector created previously in this laboratory (Newman et al, 1992, *Bio-technology,* 10:1455–1460).

(b) *E. coli* β-galactosidase gene—commercially available, obtained from Promega as pSV-b-galactosidase control vector, catalog #E1081.

(c) Baculovirus DNA, commercially available, purchased from Clontech as pBAKPAK8, cat #6145-1.

(d) Cassette comprising promoter and enhancer elements from Cytomegalovirus and SV40 virus. The cassette was generated by PCR using a derivative of expression vector TCAE8 (Reff et al, *Blood,* 83:435–445 (1994)). The enhancer cassette was inserted within the baculovirus sequence, which was first modified by the insertion of a multiple cloning site.

(e) *E. coli* GUS (glucuronidase) gene, commercially available, purchased from Clontech as pB101, cat. #6017-1.

(f) Firefly luciferase gene, commercially available, obtained from Promega as pGEM-Luc (catalog #E1541).

(g) *S. typhimurium* histidinol dehydrogenase gene (HisD). This gene was originally a gift from (Donahue et el, *Gene,* 18:47–59 (1982)), and has subsequently been incorporated into a transcription cassette comprising the mouse beta globin major promoter 5' to the gene, and the SV40 polyadenylation signal 3' to the gene.

The DNA elements described in (a)–(g) were combined into a pBR derived plasmid backbone to produce a 7.7 kb contiguous stretch of DNA referred to in the attached figures as "homology". Homology in this sense refers to sequences of DNA which-are not part of the mammalian genome and are used to promote homologous recombination between transfected plasmids sharing the same homology DNA sequences.

(h) Neomycin phosphotransferase gene from TN5 (Davis and Smith, *Ann. Rev. Micro.,* 32:469–518 (1978)). The complete neo gene was subcloned into pBluescript SK- (Stratagene catalog #212205) to facilitate genetic manipulation. A synthetic linker was then inserted into a unique Pst1 site occurring across the codons for amino acid 51 and 52 of neo. This linker encoded the necessary DNA elements to create an artificial splice donor site, intervening intron and splice acceptor site within the neo gene, thus creating two separate exons, presently referred to as neo exon 1 and 2. Neo exon 1 encodes the first 51 amino acids of neo, while exon 2 encodes the remaining 203 amino acids plus the stop codon of the protein A Not1 cloning site was also created within the intron.

Neo exon 2 was further subdivided to produce neo exons 2 and 3. This was achieved as follows: A set of PCR primers were designed to amplify a region of DNA encoding neo exon 1, intron and the first 111 ⅔ amino acids of exon2. The 3' PCR primer resulted in the introduction of a new 5' splice site immediately after the second nucleotide of the codon for amino acid 111 in exon 2, therefore generating a new smaller exon 2. The DNA fragment now encoding the original exon 1, intron and new exon 2 was then subcloned and propagated in a pBR based vector. The remainder of the original exon 2 was used as a template for another round of PCR amplification, which generated "exon3". The 5' primer for this round of amplification introduced a new splice acceptor site at the 5' side of the newly created exon 3, i.e. before the final nucleotide of the codon for amino acid 111. The resultant 3 exons of neo encode the following information: exon 1—the first 51 amino acids of neo; exon 2—the next 111 ⅔ amino acids, and exon 3 the final 91 ⅓ amino acids plus the translational stop codon of the neo gene.

Neo exon 3 was incorporated along with the above mentioned DNA elements into the marking plasmid "Desmond". Neo exons 1 and 2 were incorporated into the targeting plasmid "Molly". The Not1 cloning site created within the intron between exons 1 and 2 was used in subsequent cloning steps to insert genes of interest into the targeting plasmid.

A second targeting plasmid "Mandy" was also generated. This plasmid is almost identical to "Molly" (some restriction sites on the vector have been changed) except that the original HisD and DHFR genes contained in "Molly" were inactivated. These changes were incorporated because the Desmond cell line was no longer being cultured in the presence of Histidinol, therefore it seemed unnecessary to include a second copy of the HisD gene. Additionally, the DHFR gene was inactivated to ensure that only a single DHFR gene, namely the one present in the Desmond marked site, would be amplifiable in any resulting cell lines. "Mandy" was derived from "Molly" by the following modifications:

(i) A synthetic linker was inserted in the middle of the DHFR coding region. This linker created a stop codon and shifted the remainder of the DHFR coding region out of frame, therefore rendering the gene nonfunctional.

(ii) A portion of the HisD gene was deleted and replaced with a PCR generated HisD fragment lacking the promoter and start codon of the gene.

Figure 1A:
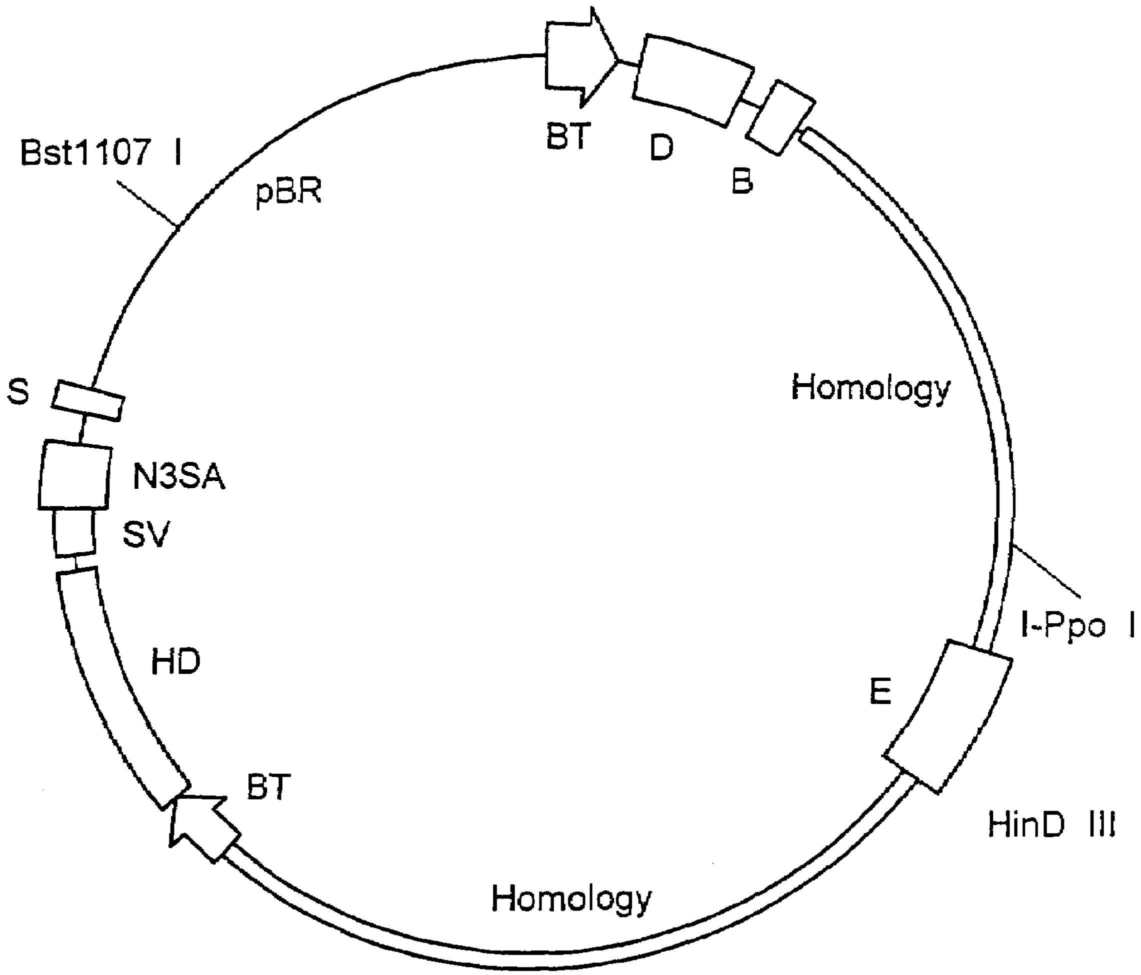
FIG. 1 depicts a map of a marking plasmid according to the invention referred to as Desmond. The plasmid is shown in circular form (1*a*) as well as a linearized version used for transfection (1*b*).
Figure 1B:
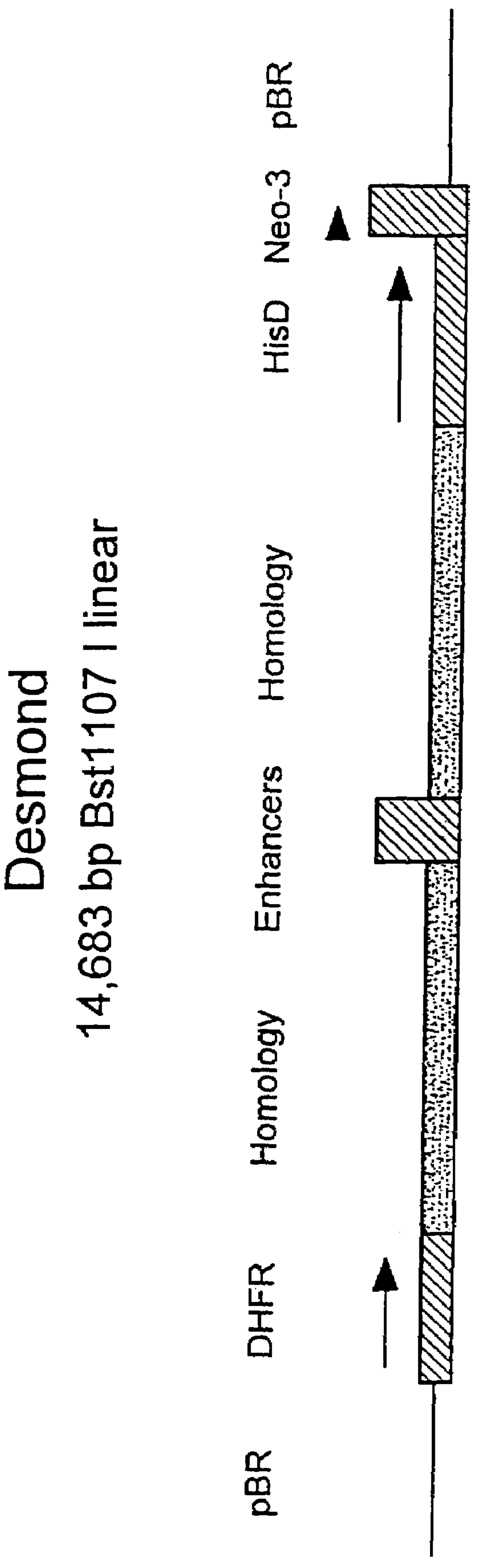
Figure 2B:
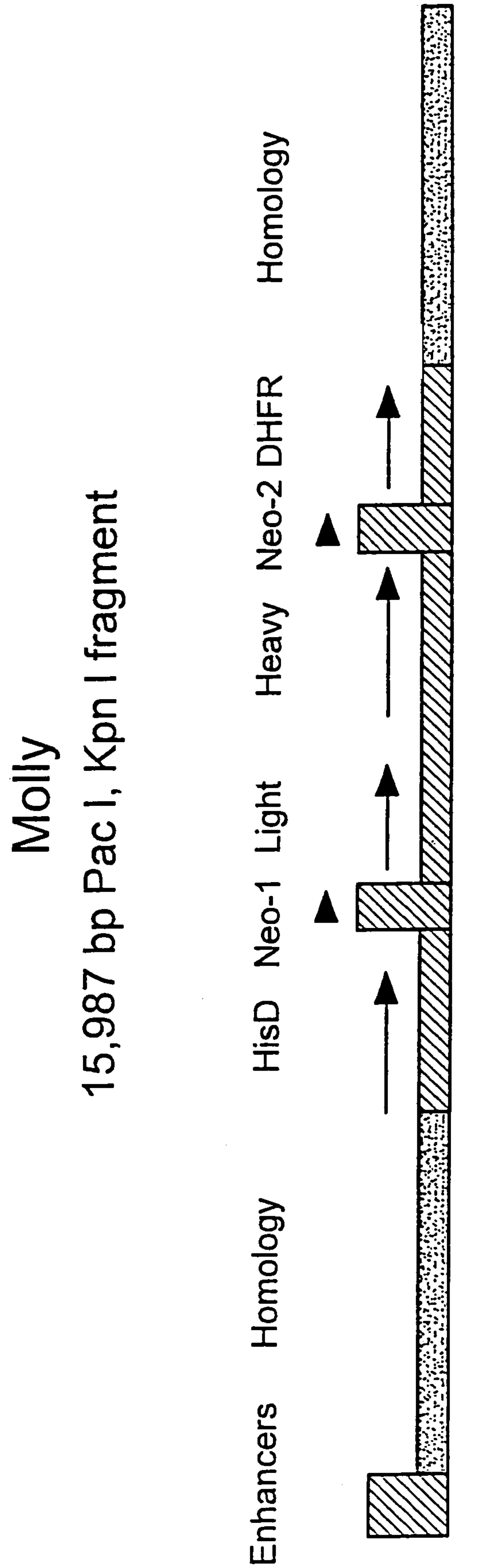
FIG. 2(*a*) shows a map of a targeting plasmid referred to "Molly". Molly is shown here encoding the anti-CD20 immunoglobulin genes, expression of which is described in Example 1.
Figure 3:
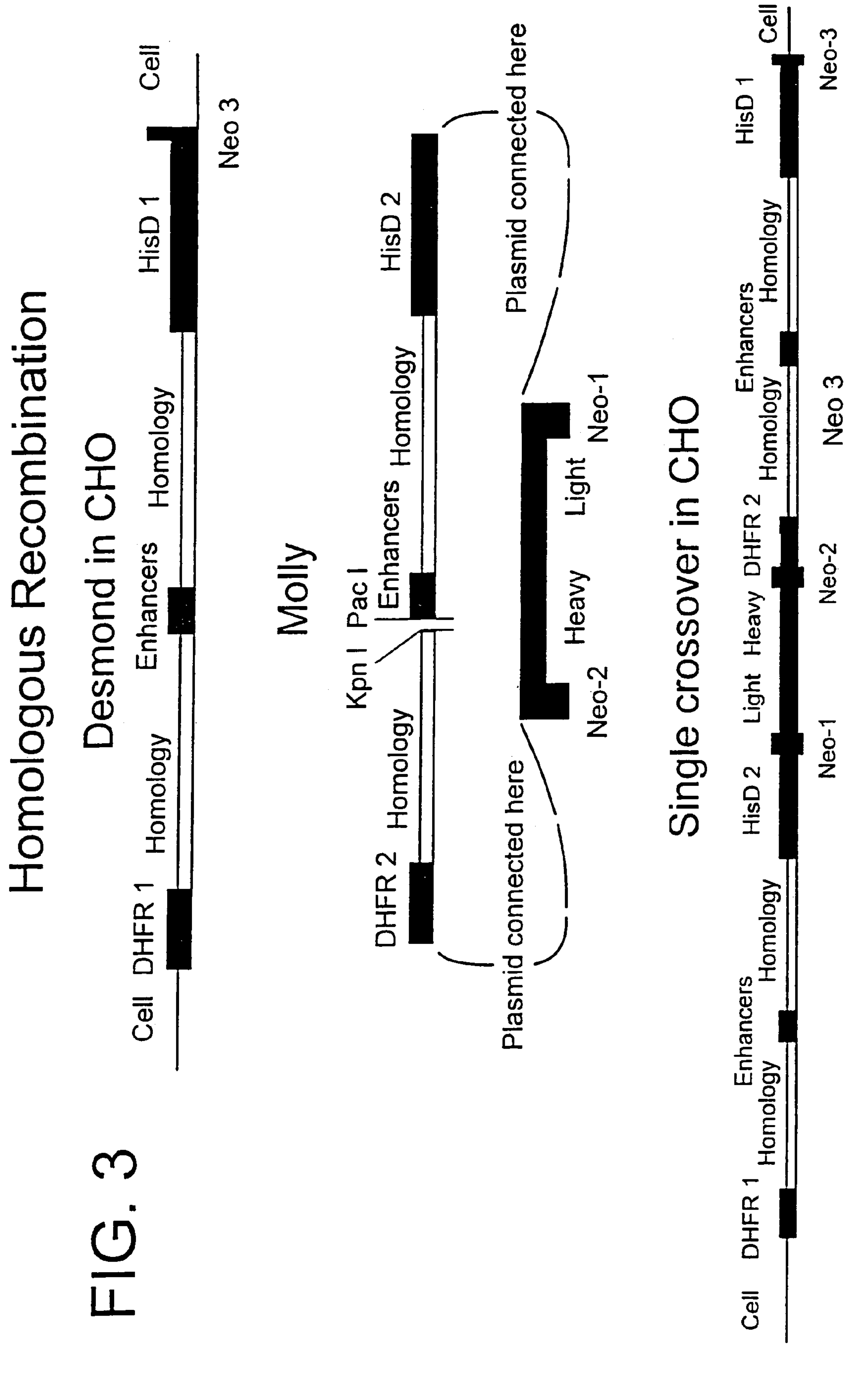
FIG. 3 depicts the potential alignment between Desmond sequences integrated into the CHO genome, and incoming targeting Molly sequences. One potential arrangement of Molly integrated into Desmond after homologous recombination is also presented.

FIG. 1 depicts the arrangement of these DNA elements in the marker plasmid "Desmond". FIG. 2 depicts the arrangement of these elements in the first targeting plasmid, "Molly". FIG. 3 illustrates the possible arrangement in the CHO genome, of the various DNA elements after targeting and integration of Molly DNA into Desmond marked CHO cells. FIG. 9 depicts the targeting plasmid "Mandy."

Construction of the marking and targeting plasmids from the above listed DNA elements was carried out following conventional cloning techniques (see, e.g., Molecular Cloning, A Laboratory Manual, J. Sambrook et al, 1987, Cold Spring Harbor Laboratory Press, and Current Protocols in Molecular Biology, F. M. Ausubel et al, eds., 1987, John Wiley and Sons). All plasmids were propagated and maintained in *E. coli* XLI blue (Stratagene, cat. #200236). Large scale plasmid preparations were prepared using Promega Wizard Maxiprep DNA Purification System®, according to the manufacturer's directions.

EXAMPLE 2

Construction of a Marked CHO Cell Line

1. Cell Culture and Transfection Procedures to Produced Marked CHO Cell Line

Marker plasmid DNA was linearized by digestion overnight at 37° C. with Bst1107I. Linearized vector was ethanol precipitated and resuspended in sterile TE to a concentration of 1 mg/ml. Linearized vector was introduced into DHFR- Chinese hamster ovary cells (CHO cells) DG44 cells (Urlaub et al, *Som. Cell and Mol. Gen.,* 12:555–566 (1986)) by electroporation as follows.

Exponentially growing cells were harvested by centrifugation, washed once in ice cold SBS (sucrose buffered solution, 272 mM sucrose, 7 mM sodium phosphate, pH 7.4, 1 mM magnesium chloride) then resuspended in SBS to a concentration of $10^7$ cells/ml. After a 15 minute incubation on ice, 0.4 ml of the cell suspension was mixed with 40 μg linearized DNA in a disposable electroporation cuvette. Cells were shocked using a BTX electrocell manipulator (San Diego, Calif.) set at 230 volts, 400 microfaraday capacitance, 13 ohm resistance. Shocked cells were then mixed with 20 ml of prewarmed CHO growth media (CHO-S-SFMII, Gibco/BRL, catalog #31033-012) and plated in 96 well tissue culture plates. Forty eight hours after electroporation, plates were fed with selection media (in the case of transfection with Desmond, selection media. is CHO-S-SFMII without hypoxanthine or thymidine, supplemented with 2 mM Histidinol (Sigma catalog #H6647)). Plates were maintained in selection media for up to 30 days, or until some of the wells exhibited cell growth. These cells were then removed from the 96 well plates and expanded ultimately to 120 ml spinner flasks where they were maintained in selection media at all times.

EXAMPLE 3

Characterization of Marked CHO Cell Lines (a) Southern Analysis

Figure 4:
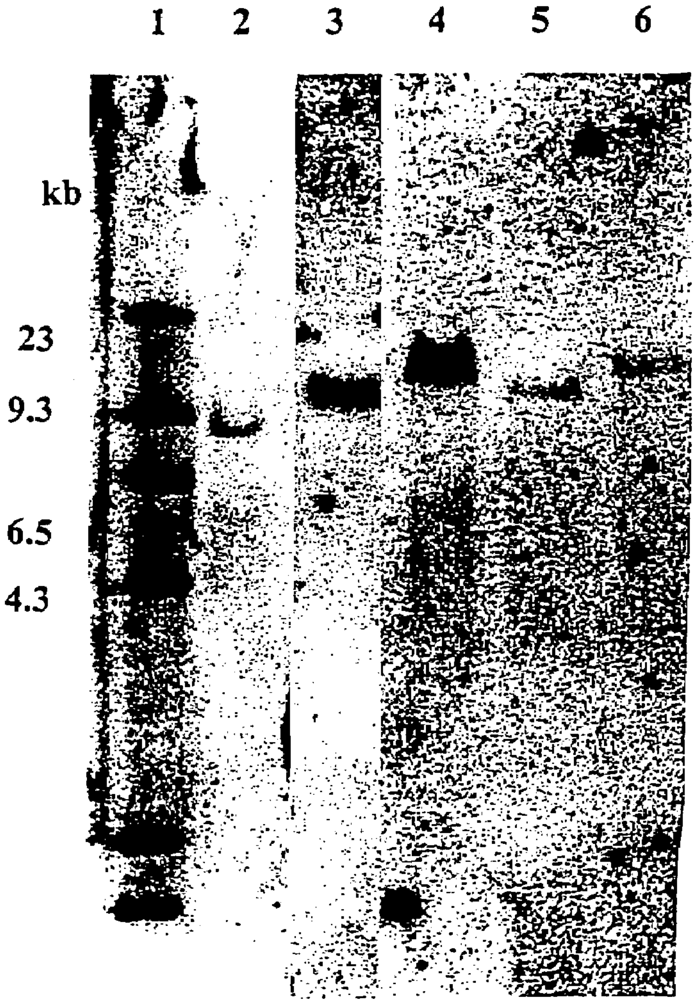
FIG. 4 shows a Southern analysis of single copy Desmond clones. Samples are as follows.

Genomic DNA was isolated from all stably growing Desmond marked CHO cells. DNA was isolated using the Invitrogen Easy® DNA kit, according to the manufacturer's directions. Genomic DNA was then digested with HindIII overnight at 37° C., and subjected to Southern analysis using a PCR generated digoxygenin labelled probe specific to the DHFR gene. Hybridizations and washes were carried out using Boehringer Mannheim's DIG easy hyb (catalog #1603 558) and DIG Wash and Block Buffer Set (catalog #1585 762) according to the manufacturer's directions. DNA samples containing a single band hybridizing to the DHFR probe were assumed to be Desmond clones arising from a single cell which had integrated a single copy of the plasmid. These clones were retained for further analysis. Out of a total of 45 HisD resistant cell lines isolated, only 5 were single copy integrants. FIG. 4 shows a Southern blot containing all 5 of these single copy Desmond clones. Clone names are provided in the figure legend.

(b) Northern Analysis

Total RNA was isolated from all single copy Desmond clones using TRIzol reagent (Gibco/BRL cat #15596-026) according to the manufacturer's directions. 10–20 μg RNA from each clone was analyzed on duplicate formaldehyde gels. The resulting blots were probed with PCR generated digoxygenin labelled DNA probes to (i) DHFR message, (ii) HisD message and (iii) CAD message. CAD is a trifunctional protein involved in uridine biosynthesis (Wahl et al, *J. Biol. Chem.,* 254, 17:8679–8689 (1979)), and is expressed equally in all cell types. It is used here as an internal control to help quantitate RNA loading. Hybridizations and washes were carried out using the above mentioned Boehringer Mannheim reagents. The results of the Northern analysis are shown in FIG. 5. The single copy Desmond clone exhibiting the highest levels of both the His D and DHFR message is clone 15C9, shown in lane 4 in both panels of the figure. This clone was designated as the "marked cell line" and used in future targeting experiments in CHO, examples of which are presented in the following sections.

EXAMPLE 4

Expression of Anti-CD20 Antibody in Desmond Marked CHO Cells

C2B8, a chimeric antibody which recognizes B-cell surface antigen CD20, has been cloned and expressed previously. (Reff et al, *Blood,* 83:435–445 (1994)). A 4.1 kb DNA fragment comprising the C2B8 light and heavy chain genes, along with the necessary regulatory elements (eukaryotic promoter and polyadenylation signals) was inserted into the artificial intron created between exons 1 and 2 of the neo gene contained in a pBR derived cloning vector. This newly generated 5 kb fragment (comprising neo exon 1, C2B8 and neo exon 2) was excised and used to assemble the targeting plasmid Molly. The other DNA elements used in the construction of Molly are identical to those used to construct the marketing plasmid Desmond, identified previously. A complete map of Molly is shown in FIG. 2.

The targeting vector Molly was linearized prior to transfection by digestion with Kpn1 and Pac1, ethanol precipitated and resuspended in sterile TE to a concentration of 1.5 mg/mL. Linearized plasmid was introduced into exponentially growing Desmond marked cells essentially as described, except that 80 μg DNA was used in each electroporation. Forty eight hours postelectroporation, 96 well plates were supplemented with selection medium—CHO-SSFMII supplemented with 400 μg/mL Geneticin (G418, Gibco/BRL catalog #10131-019). Plates were maintained in selection medium for up to 30 days, or until cell growth occurred in some of the wells. Such growth was assumed to be the result of clonal expansion of a single G418 resistant cell. The supernatants from all G418 resistant wells were assayed for C2B8 production by standard ELISA techniques, and all productive clones were eventually expanded to 120 mL spinner flasks and further analyzed.

Characterization of Antibody secreting Targeted Cells

A total of 50 electroporations with Molly targeting plasmid were carried out in this experiment, each of which was plated into separate 96 well plates. A total of 10 viable, anti-CD20 antibody secreting clones were obtained and expanded to 120 ml spinner flasks. Genomic DNA was isolated from all clones, and Southern analyses were subsequently performed to determine whether the clones represented single homologous recombination events or whether additional random integrations had occurred in the same cells. The methods for DNA isolation and Southern hybridization were as described in the previous section. Genomic DNA was digested with EcoRI and probed with a PCR generated digoxygenin labelled probe to a segment of the CD20 heavy chain constant region. The results of this Southern analysis are presented in FIG. 6. As can be seen in the figure, 8 of the 10 clones show a single band hybridizing to the CD20 probe, indicating a single homologous recombination event has occurred in these cells. Two of the ten, clones 24G2 and 28C9, show the presence of additional band(s), indicative of an additional random integration elsewhere in the genome.

We examined the expression levels of anti-CD20 antibody in all ten of these clones, the data for which is shown in Table 1, below.

TABLE 1

Expression Level of Anti-CD20 Secreting Homologous Integrants

| Clone | Anti-CD20, pg/c/d |
|---|---|
| 20F4 | 3.5 |
| 25E1 | 2.4 |
| 42F9 | 1.8 |
| 39G11 | 1.5 |
| 21C7 | 1.3 |
| 50G10 | 0.9 |
| 29F9 | 0.8 |
| 5F9 | 0.3 |
| 28C9* | 4.5 |
| 24G2* | 2.1 |

*These clones contained additional randomly integrated copies of anti-CD20. Expression levels of these clones therefore reflect a contribution from both the homologous and random sites.

Expression levels are reported as picogram per cell per day (pg/c/d) secreted by the individual clones, and represented the mean levels obtained from three separate ELISAs on samples taken from 120 mL spinner flasks.

As can be seen from the data, there is a variation antibody secretion of approximately ten fold between highest and lowest clones. This was somewhat unexpected as we anticipated similar expression levels from clones due to the fact the anti-CD20 genes are all integrated into the same Desmond marked site. Nevertheless, this observed range in expression extremely small in comparison to that seen using any traditional random integration method or with our translationally impaired vector system.

Clone 20F4, the highest producing single copy integrant was selected for further study. Table 2 (below) presents ELISA and cell culture data from seven day production runs of this clone.

TABLE 2

7 Day Production Run Data for 20F4

| Day | % Viable | Viable/ml (×10$^{5)}$ | Tx2 (hr) | mg/L | pg/c/d |
|---|---|---|---|---|---|
| 1 | 96 | 3.4 | 31 | 1.3 | 4.9 |
| 2 | 94 | 6 | 29 | 2.5 | 3.4 |
| 3 | 94 | 9.9 | 33 | 4.7 | 3.2 |
| 4 | 90 | 17.4 | 30 | 6.8 | 3 |
| 5 | 73 | 14 | | 8.3 | |
| 6 | 17 | 3.5 | | 9.5 | |

Clone 20F4 was seeded at 2 × $10^5$ ml in a 120 ml spinner flask on day 0. On the following six days, cell counts were taken, doubling times calculated and 1 ml samples of supernatant removed from the flask and analyzed for secreted anti-CD20 by ELISA.

This clone is secreting on average, 3–5 pg antibody/—cell/day, based on this ELISA data. This is the same level as obtained from other high expressing single copy clones obtained previously in our laboratory using the previously developed translationally impaired random integration vectors. This result indicates the following:

(1) that the site in the CHO genome marked by the Desmond marking vector is highly transcriptionally active, and therefore represents an excellent site from which to express recombinant proteins, and (2) that targeting by means of homologous recombination can be accomplished using the subject vectors and occurs at a frequency high enough to make this system a viable and desirable alternative to random integration methods.

To further demonstrate the efficacy of this system, we have also demonstrated that this site is amplifiable, resulting in even higher levels of gene expression and protein secretion. Amplification was achieved by plating serial dilutions of 20F4 cells, starting at a density of 2.5×$10^4$ cells/ml, in 96 well tissue culture dishes, and culturing these cells in media (CHO-SSFMII) supplemented with 5, 10, 15 or 20 nM methotrexate. Antibody secreting clones were screened using standard ELISA techniques, and the highest producing clones were expanded and further analyzed. A summary of this amplification experiment is presented in Table 3 below.

TABLE 3

Summary of 20F4 Amplification

| nM MTX | # Wells Assayed | Expression Level mg/l 96 well | # Wells Expanded | Expression Level pg/c/d from spinner |
|---|---|---|---|---|
| 10 | 56 | 3–13 | 4 | 10–15 |
| 15 | 27 | 2–14 | 3 | 15–18 |
| 20 | 17 | 4–11 | 1 | ND |

Methotrexate amplification of 20F4 was set up as described in the text, using the concentrations of methotrexate indicated in the above table. Supernatants from all surviving 96 well colonies were assayed by ELISA, and the range of anti-CD20 expressed by these clones is indicated in column 3. Based on these results, the highest producing clones were expanded to 120 ml spinnersand several ELISAs conducted on the spinner supernatants to determine the pg/cell/day expression levels, reported in column 5.

The data here clearly demonstrates that this site can be amplified in the presence of methotrexate. Clones from the 10 and 15 nM amplifications were found to produce on the order of 15–20 pg/cell/day.

A 15 nM clone, designated 20F4-15A5, was selected as the highest expressing cell line. This clone originated from a 96 well plate in which only 22 wells grew, and was therefore assumed to have arisen from a single cell. A 15 nM clone, designated 20F4-15A5, was selected as the highest expressing cell line. This clone originated from a 96 well plate in which only 22 wells grew, and was therefore assumed to have arisen from a single cell. The clone was then subjected to a further round of methotrexate amplification. As described above, serial dilutions of the culture were plated into 96 well dishes and cultured in CHO-SS-FMII medium supplemented with 200, 300 or 400 nM methotrexate. Surviving clones were screened by ELISA, and several high producing clones were expanded to spinner cultures and further analyzed. A summary of this second amplification experiment is presented in Table 4.

TABLE 4

Summary of 20F4-15A5 Amplification

| nM MTX | # Wells Assayed | Expression Level mg/l 96 well | # Wells Expanded | Expression Level pg/c/d, spinner |
|---|---|---|---|---|
| 200 | 67 | 23–70 | 1 | 50–60 |
| 250 | 86 | 21–70 | 4 | 55–60 |
| 300 | 81 | 15–75 | 3 | 40–50 |

Methotrexate amplifications of 20F4-15AS were set up and assayed as described in the text. The highest producing wells, the numbers of which are indicated in column 4, were expanded to 120 ml spinner flasks. The expression levels of the cell lines derived from these wells is recorded as pg/c/d in column 5.

The highest producing clone came from the 250 nM methotrexate amplification. The 250 nM clone, 20F4-15A5-250A6 originated from a 96 well plate in which only wells grew, and therefore is assumed to have arisen from a single cell. Taken together, the data in Tables 3 and 4 strongly indicates that two rounds of methotrexate amplification are sufficient to reach expression levels of 60 pg/cell/day, which is approaching the maximum secretion capacity of immunoglobulin in mammalian cells (Reff, M. E., *Curr. Opin. Biotech.,* 4:573–576 (1993)). The ability to reach this secretion capacity with just two amplification steps further enhances the utility of this homologous recombination system. Typically, random integration methods require more than two amplification steps to reach this expression level and are generally less reliable in terms of the ease of amplification. Thus, the homologous system offers a more efficient and time saving method of achieving high level gene expression in mammalian cells.

EXAMPLE 5

Expression of Anti-Human CD23 Antibody in Desmond Marked CHO Cells

CD23 is low affinity IgE receptor which mediates binding of IgE to B and T lymphocytes (Sutton, B. J., and Gould, H. J., *Nature,* 366:421–428 (1993)). Anti-human CD23 monoclonal antibody 5E8 is a human gamma-I monoclonal antibody recently cloned and expressed in our laboratory. This antibody is disclosed in commonly assigned Ser. No. 08/803,085, filed on Feb. 20, 1997.

The heavy and light chain genes of 5E8 were cloned into the mammalian expression vector N5KG1, a derivative of the vector NEOSPLA (Barnett et al, in *Antibody Expression and Engineering,* H. Y Yang and T. Imanaka, eds., pp27–40 (1995)) and two modifications were then made to the genes. We have recently observed somewhat higher secretion of immunoglobulin light chains compared to heavy chains in other expression constructs in the laboratory (Reff et al, 1997, unpublished observations). In an attempt to compensate for this deficit, we altered the 5E8 heavy chain gene by the addition of a stronger promoter/enhancer element immediately upstream of the start site. In subsequent steps, a 2.9 kb DNA fragment comprising the 5E8 modified light and heavy chain genes was isolated from the N5KG1 vector and inserted into the targeting vector Mandy. Preparation of 5E8-containing Molly and electroporation into Desmond 15C9 CHO cells was essentially as described in the preceding section.

One modification to the previously described protocol was in the type of culture medium used. Desmond marked CHO cells were cultured in protein-free CD-CHO medium (Gibco-BRL, catalog #AS21206) supplemented with 3 mg/L recombinant insulin (3 mg/mL stock, Gibco-BRL, catalog #AS22057) and 8 mM L-glutamine (200 mM stock, Gibco-BRL, catalog #25030-081). Subsequently, transfected cells were selected in the above medium supplemented with 400 μg/mL geneticin. In this experiment, 20 electroporations were performed and plated into 96 well tissue culture dishes. Cells grew and secreted anti-CD23 in a total of 68 wells, all of which were assumed to be clones originating from a single G418 cell. Twelve of these wells were expanded to 120 ml spinner flasks for further analysis. We believe the increased number of clones isolated in this experiment (68 compared with 10 for anti-CD20 as described in Example 4) is due to a higher cloning efficiency and survival rate of cells grown in CD-CHO medium compared with CHO-SS-FMII medium. Expression levels for those clones analyzed in spinner culture ranged from 0.5–3 pg/c/d, in close agreement with the levels seen for the anti-CD20 clones. The highest producing anti-CD23 clone, designated 4H12, was subjected to methotrexate amplification in order to increase its expression levels. This amplification was set up in a manner similar to that described for the anti-CD20 clone in Example 4. Serial dilutions of exponentially growing 4H12 cells were plated into 96 well tissue culture dishes and grown in CD-CHO medium supplemented with 3 mg/L insulin, 8 mM glutamine and 30, 35 or 40 nM methotrexate. A summary of this amplification experiment is presented in Table 5.

TABLE 5

Summary of 2H12 Amplification

| nM MTX | # Wells Assayed | Expression Level mg/l 96 well | # Wells Expanded | Expression Level pg/c/d from spinner |
|---|---|---|---|---|
| 30 | 100 | 6–24 | 8 | 10–25 |
| 35 | 64 | 4–27 | 2 | 10–15 |
| 40 | 96 | 4–20 | 1 | ND |

The highest expressing clone obtained was a 30 nM clone, isolated from a plate on which 22 wells had grown. This clone, designated 4H12-30G5, was reproducibly secreting 18–22 pg antibody per cell per day. This is the same range of expression seen for the first amplification of the anti CD20 clone 20F4 (clone 20F4-15A5 which produced 15–18 pg/c/d, as described in Example 4). This dataserves to further support the observation that amplification at this marked site in CHO is reproducible and efficient. A second amplification of this 30 nM cell line is currently underway. It is anticipated that saturation levels of expression will be achievable for the anti-CD23 antibody in just two amplification steps, as was the case for anti-CD20.

EXAMPLE 6

Expression of Immunoadhesin in Desmond Marked CHO Cells

CTLA-4, a member of the Ig superfamily, is found on the surface of T lymphocytes and is thought to play a role in antigen-specific T-cell activation (Dariavach et al, *Eur. J. Immunol.,* 18:1901–1905 (1988); and Linsley et al, *J. Exp. Med.,* 174:561–569 (1991)). In order to further study the precise role of the CTLA-4 molecule in the activation pathway, a soluble fusion protein comprising the extracellular domain of CTLA-4 linked to a truncated form of the human IgG1 constant region was created (Linsley et al (Id.). We have recently expressed this CTLA-4 Ig fusion protein in the mammalian expression vector BLECH1, a derivative of the plasmid NEOSPLA (Barnett et al, in Antibody Expression and Engineering, H. Y Yang and T. Imanaka, eds., pp27–40 (1995)). An 800 bp fragment encoding the CTLA-4 Ig was isolated from this vector and inserted between the SacII and BglII sites in Molly.

Preparation of CTLA-4Ig-Molly and electroporation into Desmond clone 15C9 CHO cells was performed as described in the previous example relating to anti-CD20. Twenty electroporations were carried out, and plated into 96 well culture dishes as described previously. Eighteen CTLA-4 expressing wells were isolated from the 96 well plates and carried forward to the 120 ml spinner. stage. Southern analyses on genomic DNA isolated from each of these clones were then carried out to determine how many of the homologous clones contained additional random integrants. Genomic DNA was digested with BglII and probed with a PCR generated digoxygenin labelled probe to the human IgG1 constant region. The results of this analysis indicated that 85% of the CTLA-4 clones are homologous integrants only; the remaining 15% contained one additional random integrant. This result corroborates the findings from the expression of anti-CD20 discussed above, where 80% of the clones were single homologous integrants. Therefore, we can conclude that this expression system reproducibly yields single targeted homologous integrants in at least 80% of all clones produced.

Expression levels for the homologous CTlA4-Ig clones ranged from 8–12 pg/cell/day. This is somewhat higher than the range reported for anti-CD20 antibody and anti-CD23 antibody clones discussed above. However, we have previously observed that expression of this molecule using the intronic insertion vector system also resulted in significantly higher expression levels than are obtained for immunoglobulins. We are currently unable to provide an explanation for this observation.

EXAMPLE 7

Targeting Anti-CD20 to an-alternate Desmond Marked CHO Cell Line

As we described in a preceding section, we obtained 5 single copy Desmond marked CHO cell lines (see FIGS. 4 and 5). In order to demonstrate that the success of our targeting strategy is not due to some unique property of Desmond clone 15C9 and limited only to this clone, we introduced anti-CD20 Molly into Desmond clone 9B2 (lane 6 in FIG. 4, lane 1 in FIG. 5). Preparation of Molly DNA and electroporation into Desmond 9B2 was exactly as described in the previous example pertaining to anti-CD20. We obtained one homologous integrant from this experiment. This clone was expanded to a 120 ml spinner flask, where it produced on average 1.2 pg anti-CD20/cell/day. This is considerably lower expression than we observed with Molly targeted into Desmond 15C9. However, this was the anticipated result, based on our northern analysis of the Desmond clones. As can be seen in FIG. 5, mRNA levels from clone 9B2 are considerably lower than those from 15C9, indicating the site in this clone is not as transcriptionally active as that in 15C9. Therefore, this experiment not only demonstrates the reproducibility of the system—presumably any marked Desmond site can be targeted with Molly—it also confirms the northern data that the site in Desmond 15C9 is the most transcriptionally active.

From the foregoing, it will be appreciated that, although specific embodiments of the invention have been described herein for purposes of illustration, various modifications may be made without diverting from the scope of the invention. Accordingly, the invention is not limited by the appended claims.

What is claimed is:

1. A method for inserting a desired DNA at a target site in the genome of a mammalian cell which comprises the following steps:

(i) transfecting or transforming a mammalian cell in vitro with a marker plasmid comprising the following sequences:

(a) a first DNA fragment which comprises a region that is heterologous to the mammalian cell genome and provides a unique site for homologous recombination when it is integrated in the mammalian cell genome;

(b) a second DNA fragment which comprises at least one exon but not all of the exons of a gene encoding a first selectable marker protein; and (c) a third DNA fragment which comprises a region encoding a second selectable marker protein that is different from the first selectable protein and provides for selection of a mammalian cell which has said marker plasmid integrated into its genome;

(ii) selecting a cell which contains the marker plasmid integrated in its genome by screening in vitro for expression of a selectable marker protein encoded by said third DNA fragment;

(iii) transfecting or transforming said selected cell with a target plasmid which comprises at least one DNA to be inserted into the genome of said cell, and further comprises the following sequences:

(a) a fourth DNA fragment which comprises a region that is identical or is sufficiently homologous to the unique site for homologous recombination in the marker plasmid such that this region can recombine with said marker plasmid DNA via homologous recombination; and (b) a fifth DNA fragment which comprises the remaining exon or exons of the gene encoding a first selectable marker protein that are not present in the marker plasmid;

wherein an active first selectable marker protein is only produced if the at least one exon of a gene encoding a first selectable marker protein contained in the marker plasmid is expressed in association with the remaining exon or exons of the gene encoding a first selectable marker protein contained in the target plasmid; and (iv) selecting cells which contain the target plasmid integrated at the unique site for homologous recombination by screening in vitro for the expression of the first selectable marker protein.

2. The method of claim 1, wherein the at least one DNA to be inserted into the genome of said cell encodes a desired protein.

3. The method of claim 2, wherein the desired protein is a mammalian protein.

4. The method of claim 3, wherein the mammalian protein is an immunoglobulin.

5. The method of claim 1, wherein the at least one DNA to be inserted into the genome of said cell is inserted adjacent to an exon of said first selectable marker contained in the target plasmid.

6. The method of claim 1, wherein the first selectable marker protein is selected from the group consisting of neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase.

7. The method of claim 6, wherein the at least one exon of the gene encoding the first selectable marker protein in the marker plasmid contains a portion of a neomycin phosphotransferase gene, and the remaining exons in the target plasmid contain the remaining portions of said neomycin phosphotransferase gene.

8. The method of claim 1, which further comprises determining the RNA levels of the second selectable marker contained in said third DNA fragment of the marker plasmid prior to integration of the target vector.

9. The method of claim 1, wherein the second selectable marker protein which is different from said first selectable marker protein is selected from the group consisting of neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine guanine phosphoribosyl transferase.

10. The method of claim 1, wherein the marker or the target plasmid further comprises a DNA encoding a third selectable marker protein that is different from the first and second selectable marker proteins.

11. The method claim 10, wherein expression of the DNA encoding a third selectable marker protein permits amplification of said DNA to be inserted into the genome of said cell.

12. The method claim 11, wherein the third selectable marker protein is dihydrofolate reductase.

13. The method of claim 1, wherein the mammalian cell is selected from the group consisting of Chinese hamster ovary (CHO) cells, myeloma cells, baby hamster kidney cells, COS cells, NSO cells, HeLa cells and NIH 3T3 cells.

14. The method of claim 13, wherein the cell is a CHO cell.

15. The method of claim 1, wherein the marker plasmid further contains a rare restriction endonuclease sequence which is inserted within the region of DNA in the first DNA fragment of the marker plasmid that provides a unique site for homologous recombination.

16. The method of claim 1, wherein the region of DNA in the first DNA fragment that provides a unique site for homologous recombination is at least 300 nucleotides.

17. The method of claim 16, wherein the region of DNA in the first DNA fragment that provides a unique site for homologous recombination ranges in size from about 300 nucleotides to 20 kilobases.

18. The method of claim 17, wherein the region of DNA in the first DNA fragment that provides a unique site for homologous recombination ranges in size from 2 to 10 kilobases.

19. The method of claim 1, wherein the DNA encoding the first selectable marker protein is split into at least three exons.

20. The method of claim 1, wherein the region of DNA in the first DNA fragment that provides a unique site for homologous recombination is a bacterial DNA, an insect DNA, a viral DNA or a synthetic DNA.

21. The method of claim 20, wherein the region of DNA in the first DNA fragment that provides a unique site for homologous recombination does not contain any functional genes.

22. A vector system for inserting a desired DNA at a target site in the genome of a mammalian cell in vitro which comprises at least the following:

(i) a marker plasmid comprising the following sequences:

(a) a first DNA fragment which comprises a region of DNA that is heterologous to the mammalian cell genome and provides a unique site for homologous recombination when it is integrated in the mammalian cell genome;

(b) a second DNA fragment which comprises at least one exon but not all of the exons of a gene encoding a first selectable marker protein; and (c) a third DNA fragment which comprises a region encoding a second selectable marker protein that is different from the first selectable protein and provides for selection of a mammalian cell in vitro which has said marker plasmid integrated into its genome; and (ii) a target plasmid which comprises at least one DNA to be inserted into the genome of said cell, and further comprises the following sequences:

(a) a fourth DNA fragment which comprises a region that is identical or is sufficiently homologous to the unique site for homologous recombination in the marker plasmid such that this region of DNA can recombine with said marker plasmid DNA via homologous recombination;

(b) a fifth DNA fragment which comprises the remaining exon or exons of the gene encoding a first selectable marker protein that are not present in the marker plasmid;

wherein the at least one exon of a gene encoding a first selectable marker protein in the marker plasmid and the remaining exon or exons of the gene encoding a first selectable marker protein in the target plasmid together encode an active first selectable marker protein.

23. The vector system of claim 22, wherein the at least one DNA to be inserted into the genome of said cell encodes a desired protein.

24. The vector system of claim 23, wherein the desired protein is a mammalian protein.

25. The vector system of claim 24, wherein the mammalian protein is an immunoglobulin.

26. The vector system of claim 22, wherein the at least one DNA to be inserted into the genome of said cell is inserted adjacent to an exon of said first selectable marker contained in the target plasmid.

27. The vector system of claim 22, wherein the first selectable marker protein is selected from the group consisting of neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine guanine phosphoribosyl transferase.

28. The vector system of claim 27, wherein the at least one exon of the gene encoding the first selectable marker protein in the marker plasmid contains a portion of a neomycin phosphotransferase gene, and the remaining exons in the target plasmid contain the remaining portions of said neomycin phosphotransferase gene.

29. The vector system of claim 22, wherein the second selectable marker protein which is different from said first selectable marker protein is selected from the group consisting of neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine guanine phosphoribosyl transferase.

30. The vector system of claim 22, wherein the marker or the target plasmid further comprises a DNA encoding a third dominant selectable marker protein that is different from the first and second selectable marker proteins.

31. The vector system of claim 30, wherein expression of the DNA encoding a third selectable marker protein permits amplification of said DNA to be inserted into the genome of said cell.

32. The vector system of claim 31, wherein the third selectable marker protein is dihydrofolate reductase.

33. The vector system of claim 22, which provides for insertion of a desired DNA at a targeted site in the genome of a mammalian cell selected from the group consisting of Chinese hamster ovary (CHO) cells, myeloma cells, baby hamster kidney cells, COS cells, NSO cells, HeLa cells and NIH 3T3 cells.

34. The vector system of claim 33, wherein the mammalian cell is a CHO cell.

35. The vector system of claim 22, wherein the marker plasmid further contains a rare restriction endonuclease sequence which is inserted within the region of DNA in the first DNA fragment of the marker plasmid that provides a unique site for homologous recombination.

36. The vector system of claim 22, wherein the region of DNA in the first DNA fragment that provides a unique site for homologous recombination is at least 300 nucleotides.

37. The vector system of claim 36, wherein the region of DNA in the first DNA fragment that provides a unique site for homologous recombination ranges in size from about 300 nucleotides to 20 kilobases.

38. The vector system of claim 37, wherein the region of DNA in the first DNA fragment that provides a unique site for homologous recombination ranges in size from 2 to 10 kilobases.

39. The vector system of claim 22, wherein the DNA encoding the first selectable marker protein is split into at least three exons.

40. The vector system of claim 22, wherein the region of DNA in the first DNA fragment that provides a unique site for homologous recombination is a bacterial DNA, an insect DNA, a viral DNA or a synthetic DNA.

41. The vector system of claim 40, wherein the region of DNA in the first DNA fragment that provides a unique site for homologous recombination does not contain any functional genes.

* * * * *